(12) United States Patent
Krishnan et al.

(10) Patent No.: US 10,443,089 B2
(45) Date of Patent: Oct. 15, 2019

(54) METHODS OF MULTIPLEXING DNA SENSORS AND LOCALIZING DNA SENSOR

(71) Applicant: NATIONAL CENTRE FOR BIOLOGICAL SCIENCES (NCBS-TIFR), Bangalore (IN)

(72) Inventors: Yamuna Krishnan, Bangalore (IN); Souvik Modi, Howrah (IN); Sunaina Surana, Kolkata (IN)

(73) Assignee: National Centre For Biological Sciences (NCBS-TIFR), Bangalore (IN)

( * ) Notice: Subject to any disclaimer, the term of this patent is extended or adjusted under 35 U.S.C. 154(b) by 377 days.

(21) Appl. No.: 14/770,404

(22) PCT Filed: Feb. 25, 2014

(86) PCT No.: PCT/IB2014/059236
§ 371 (c)(1),
(2) Date: Aug. 25, 2015

(87) PCT Pub. No.: WO2014/132191
PCT Pub. Date: Sep. 4, 2014

(65) Prior Publication Data
US 2016/0002713 A1 Jan. 7, 2016

(30) Foreign Application Priority Data
Feb. 26, 2013 (IN) .............................. 846/CHE/2013

(51) Int. Cl.
*C12Q 1/6818* (2018.01)
*C12Q 1/6841* (2018.01)

(52) U.S. Cl.
CPC ......... *C12Q 1/6818* (2013.01); *C12Q 1/6841* (2013.01)

(58) Field of Classification Search
None
See application file for complete search history.

(56) References Cited

U.S. PATENT DOCUMENTS

| | | | |
|---|---|---|---|
| 2003/0096777 A1* | 5/2003 | Besterman | A61K 45/06 514/44 A |
| 2004/0009510 A1* | 1/2004 | Seiwert | A61K 31/7088 435/6.11 |
| 2004/0166553 A1 | 8/2004 | Nguyen et al. | |
| 2004/0219523 A1 | 11/2004 | Stanton et al. | |

(Continued)

FOREIGN PATENT DOCUMENTS

WO 2012140274 10/2012

OTHER PUBLICATIONS

PCT/IB14/59236, International Search Report and Written Opinion, dated Mar. 10, 2015, 10 pages.

*Primary Examiner* — Robert T. Crow
(74) *Attorney, Agent, or Firm* — Kilpatrick Townsend & Stockton LLP

(57) ABSTRACT

The present disclosure relates to a method of multiplexing DNA sensors and optionally measuring pH in cell, a method of localizing DNA sensor in Golgi Network of scFv-Furin expressing cell and a method of identifying optimal location of fluorophore pair on the DNA sensor for multiplexing DNA sensors. The DNA sensors of the present disclosure follow independent cellular pathways and do not interact with or compromise functionality of another DNA sensor.

14 Claims, 36 Drawing Sheets

Specification includes a Sequence Listing.

(56) References Cited

U.S. PATENT DOCUMENTS

2006/0094868 A1\* 5/2006 Giuliano ............ C07K 14/4721
                                                536/23.2
2010/0159468 A1   6/2010 Haslam
2010/0304370 A1  12/2010 Krishnan et al.

\* cited by examiner

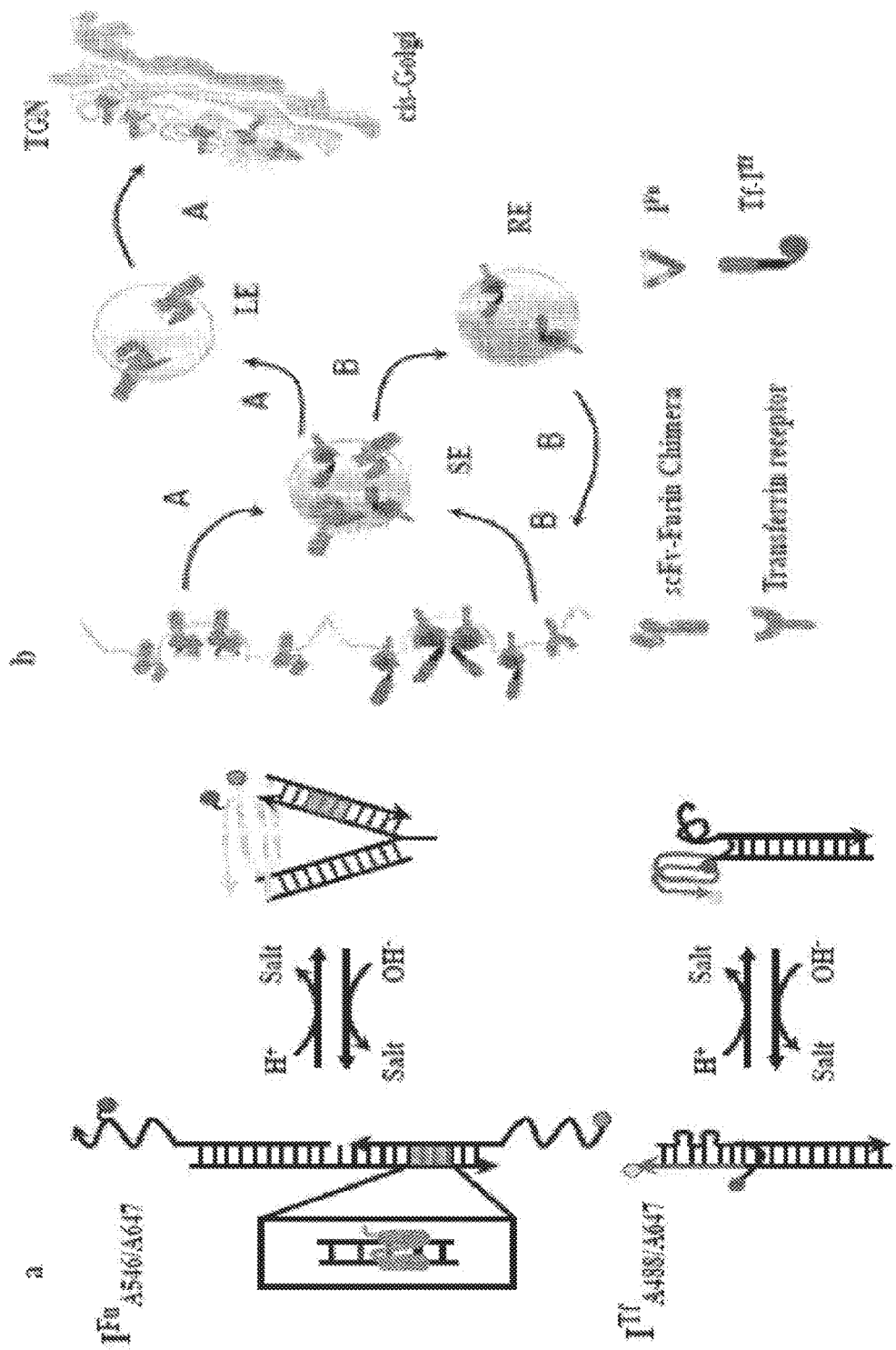
FIGURE 1 (a) & (b)

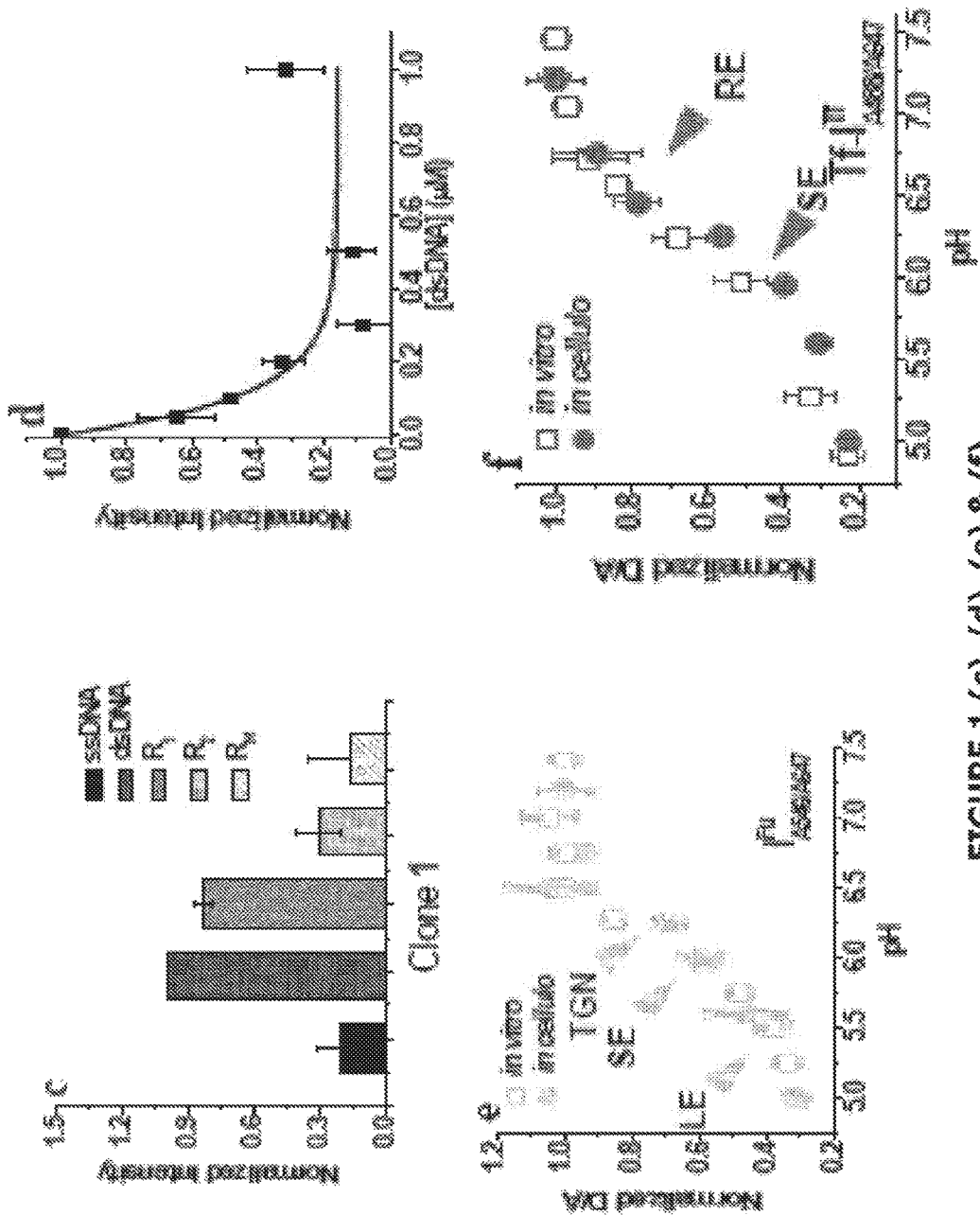
FIGURE 1 (c), (d), (e) & (f)

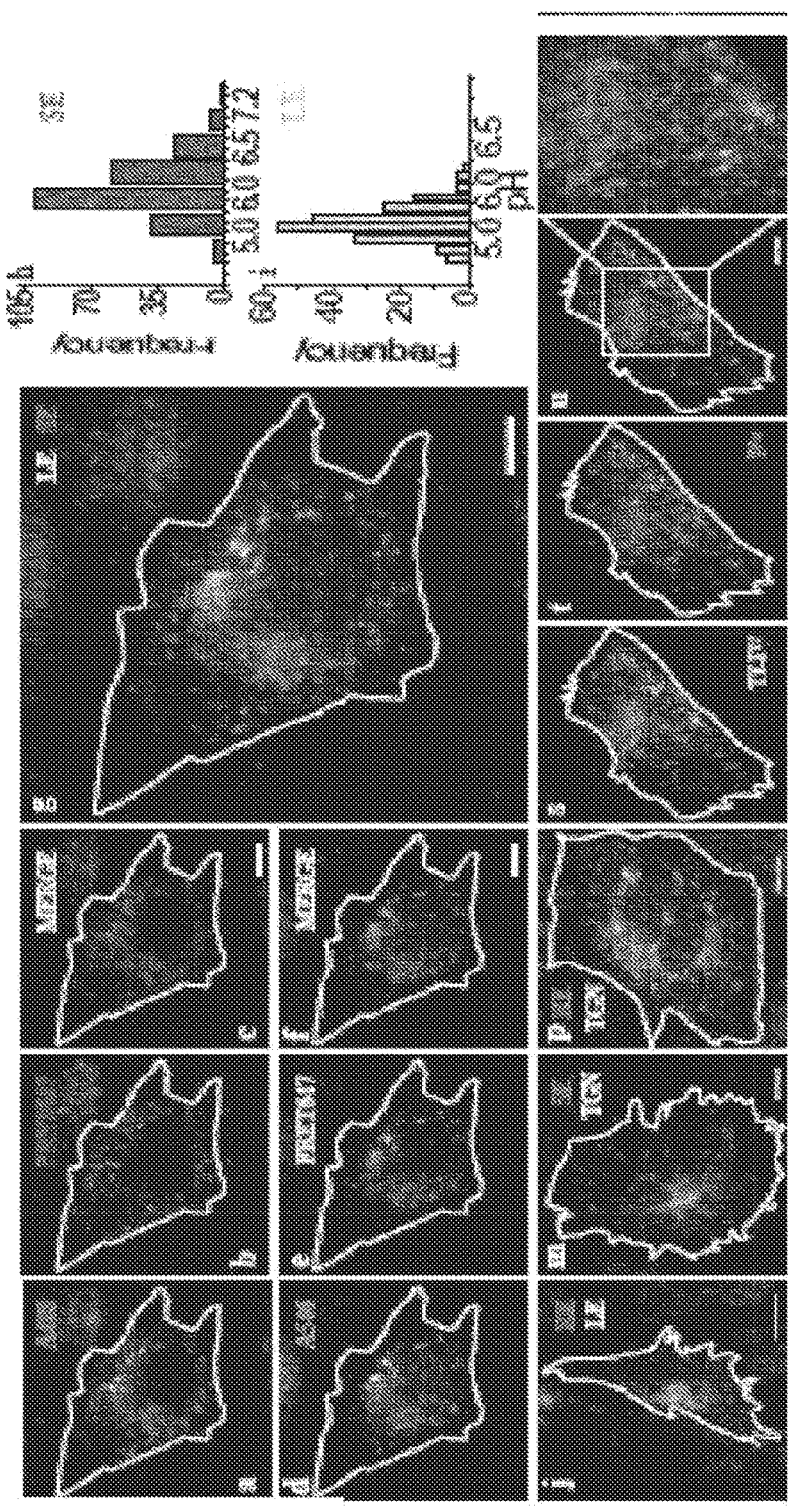
FIGURE 4 (a) to (j), (m), (p), (s), (t) & (u)

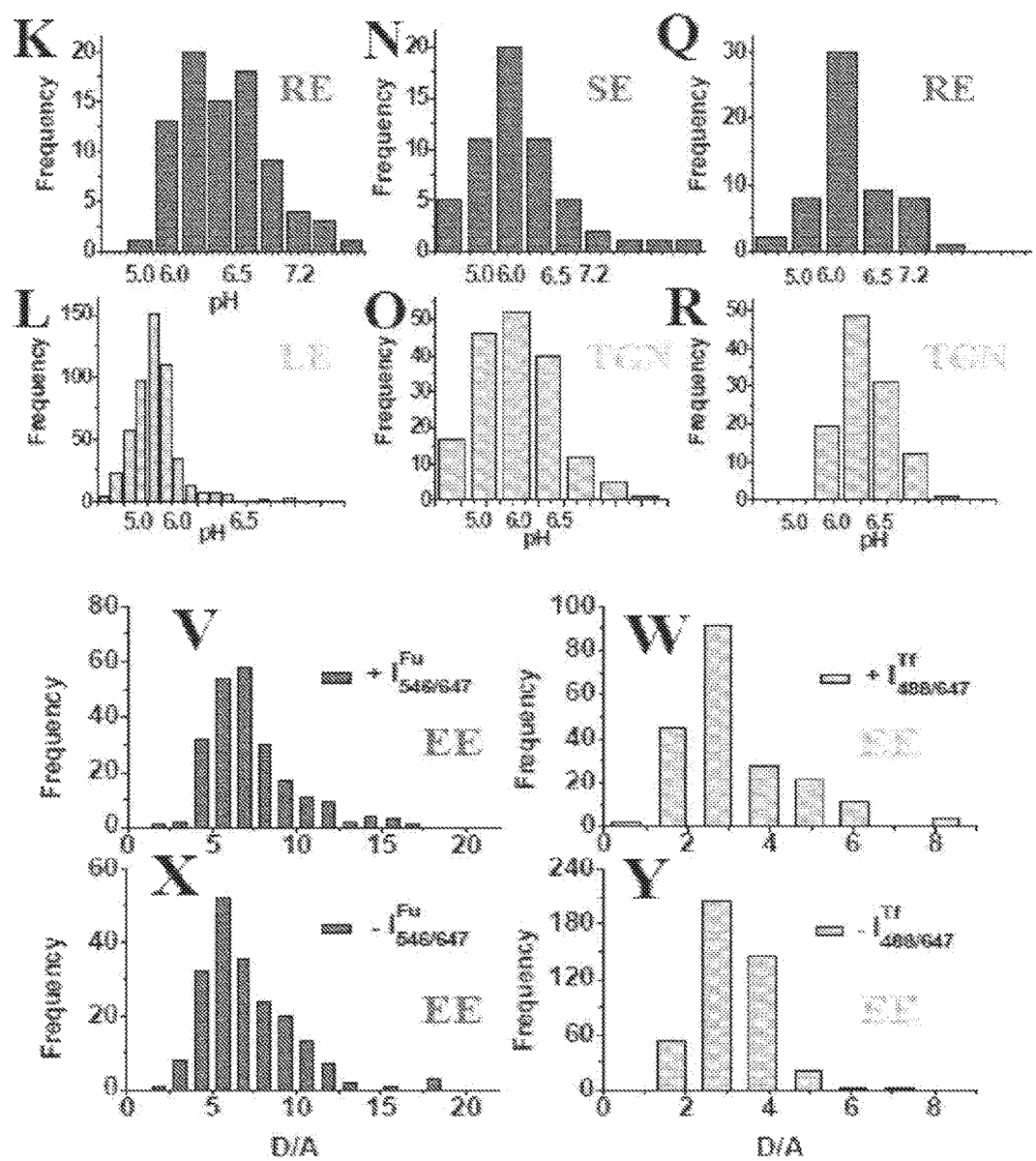
FIGURE 4 (k), (l), (n), (o), (q), (r) & (v) to (y)

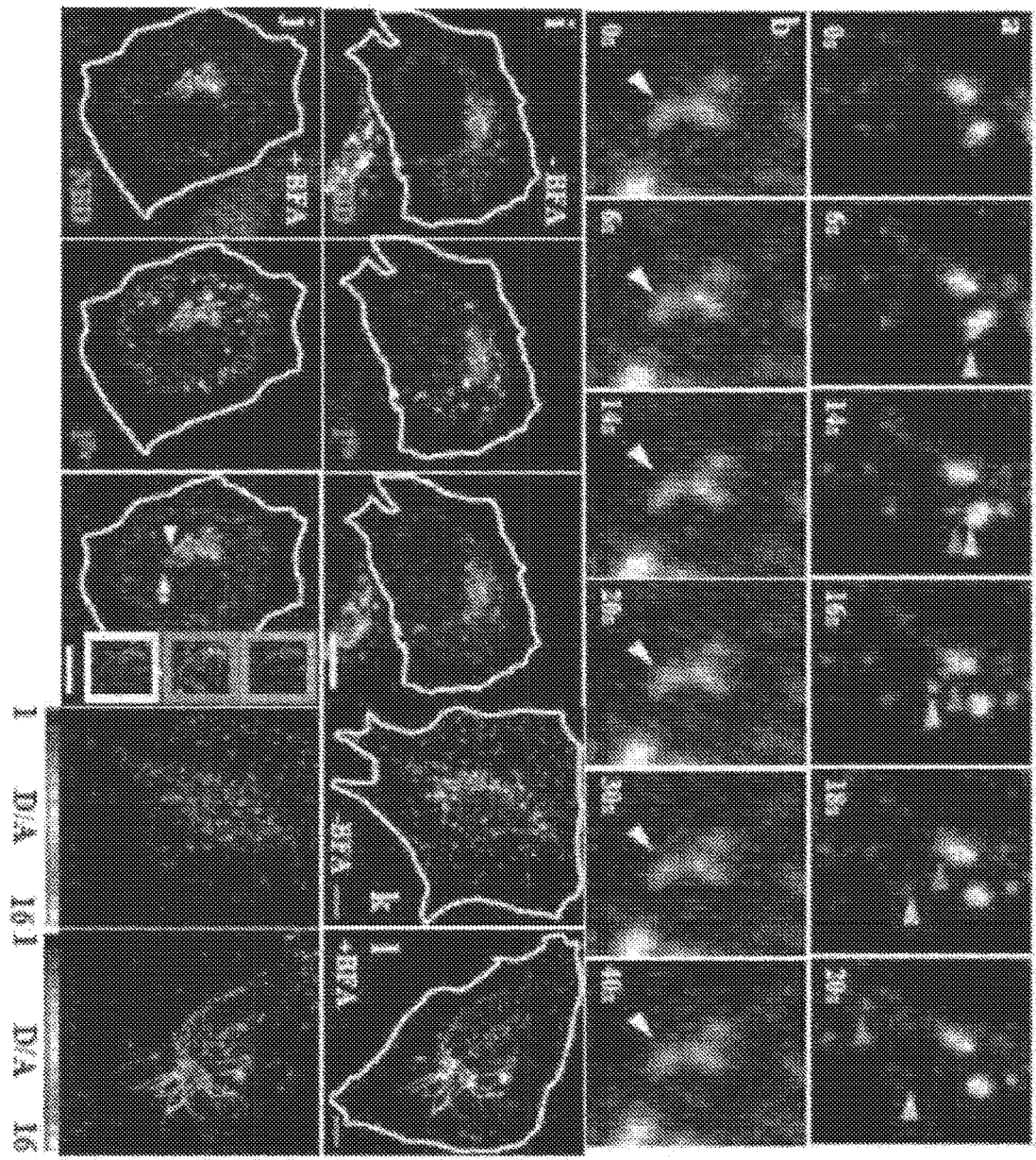
FIGURE 5 (a), (b), (i) to (l)

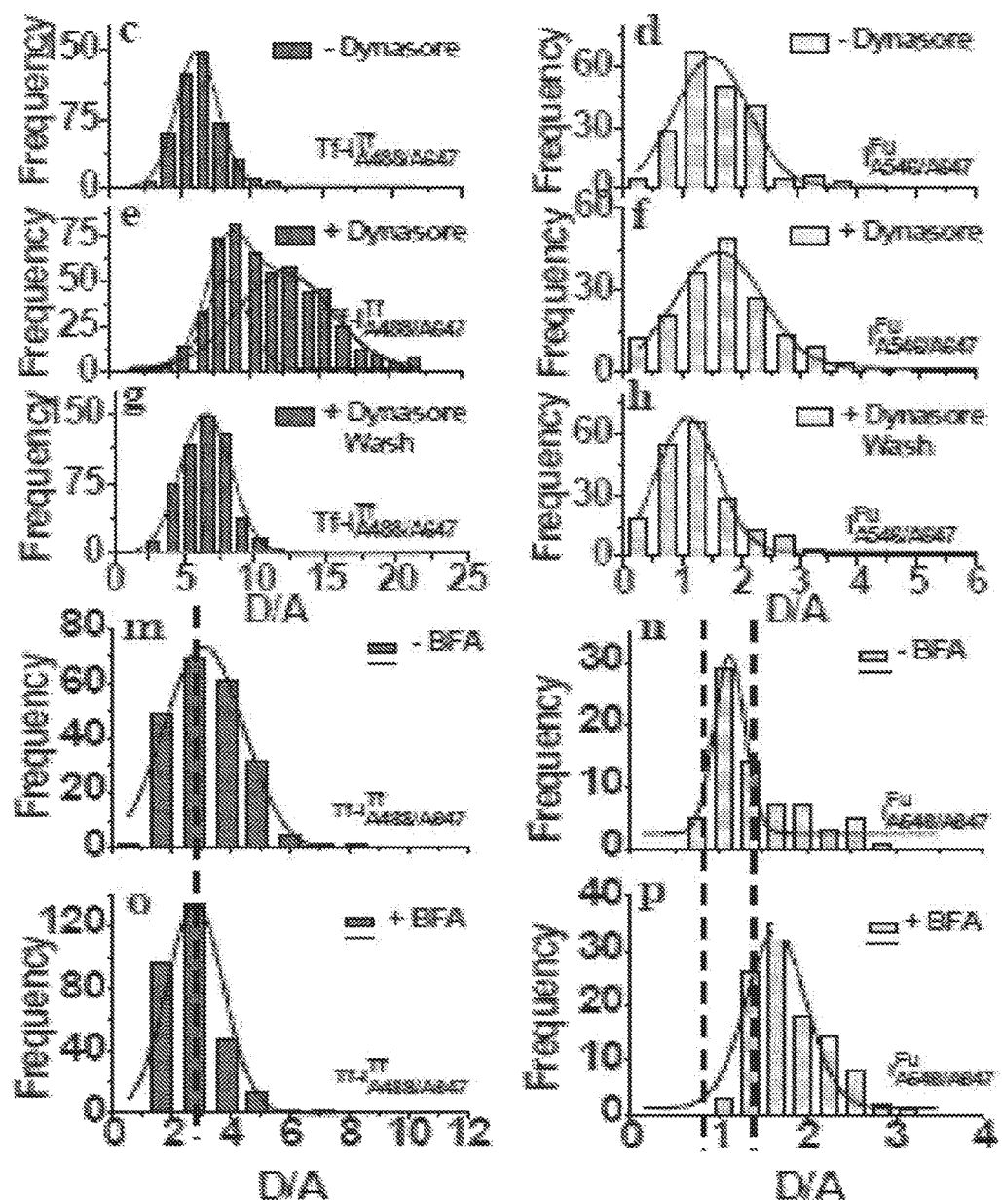
FIGURE 5 (c) to (h), (m) to (p)

$I^{Fu}$: The trimolecular I-switch marking the Furin retrograde pathway
Acceptor position (Alexa-647)        Alexa-546 (Donor)
a.
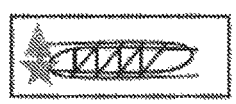
Acceptor on nucleotide 26 of
oligo O2
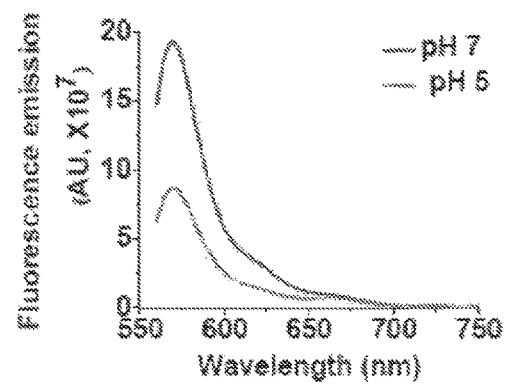
Fold change ≈ 1.78
b.
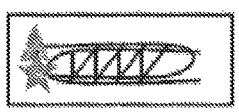
Acceptor on nucleotide 27 of
oligo O2
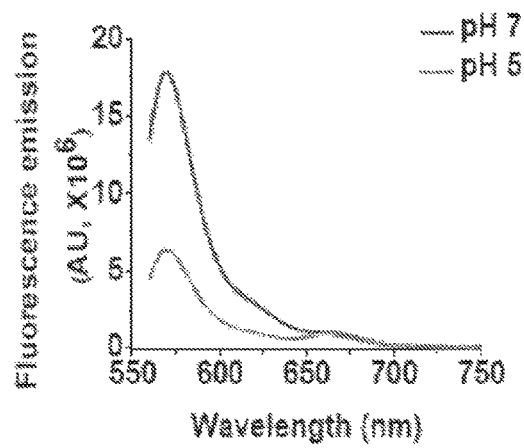
Fold change ≈ 2.92
FIGURE 23 (a) & (b)

c.
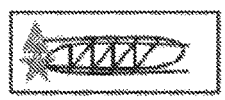
Acceptor on nucleotide 28 of oligo O2
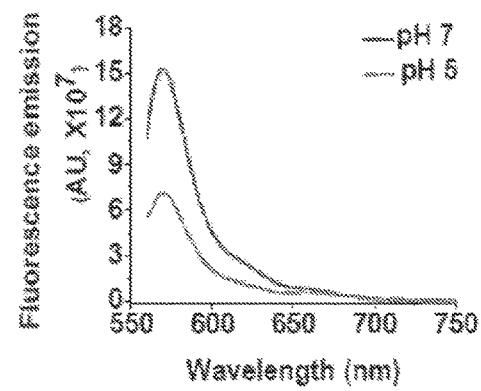
Fold change ≈ 1.76
d.
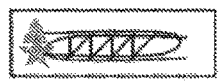
Acceptor on nucleotide 29 of oligo O2
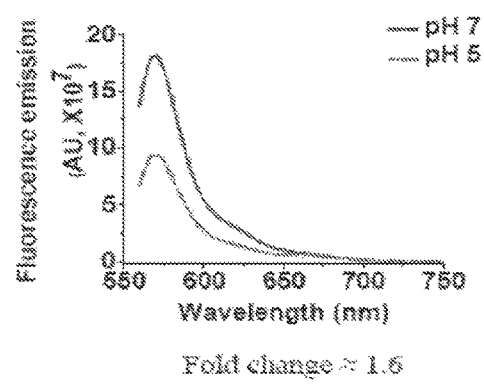
Fold change ≈ 1.6
e.
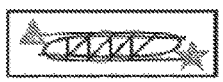
Acceptor on nucleotide 32 of oligo O2
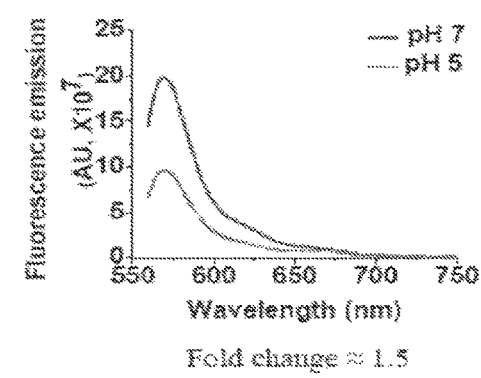
Fold change ≈ 1.5
FIGURE 23 (c) to (e)

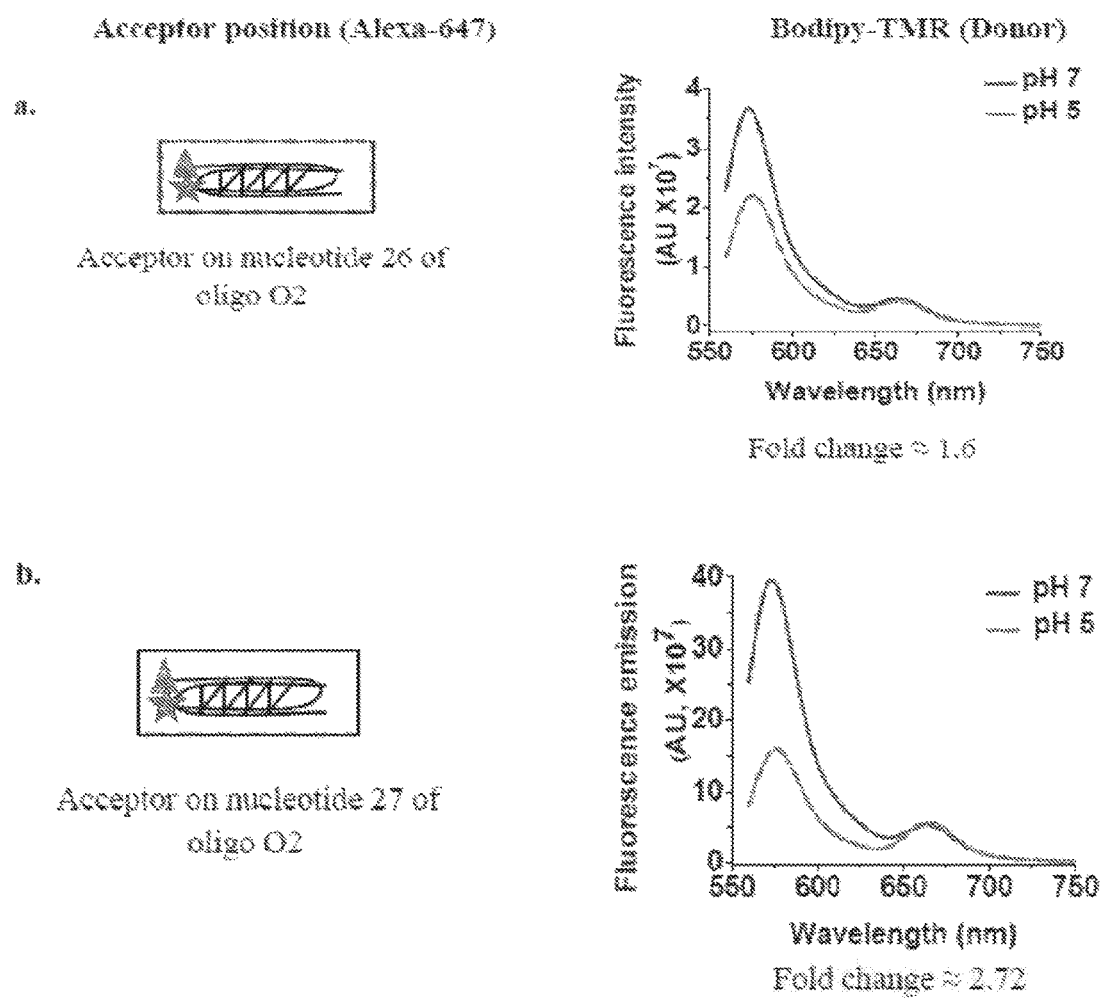
FIGURE 25 (a) & (b)

c.
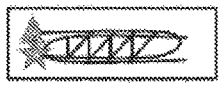
Acceptor on nucleotide 28 of oligo O2
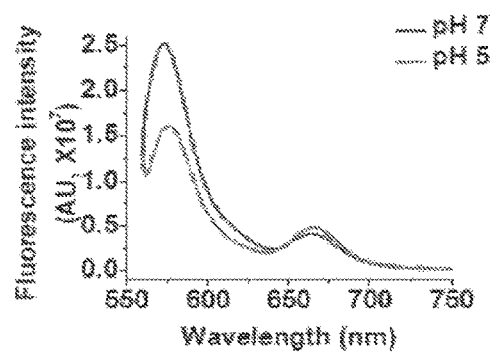
Fold change ≈ 1.96
d.
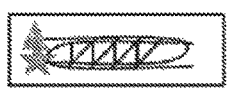
Acceptor on nucleotide 29 of oligo O2
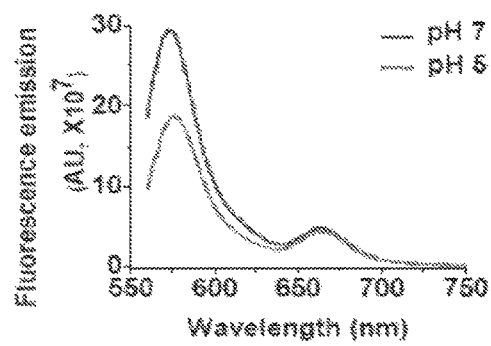
Fold change ≈ 1.45
e.
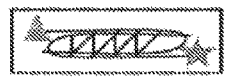
Acceptor on nucleotide 32 of oligo O2
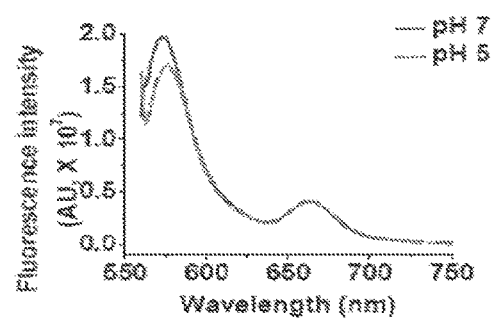
Fold change ≈ 1.27
FIGURE 25 (c) to (e)

$I^{Tf}$: The bimolecular I-switch marking the Transferrin Recycling Pathway
a. 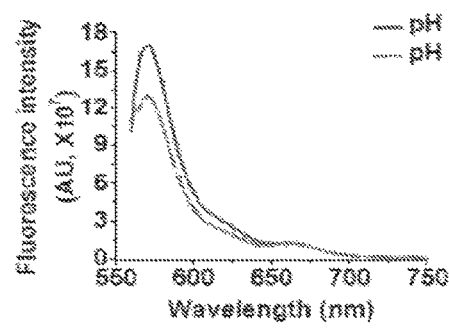
Fold change ≈ 1.25
b. 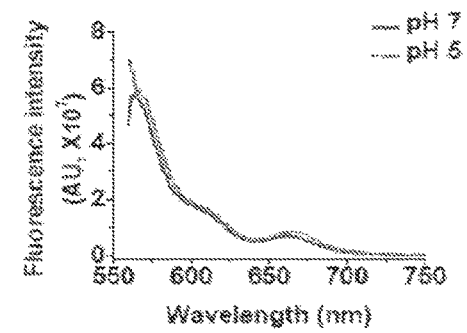
Fold change < 1.0
FIGURE 26

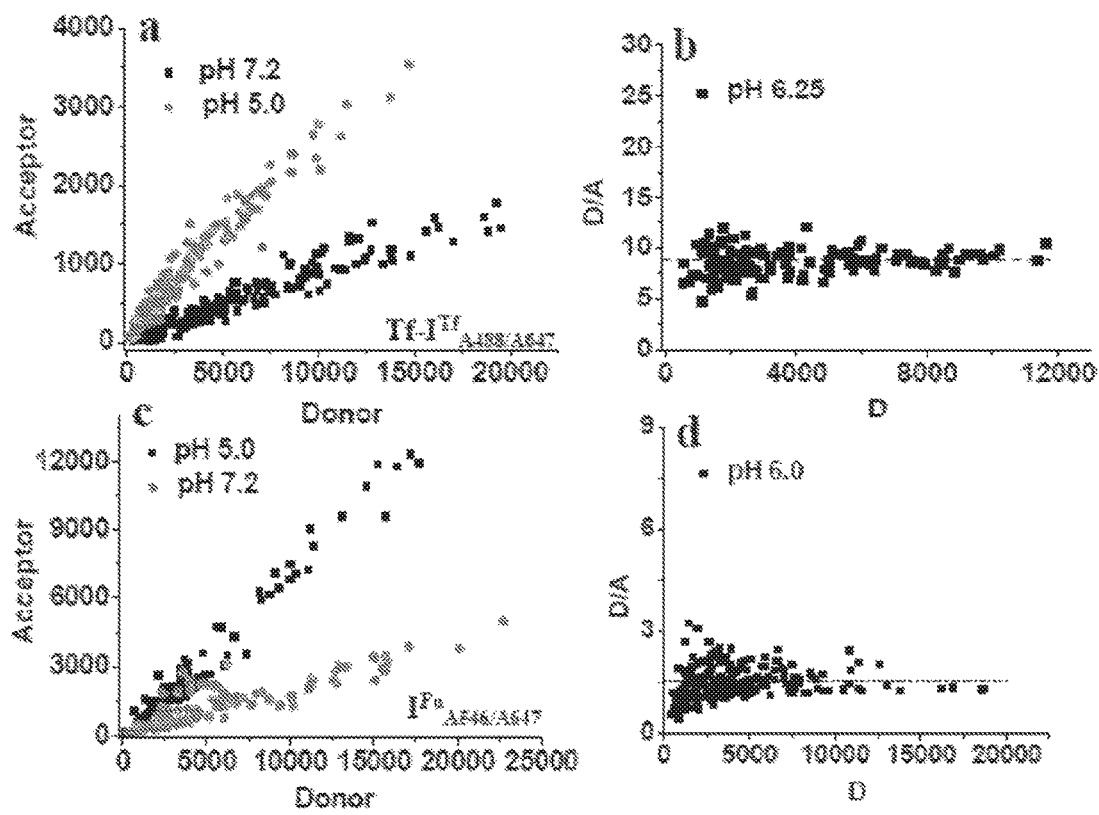
FIGURE 28 (a) to (d)

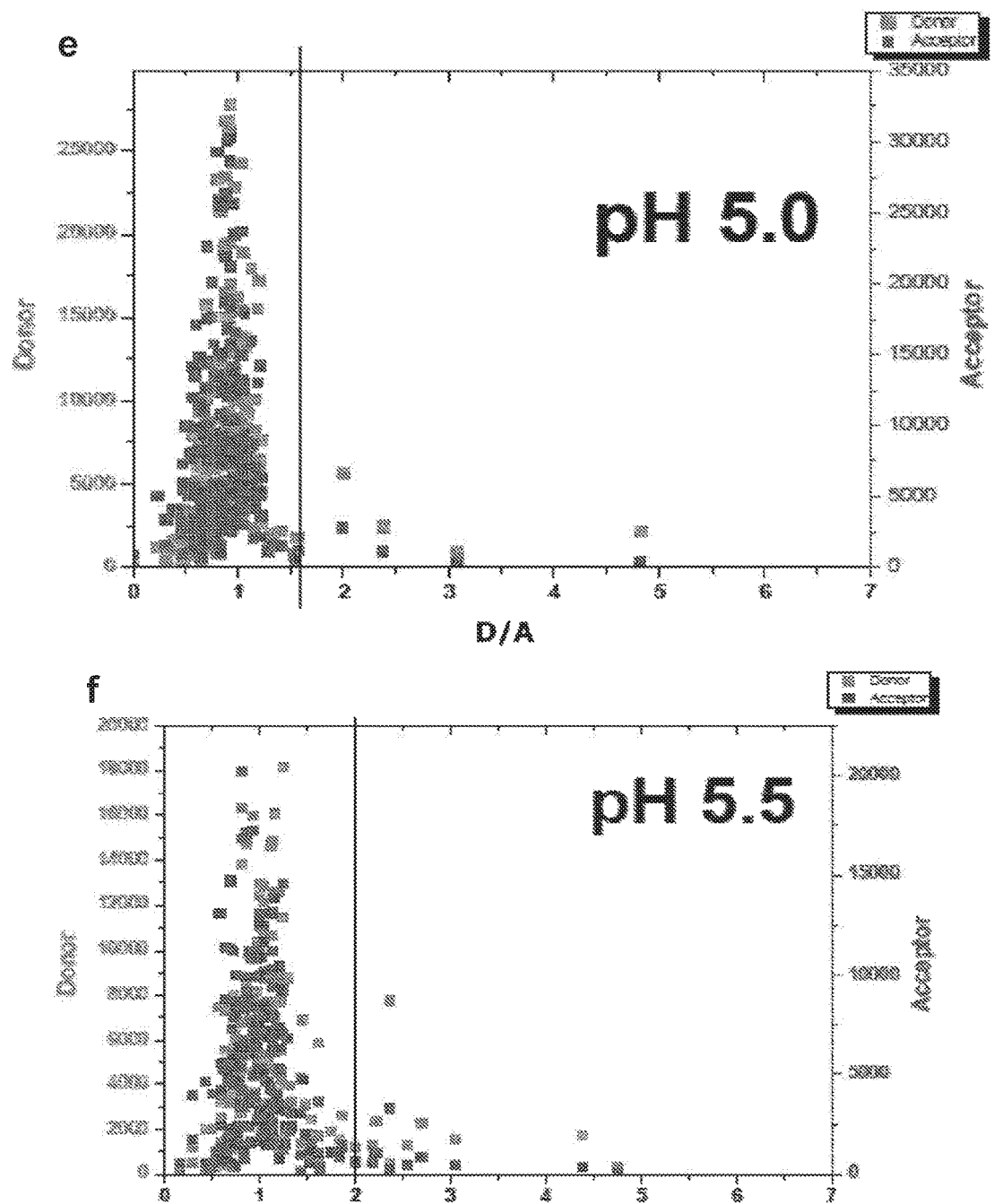
FIGURE 28 (e) and (f)

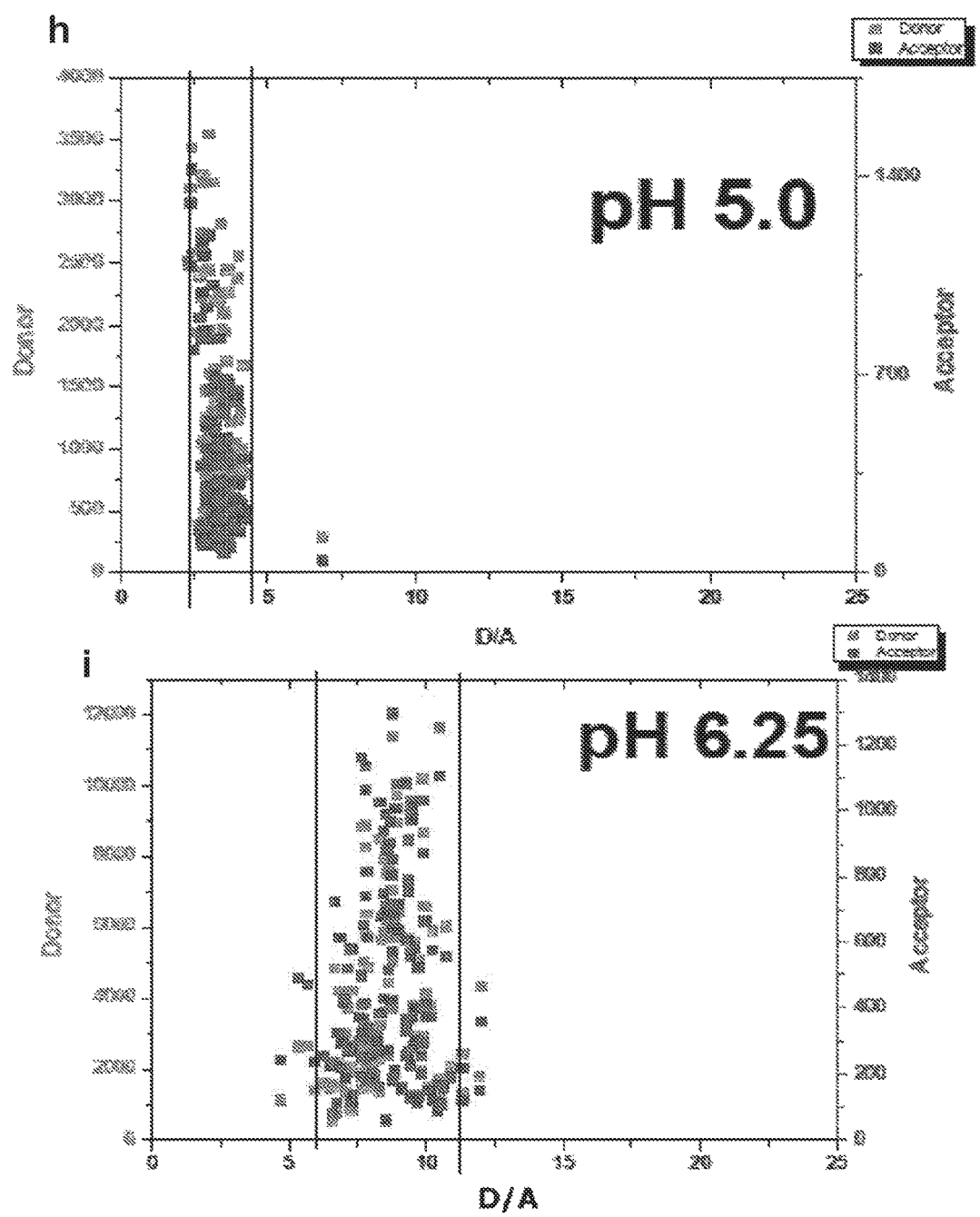
FIGURE 28 (h) and (i)

SEQUENCE LISTING

<160> NUMBER OF SEQ ID NOS: 16

<210> SEQ ID NO 1
<211> LENGTH: 60
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(60)

<400> SEQUENCE: 1
ccsctaaccc ctaacccta accccatata tatcctagaa cgacagacaa acagtgagtc    60

<210> SEQ ID NO 2
<211> LENGTH: 57
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(57)

<400> SEQUENCE: 2
gactcactgt tgtctgtcg ttctaggata tatattttgt tatgtgttat gtgttat        57

<210> SEQ ID NO 3
<211> LENGTH: 58
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(58)

<400> SEQUENCE: 3
cccctaaccc ctaaccccta acccctttaa ataggcaccg gcatgcgcag tctgacgt       58

<210> SEQ ID NO 4
<211> LENGTH: 55
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(55)

<400> SEQUENCE: 4
acgtcagact gcgcatgccg gtgcctattt aaatttgtta tgtgttatgt gttat          55

<210> SEQ ID NO 5
<211> LENGTH: 32
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(32)

<400> SEQUENCE: 5
ccgaccgcag gatcctataa aaccccaacc cc                                   32

<210> SEQ ID NO 6
<211> LENGTH: 32
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(32)

<400> SEQUENCE: 6
ccccaacccc aatacattta tatatatcct ag                                   32

<210> SEQ ID NO 7
<211> LENGTH: 41

```
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(41)

<400> SEQUENCE: 7
ttataggatc ctgcggtcgg actaggatat atataaatgt a                           41

<210> SEQ ID NO 8
<211> LENGTH: 39
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(39)

<400> SEQUENCE: 8
aaaagactca ctgtttgtct gtcgttctag gatatatat                              39

<210> SEQ ID NO 9
<211> LENGTH: 35
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(35)

<400> SEQUENCE: 9
atatatatcc tagaacgaca gacaaacagt gagtc                                  35

<210> SEQ ID NO 10
<211> LENGTH: 13
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(13)

<400> SEQUENCE: 10
atatatatcc tag                                                          13

<210> SEQ ID NO 11
<211> LENGTH: 13
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(13)

<400> SEQUENCE: 11
cgacagacaa aca                                                          13

<210> SEQ ID NO 12
<211> LENGTH: 13
<212> TYPE: DNA
<213> ORGANISM: Artificial Sequence
<220> FEATURE:
<223> OTHER INFORMATION: NUCLEIC ACID ASSEMBLY
```

```
<220> FEATURE:
<221> NAME/KEY: gene
<222> LOCATION: (1)..(13)

<400> SEQUENCE: 12
cctagaacga cag                                                          13

<210> SEQ ID NO 13
<211> LENGTH: 48
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(48)

<400> SEQUENCE: 13
atatatatcc tagaacgaca gacaaacagt gagtccgcat tgttacat                    48

<210> SEQ ID NO 14
<211> LENGTH: 48
<212> TYPE: DNA
<213> ORGANISM: Artificial Sequence
<220> FEATURE:
<223> OTHER INFORMATION: NUCLEIC ACID ASSEMBLY
<220> FEATURE:
<221> NAME/KEY: gene
<222> LOCATION: (1)..(48)

<400> SEQUENCE: 14
atgtaacaat gcggactcac tgtttgtctg tcgttctagg atatatat                    48

<210> SEQ ID NO 15
<211> LENGTH: 815
<212> TYPE: DNA
<213> ORGANISM: Artificial Sequence
<220> FEATURE:
<223> OTHER INFORMATION: scFv Sequence
<220> FEATURE:
<221> NAME/KEY: gene
<222> LOCATION: (1)..(815)

<400> SEQUENCE: 15
atggccgagg tgcagctgtt ggagtctggg ggaggcttgg tacagcctgg ggggtccctg        60
agactctcct gtgcagcctc tggattcacc tttagcagct atgccatgag ctgggtccgc       120
caggctccag ggaagggget ggagtgggtc tcaacgatta cgaagagggg tgagaggaca       180
aagtacgcag actccgtgaa gggccggttc accatctcca gagacaattc caagaacacg       240
ctgtatctgc aaatgaacag cctgagagcc gaggacacgg ccgtatatta ctgtgcgaaa       300
agtactcgtg cgtttgacta ctggggccag ggaaccctgg tcaccgtctc gagcggtgga       360
ggcggttcag gcggaggtgg cagcggcggt ggcgggtcga cggacatcca gatgacccag       420
tctccatcct ccctgtctgc atctgtagga gacagagtca ccatcacttg ccgggcaagt       480
cagagcatta gcagctattt aaattggtat cagcagaaac cagggaaagc ccctaagctc       540
ctgatctatg ggcatcccta tttgcaaagt ggggtcccat caaggttcag tggcagtgga       600
tctgggacag atttcactct caccatcagc agtctgcaac tgaagatttt gcaacttac        660 tactgtcaac agacgcgttt ttcgcctaat acgttcggcc aagggaccaa ggtggaaatc       720
aaacgggcgg ccgcacatca tcatcaccat cacggggccg cagaacaaaa acccatctca       780
gaagaggatc tgaatggggc cgcaggtggg gatct                                  815
```

```
-continued

<210> SEQ ID NO 16
<211> LENGTH: 271
<212> TYPE: PRT
<213> ORGANISM: Artificial Sequence
<220> FEATURE:
<223> OTHER INFORMATION: scFv Protein Sequence
<220> FEATURE:
<221> NAME/KEY: DNA_BIND
<222> LOCATION: (1)..(271)

<400> SEQUENCE: 16

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Thr Lys Arg Gly Glu Arg Thr Lys Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Thr Arg Ala Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Gly Ala Ser Tyr Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Thr Arg Phe Ser Pro Asn Thr Phe Gly Gln Gly Thr Lys Val Glu Ile
225                 230                 235                 240

Lys Arg Ala Ala Ala His His His His His Gly Ala Ala Glu Gln
                245                 250                 255

Lys Pro Ile Ser Glu Glu Asp Leu Asn Gly Ala Ala Gly Gly Asp
            260                 265                 270
```

METHODS OF MULTIPLEXING DNA SENSORS AND LOCALIZING DNA SENSOR

CROSS REFERENCE TO RELATED APPLICATIONS

This application is the US national stage of PCT/IB2014/059236, filed Feb. 25, 2014, which claims the benefit of priority to Indian Patent Application No. 846/CHE/2013, filed Feb. 26, 2013, the disclosures of both of which are incorporated herein by reference in their entirety.

TECHNICAL FIELD

The present disclosure relates to simultaneous pH mapping of different cellular pathways in the same cell by use of different DNA sensors. The present disclosure also relates to preparing FRET pairs which are compatible with each other in FRET Microscopy of live cells and optimising their position on the DNA sensors to maximise their efficiency for multiplexing of DNA sensors. The DNA sensors operate on independent pathways, do not interact with each other and their functionality is not compromised. The present disclosure further relates to a method of localizing DNA sensor in the Golgi network of scFv-Furin expressing cell.

BACKGROUND AND PRIOR ART OF THE DISCLOSURE

The modular and programmable nature of DNA, coupled with its capacity for molecular recognition, positions DNA sensors as a uniquely versatile scaffold for molecular sensing within the cellular milieu. Sensors based on alternative scaffolds such as small molecule sensors Fluorescein and SNARF or GFP based pH sensors like pHluorin are significantly challenged in order to achieve simultaneous sensing of a specific analyte in multiple environments within the same cell. This has limited the study of fusion and fission events in biological systems e.g., endocytic sorting.

DNA has been molecularly chiselled to create a variety of intricate architectures on the nanoscale. Those DNA nano-architectures that can be chemically or physically triggered to switch between defined states, referred to as DNA sensors, present great potential for robotic and sensing applications on the nanoscale. Sub-cellular architectures are such nanoscale environments that offer rich possibilities to demonstrate functionality of these DNA nanoarchitectures.

The prior art achieves the mapping of intersecting endocytic pathways for receptors that (a) have cognate ligands (b) where the ligands are chemically functionalizable and (c) where such chemical functionalization of the ligand does not alter its trafficking characteristics. The vast majority of proteins that traffic via the plasma membrane do not satisfy these above criteria. In fact, several highly important trafficking membrane proteins do not fall into this category, and a full elucidation of their pathways has remained elusive. These pathways are now accessible using the targeting strategy described in the present disclosure.

The simultaneous functionality of multiple DNA sensors within the same cell still represents an outstanding challenge, the realisation of which would open up possibilities of multiplexed sensing and/or therapies in living systems. In order to realise this, the precise positioning of more than one DNA nanodevice within subcellular environments and demonstrating their simultaneous functionality therein is essential.

The present disclosure describes a technology called "SimpHony" (Simultaneous pH mapping Technology) based on DNA sensors, which demonstrates the simultaneous use of two or more DNA nanodevices within the same cell, each molecularly programmed to target a different cellular pathway and engineered to map pH gradients along the pathway. This technology is also called Multiplexing of DNA sensors.

STATEMENT OF THE DISCLOSURE

Accordingly, the present disclosure relates to a method of multiplexing DNA sensors and optionally measuring pH in cell, wherein said DNA sensor comprises Nucleic Acid Assembly and fluorophore, optionally along with protein, said method comprising acts of—a) adding the DNA sensors to the cell in labelling media for cellular uptake, to obtain a cell with the DNA sensors, b) incubating the cell obtained in step a) in the labelling media for multiplexing the DNA sensors, wherein the DNA sensors are engineered to follow specific cellular pathways within the cell, and c) mapping the multiplexed DNA sensors within the cell at time intervals, optionally determining D/A ratio and obtaining calibration curve for measuring pH in the cell; a method of localizing DNA sensor comprising Nucleic Acid Assembly and fluorophore, optionally along with protein, in Golgi Network of scFv-Furin expressing cell, said method comprising acts of—a) adding the DNA sensor to the scFv-Furin expressing cell in labelling media for cellular uptake, to obtain the scFv-Furin expressing cell with the DNA sensor within it, b) incubating the cell obtained in step a) in the labelling media and adding molecular marker, and c) determining position of the marker and the DNA sensor within the cell to observe localization of the DNA sensor in the Golgi Network of the scFv-Furin expressing cell; and a method of identifying optimal location of fluorophore pair on DNA sensor for multiplexing DNA sensors, wherein the DNA sensor comprises Nucleic Acid Assembly and fluorophore, optionally along with protein, said method comprising acts of—a) determining spectral overlap between fluorophores and identifying fluorophore pair that displays maximum FRET, wherein the fluorophore pair is for multiplexing of DNA sensors, b) determining optimal location of the fluorophore pair on Nucleic Acid Assembly of the DNA sensor, and c) positioning the fluorophore pair on the Nucleic Acid Assembly of the DNA sensor for multiplexing of DNA sensors.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 1 depicts the concept and molecular programming of DNA nanodevices.

FIG. 4 depicts simultaneous pH mapping of transferrin receptor and furin mediated endocytic pathways using programmed DNA sensors with Sequential pulse (A to R) and Simultaneous pulse (S to W).

FIG. 5 depicts simultaneous pH mapping of organelles with altered morphology.

Figure 9:
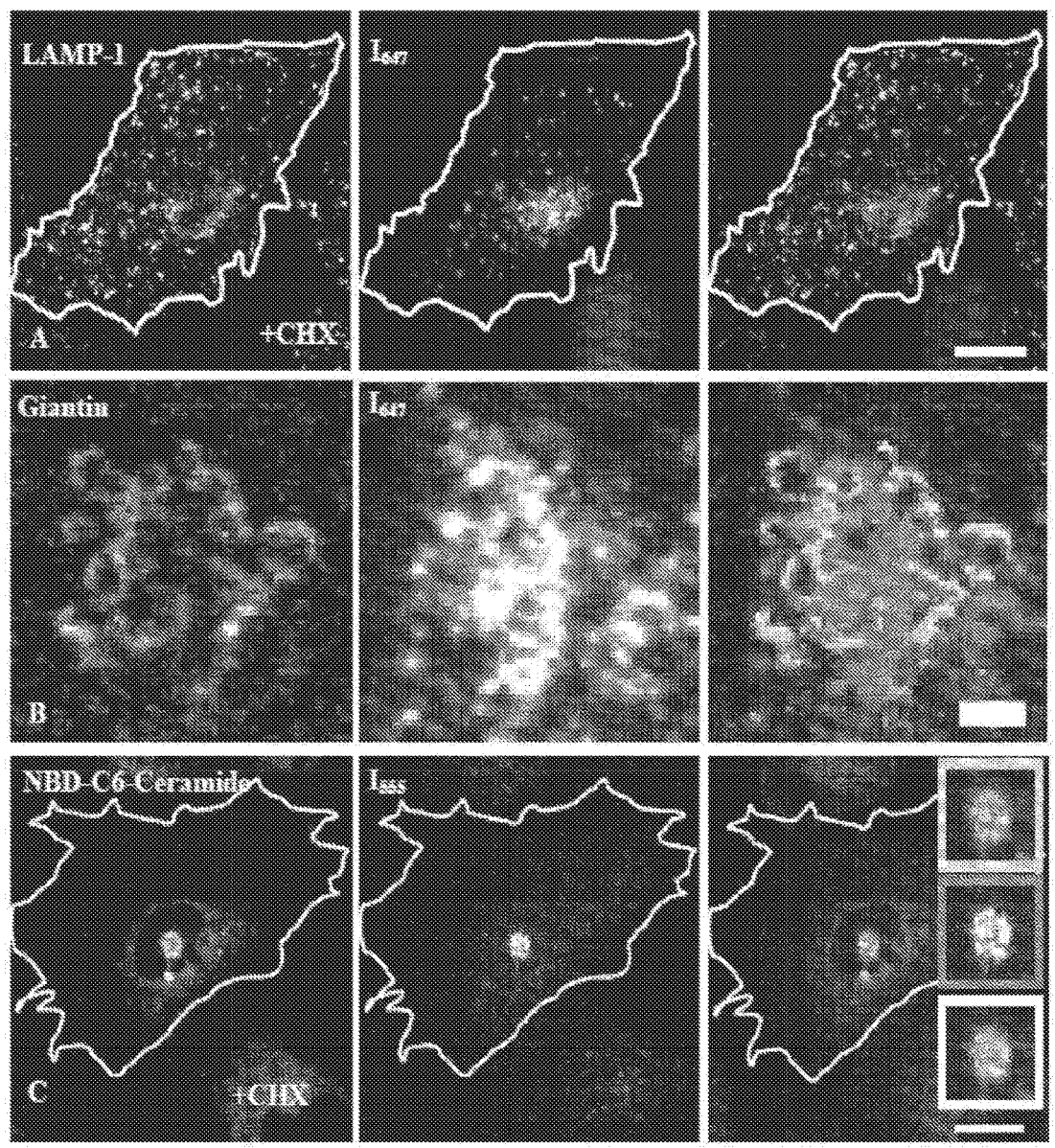

FIG. 9 describes retrograde transport of DNA Sensor into the trans-Golgi network.

Figure 10:
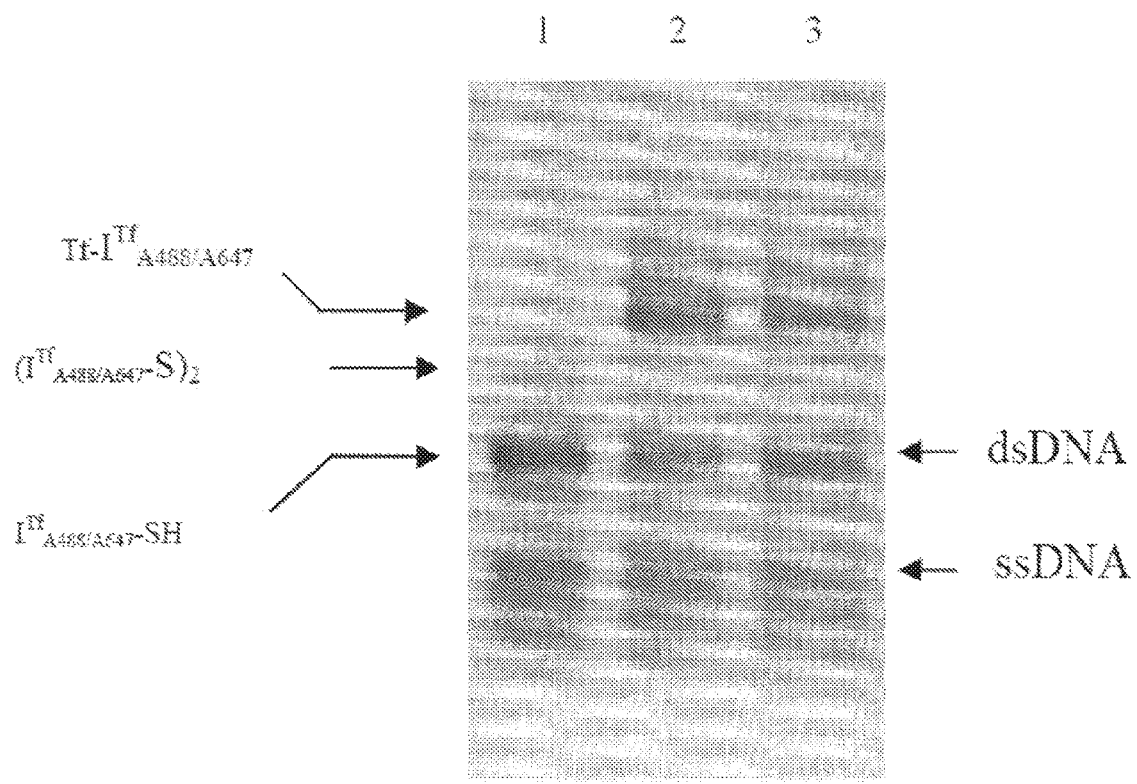

FIG. 10 describes conjugation of $I^{Tf}_{A488/A647}$ with transferrin.

Figure 11:
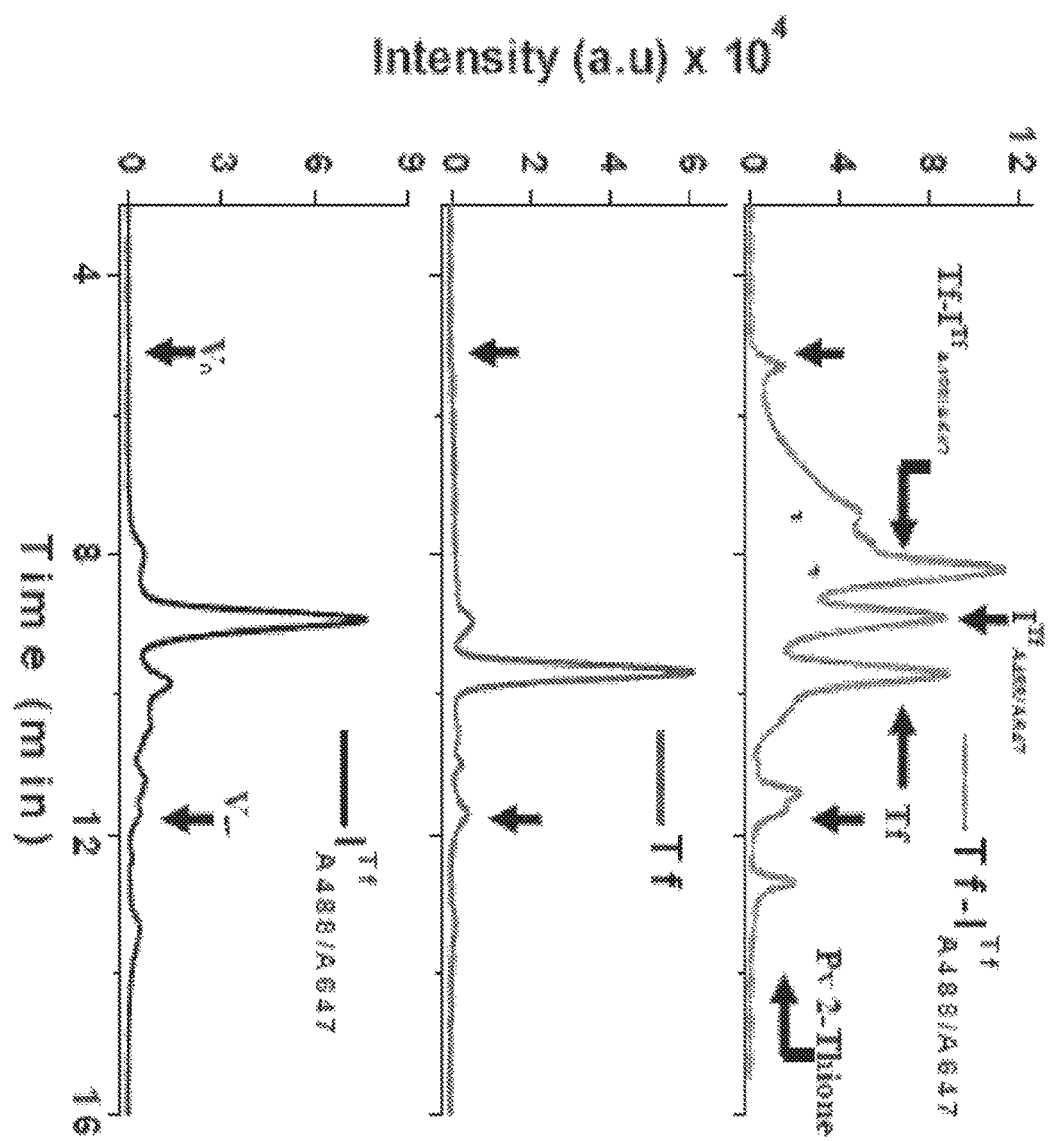

FIG. 11 describes Size Exclusion Chromatography (SEC) purification of DNA conjugates.

Figure 12:
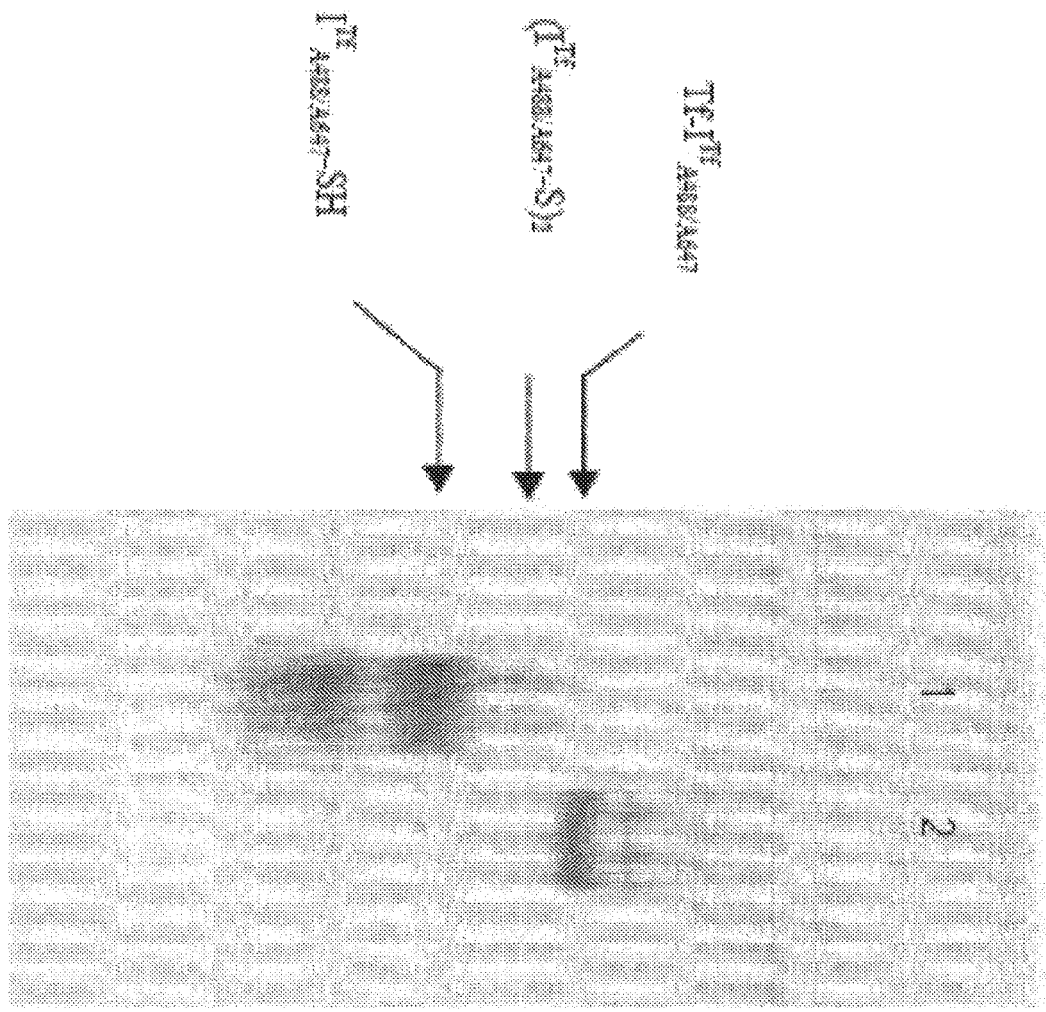

FIG. 12 depicts identification and characterization of Tf-$I^{Tf}$ conjugate separated by SEC-HPLC.

Figure 13:
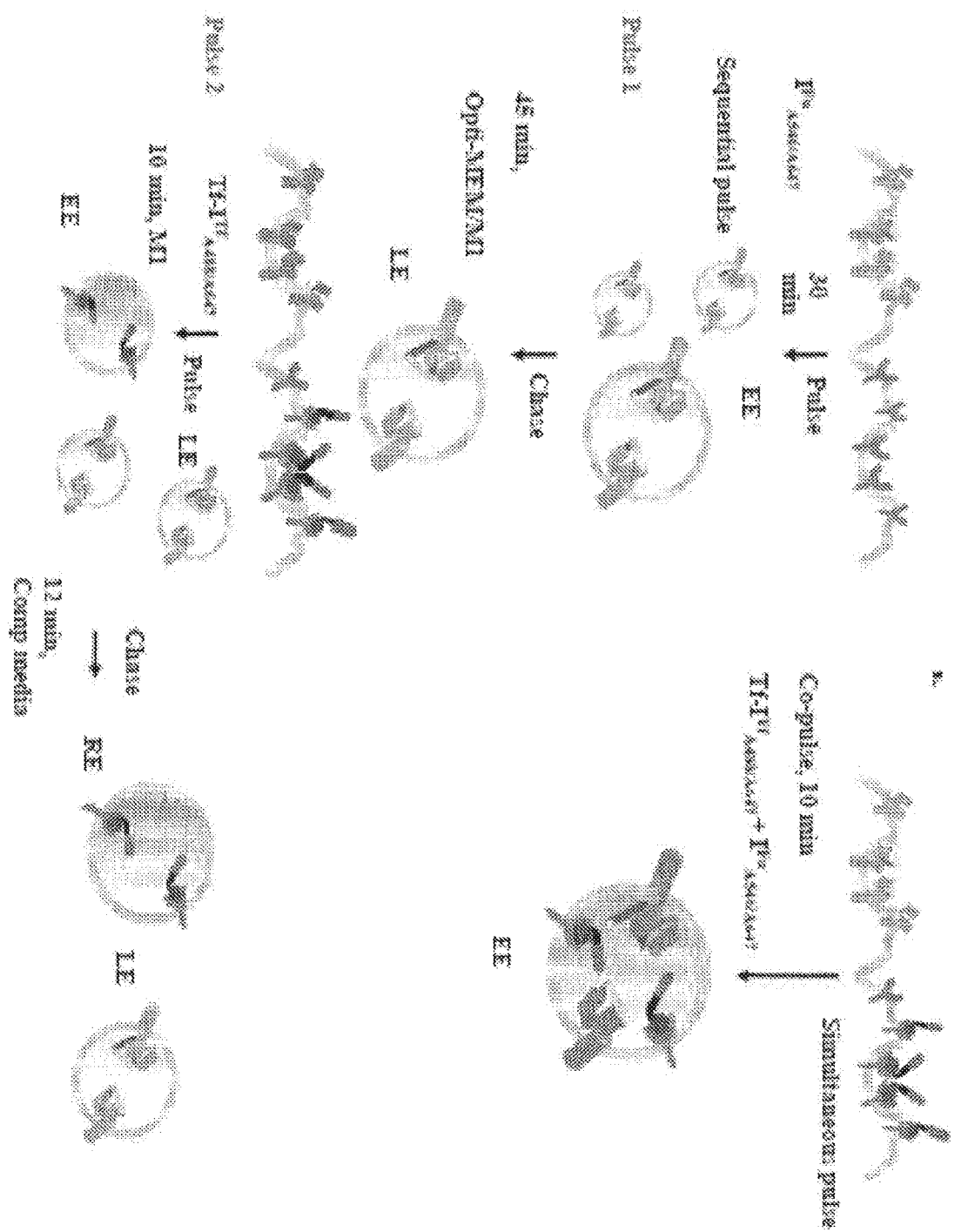

FIG. 13 depicts schematic representation of pulse and chase involved for "SimpHony".

Figures 14, 15:
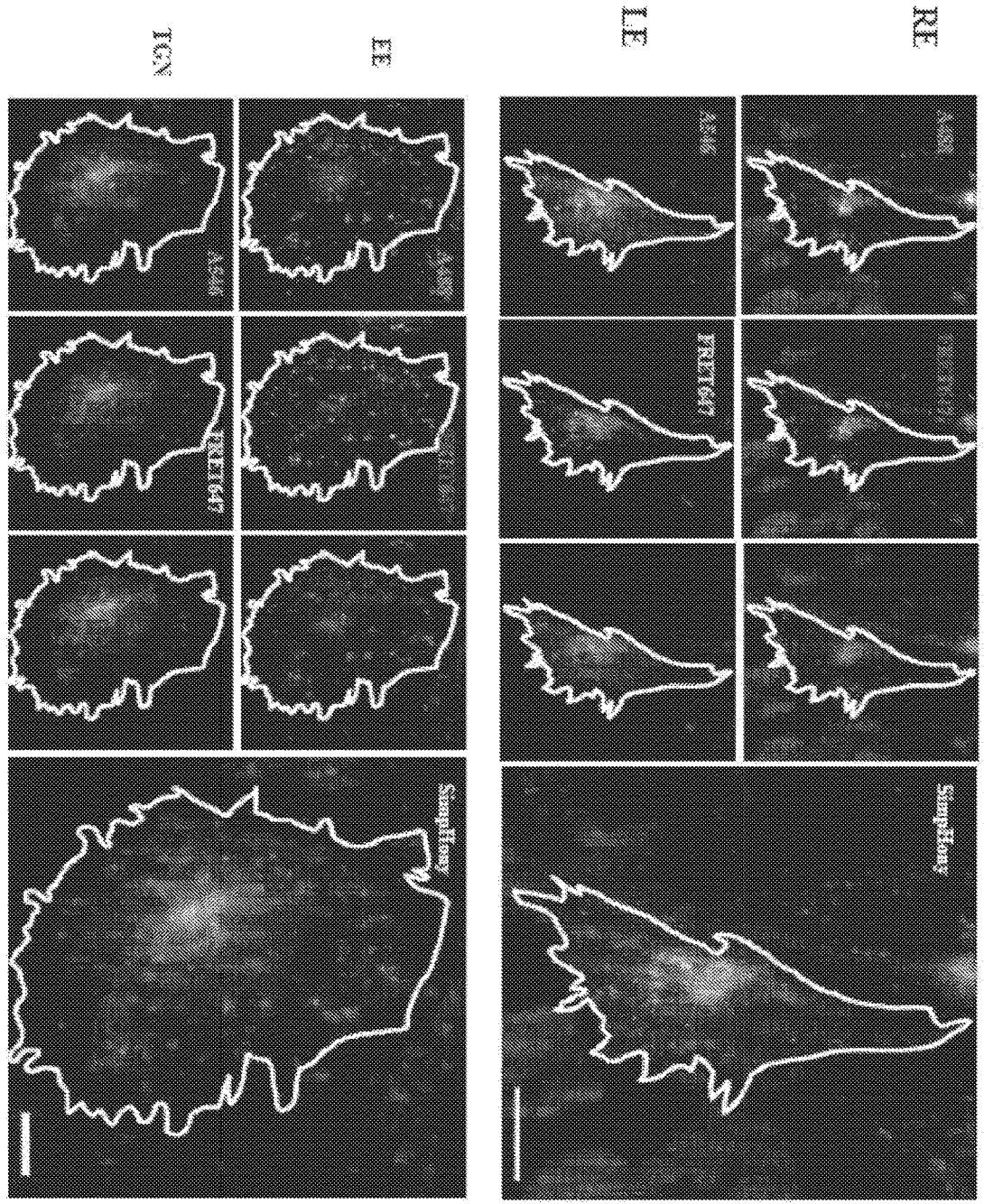

FIG. 14 depicts Simultaneous pH mapping of recycling endosomes and late endosomes.

FIG. 15 depicts Simultaneous pH mapping of early/sorting endosomes and Trans Golgi Network.

Figure 16:
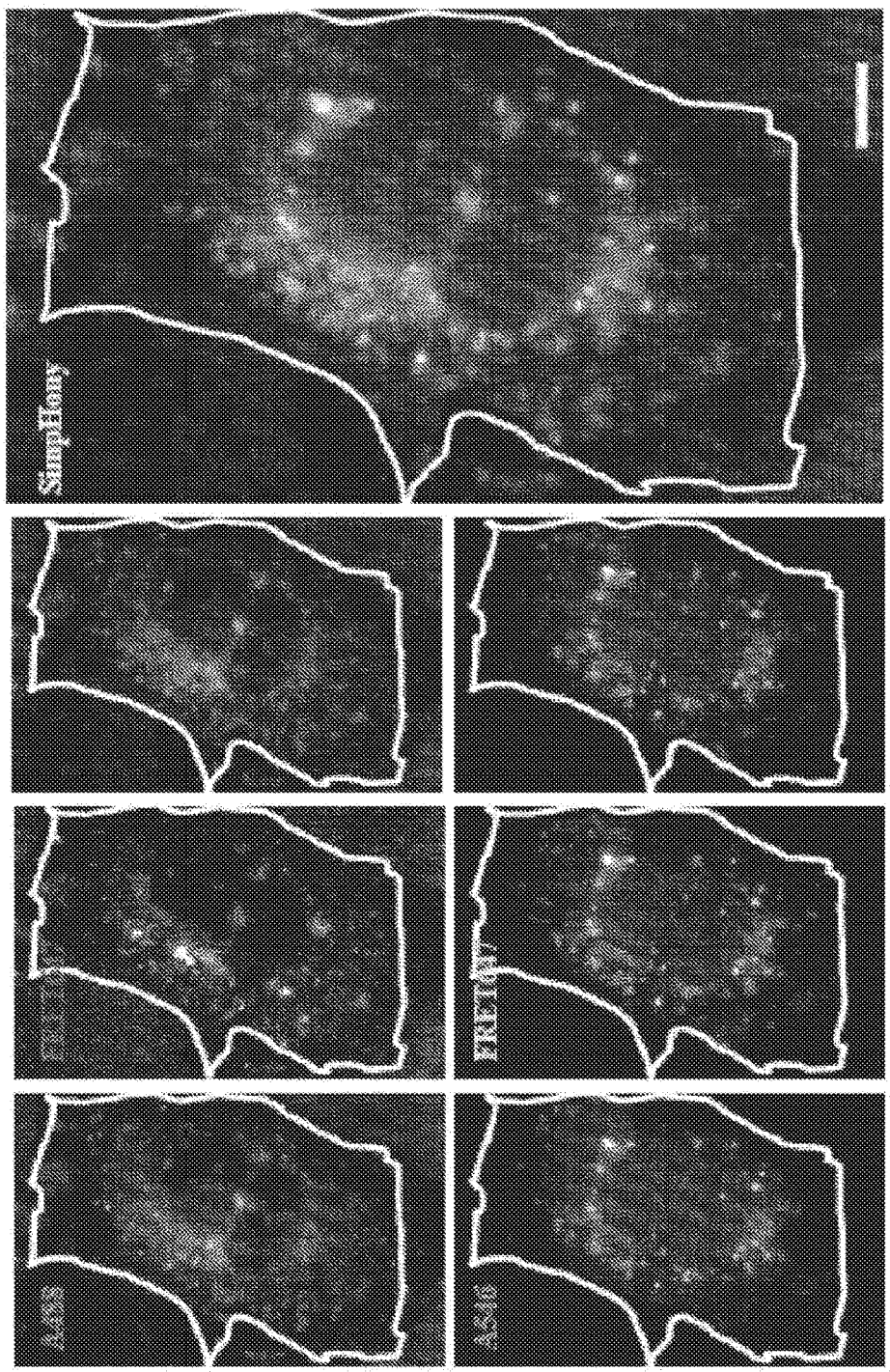

FIG. 16 depicts Simultaneous pH mapping of recycling endosomes and TGN.

Figure 17:
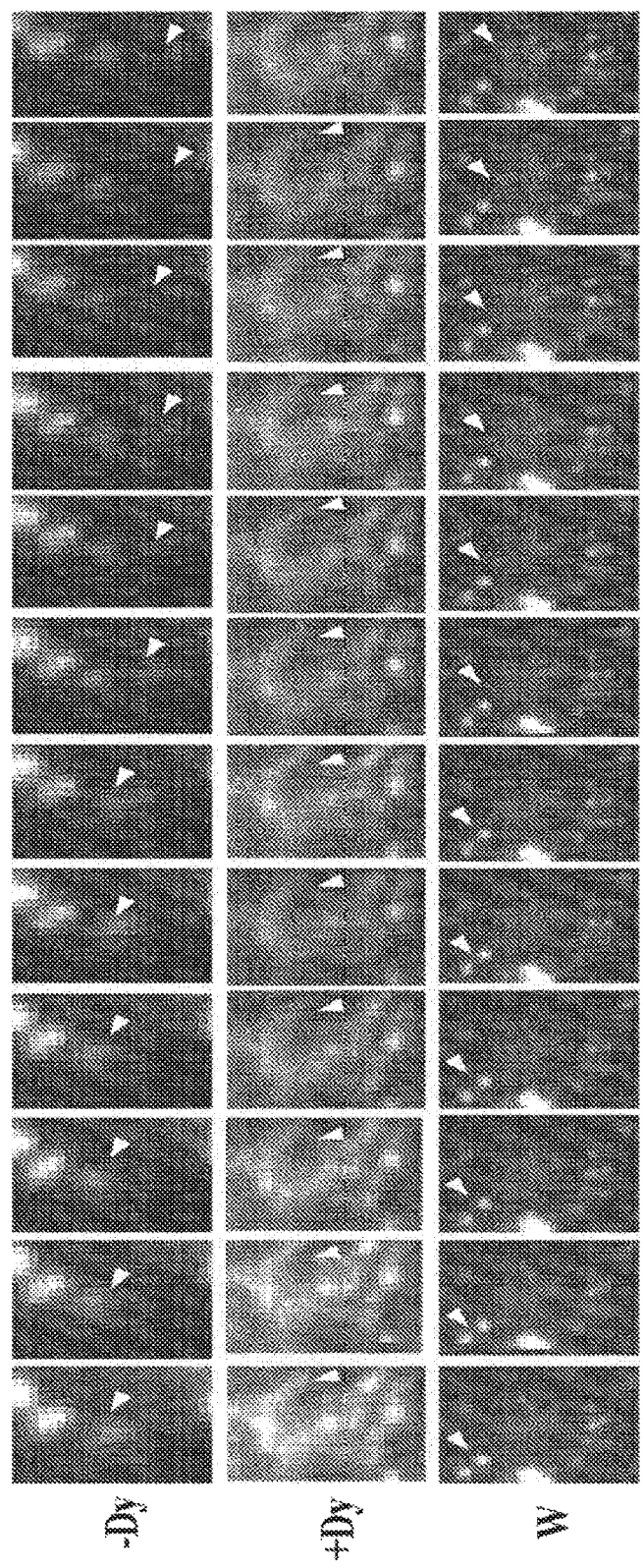

FIG. 17 depicts Dynasore mediated arrest of endosomal fission.

Figure 18:
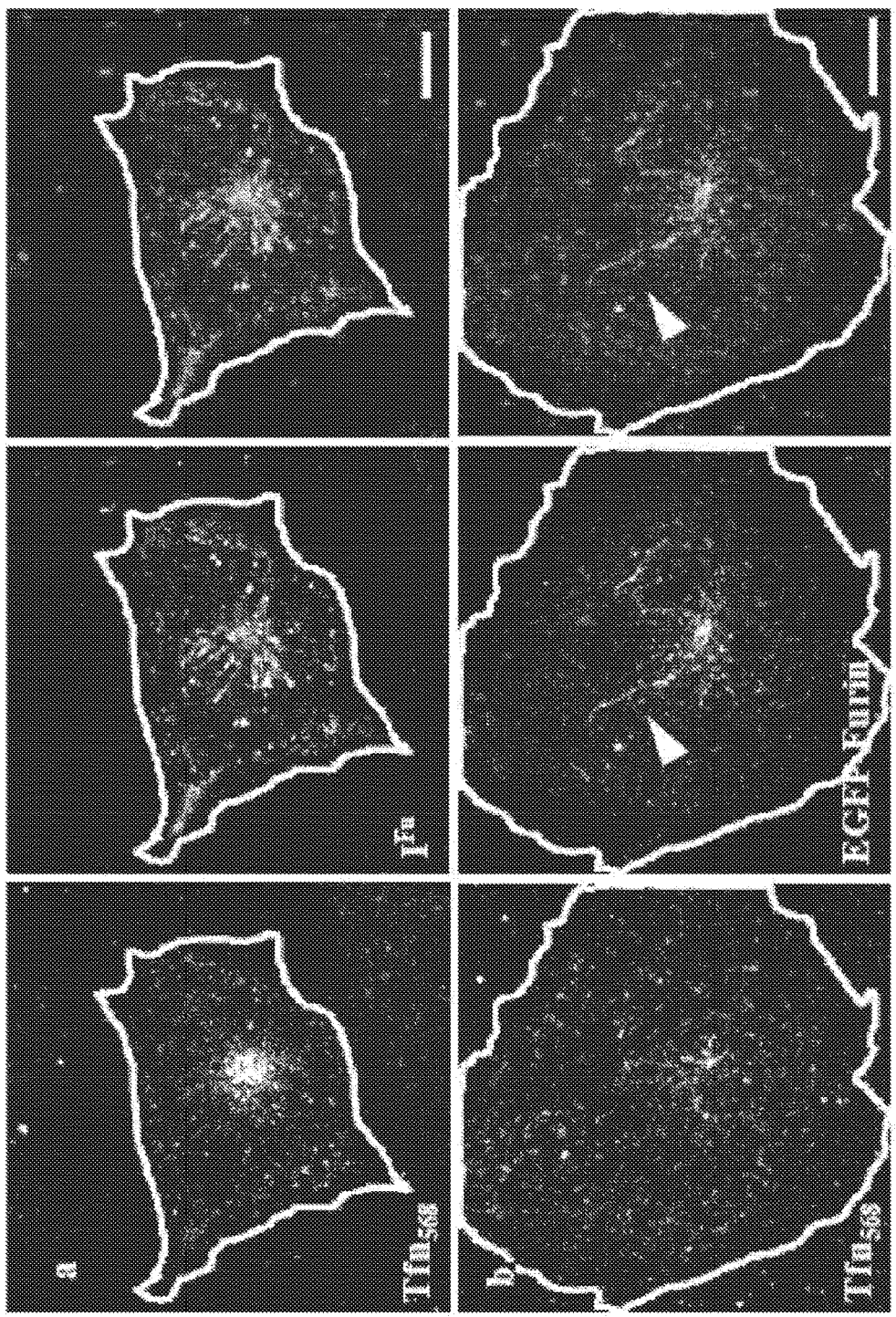

FIG. 18 depicts effect of Brefeldin A on early endosome and TGN.

Figure 19:
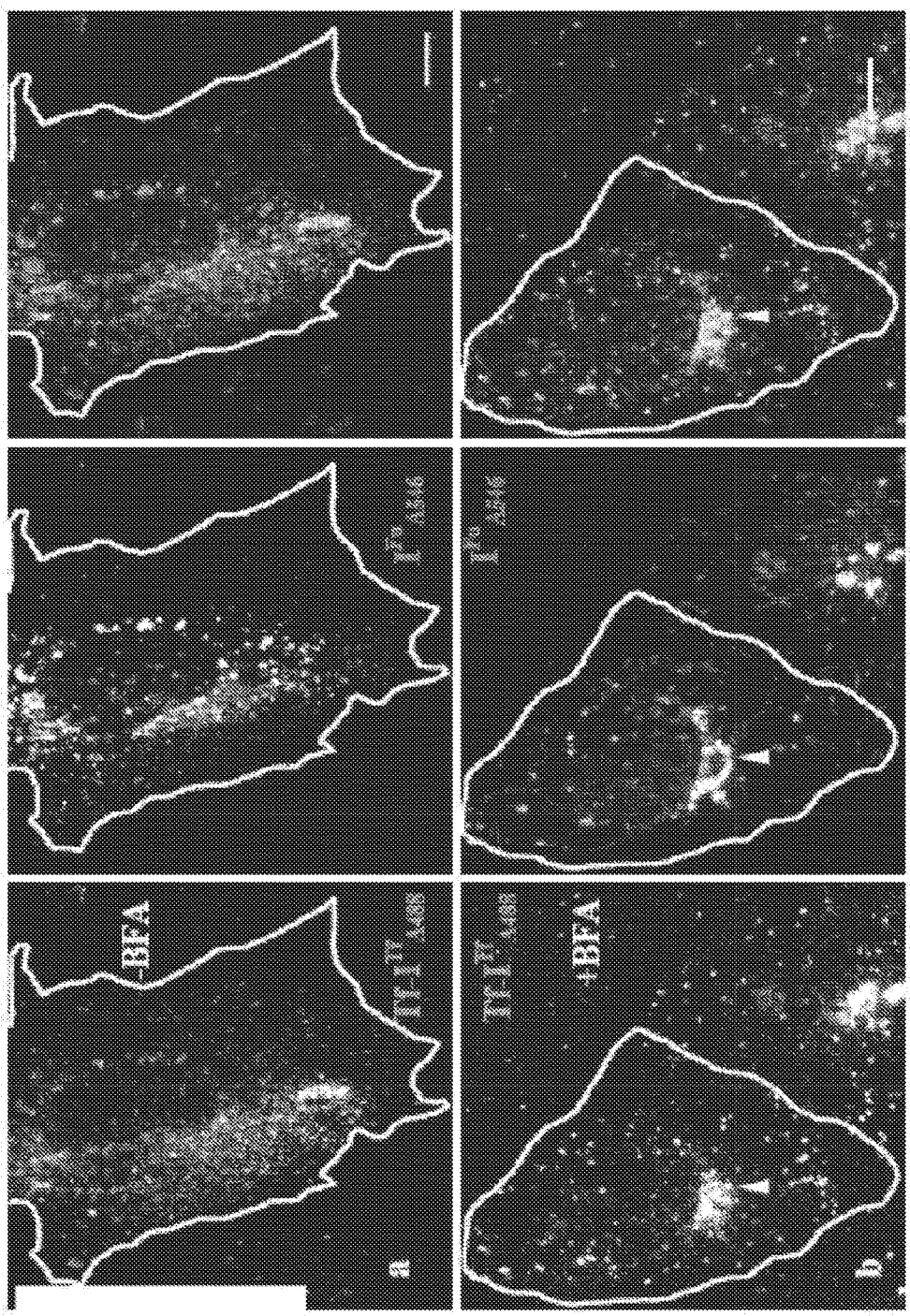

FIG. 19 depicts localization of Tf-$I^{Tf}$ and $I^{Fu}$ DNA sensors in compartments after BFA treatment.

Figure 20:
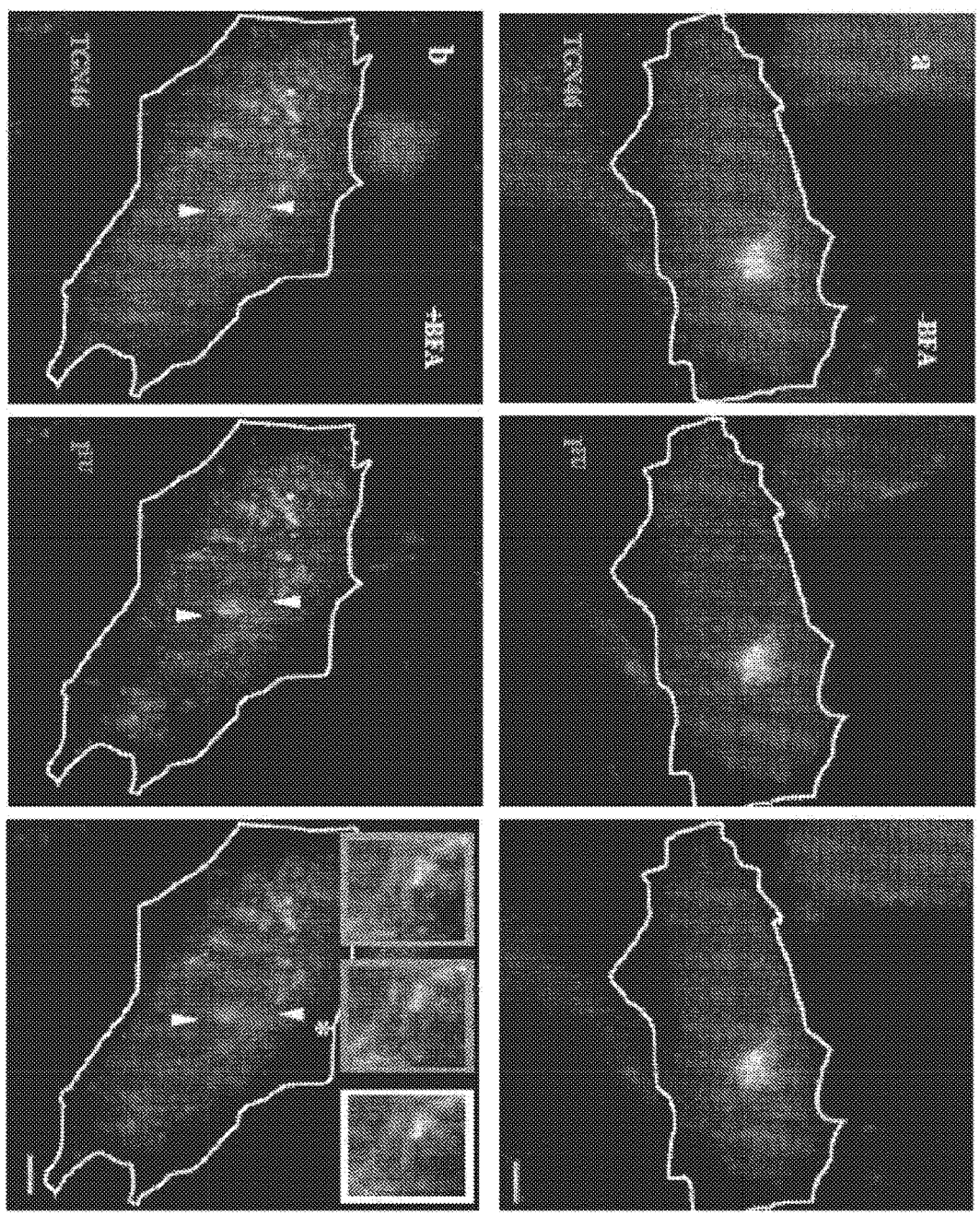

FIG. 20 depicts that DNA sensors redistribute in tubules positive for TGN 46 after BFA treatment.

Figure 21:
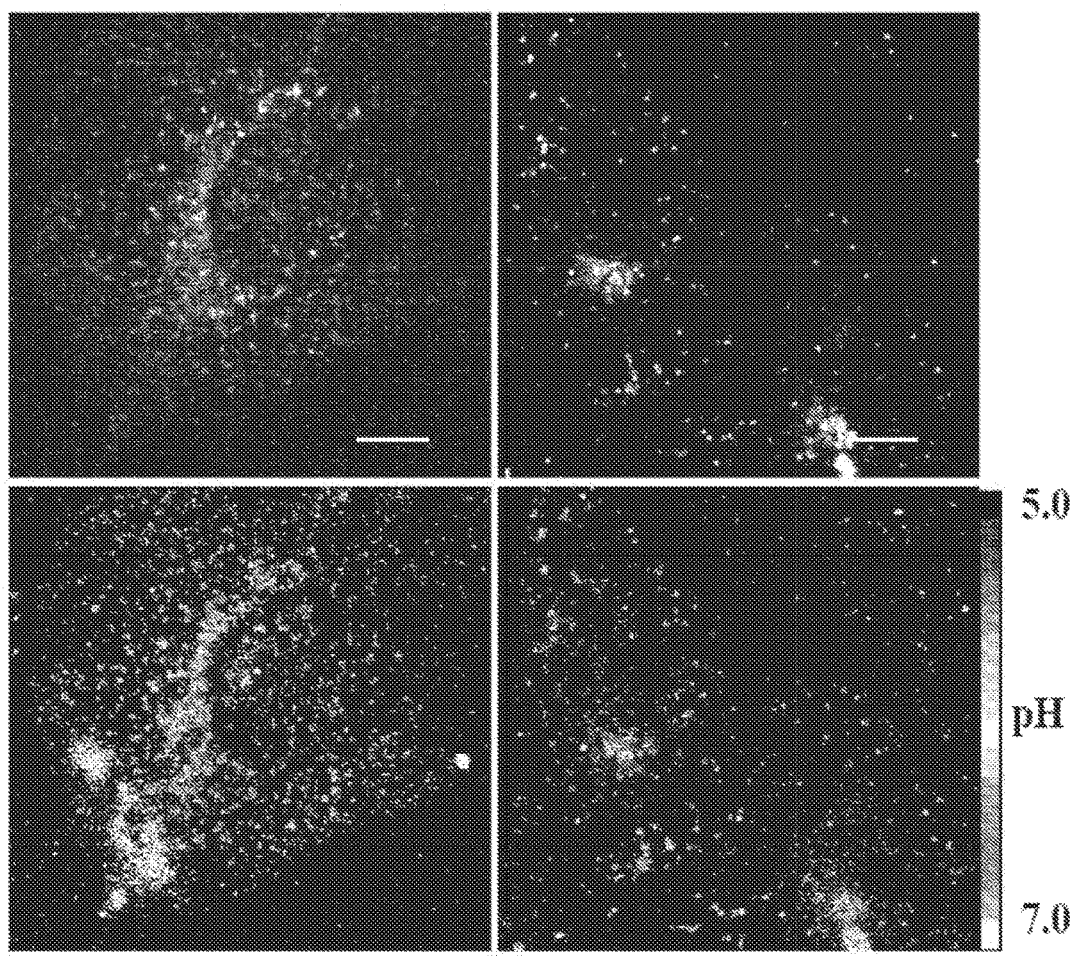

FIG. 21 depicts D/A heat map of cells labelled by Tf-$I^{Tf}_{A488/647}$, post labelling with $I^{Fu}_{A546/A647}$, followed by BFA treatment for about 10 minutes at about 37° C.

Figure 22:
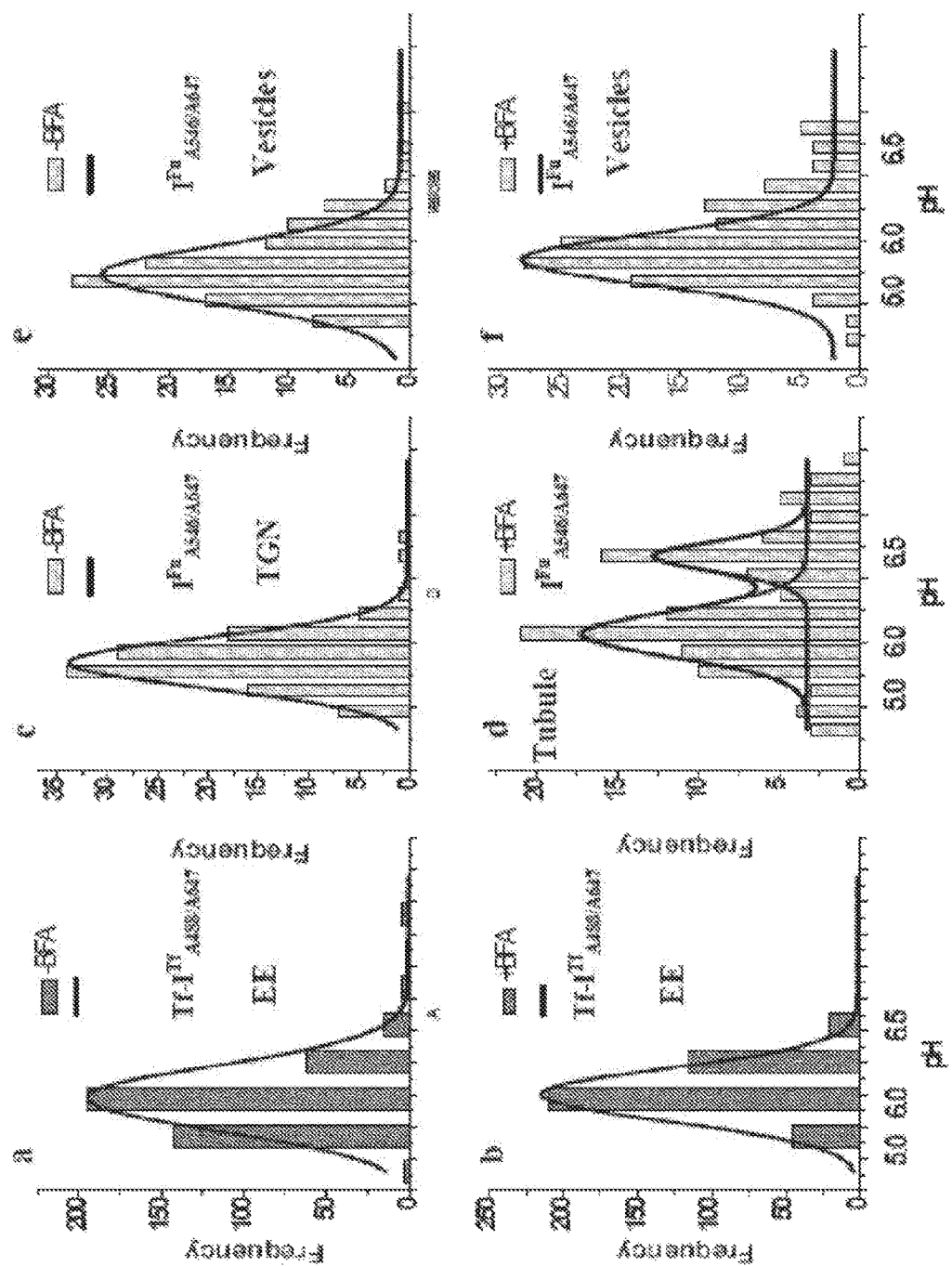

FIG. 22 describes the pH heterogeneity of early endosomes and TGN, pre and post treatment with BFA.

FIG. 23 provides the schematic representations and graphs showing representative fluorescence spectra of $I^{Fu}$ using ALEXA FLUOR®-546 as donor and ALEXA FLUOR®-647 as acceptor.

Figure 24:
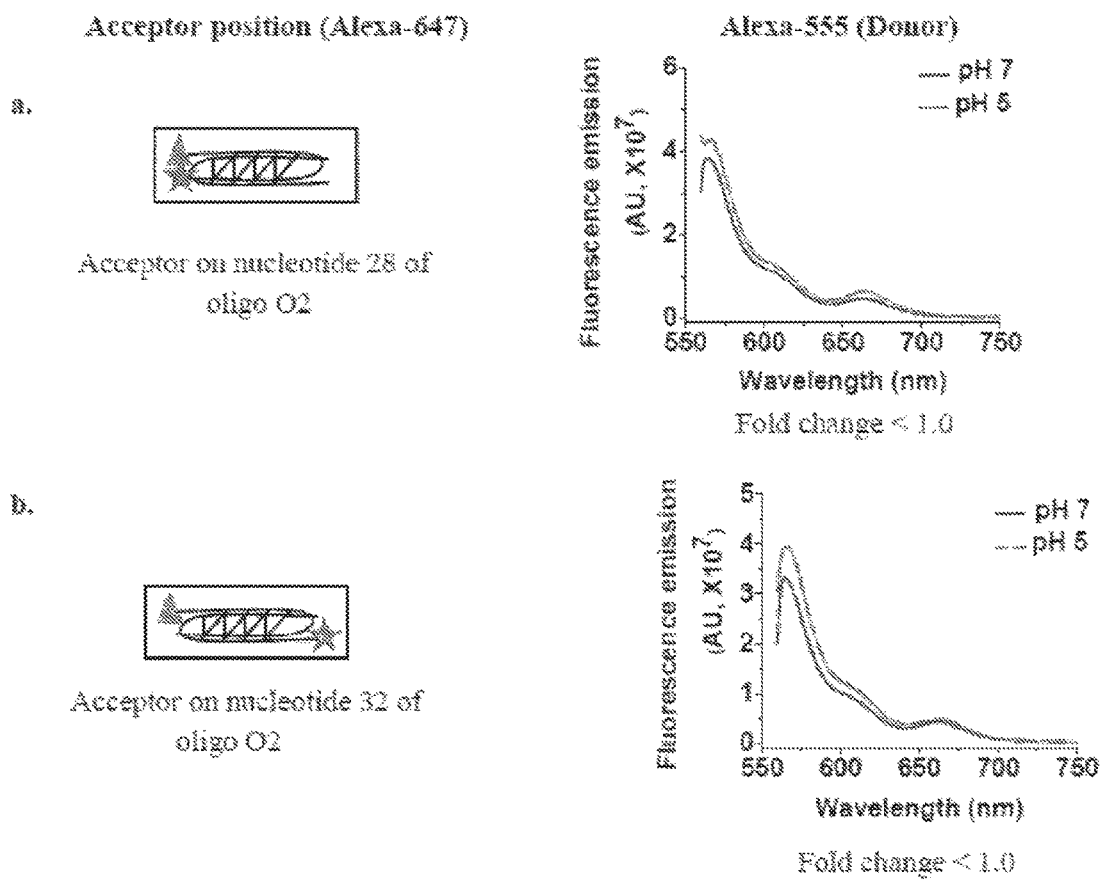

FIG. 24 provides the schematic representation and graphs showing representative fluorescence spectra of $I^{Fu}$ using ALEXA FLUOR®-555 as donor and ALEXA FLUOR®-647 as acceptor.

FIG. 25 provides the schematic representation and graphs showing representative fluorescence spectra of $I^{Fu}$ using Bodipy-TMR as donor and ALEXA FLUOR®-647 as acceptor.

Figure 27:
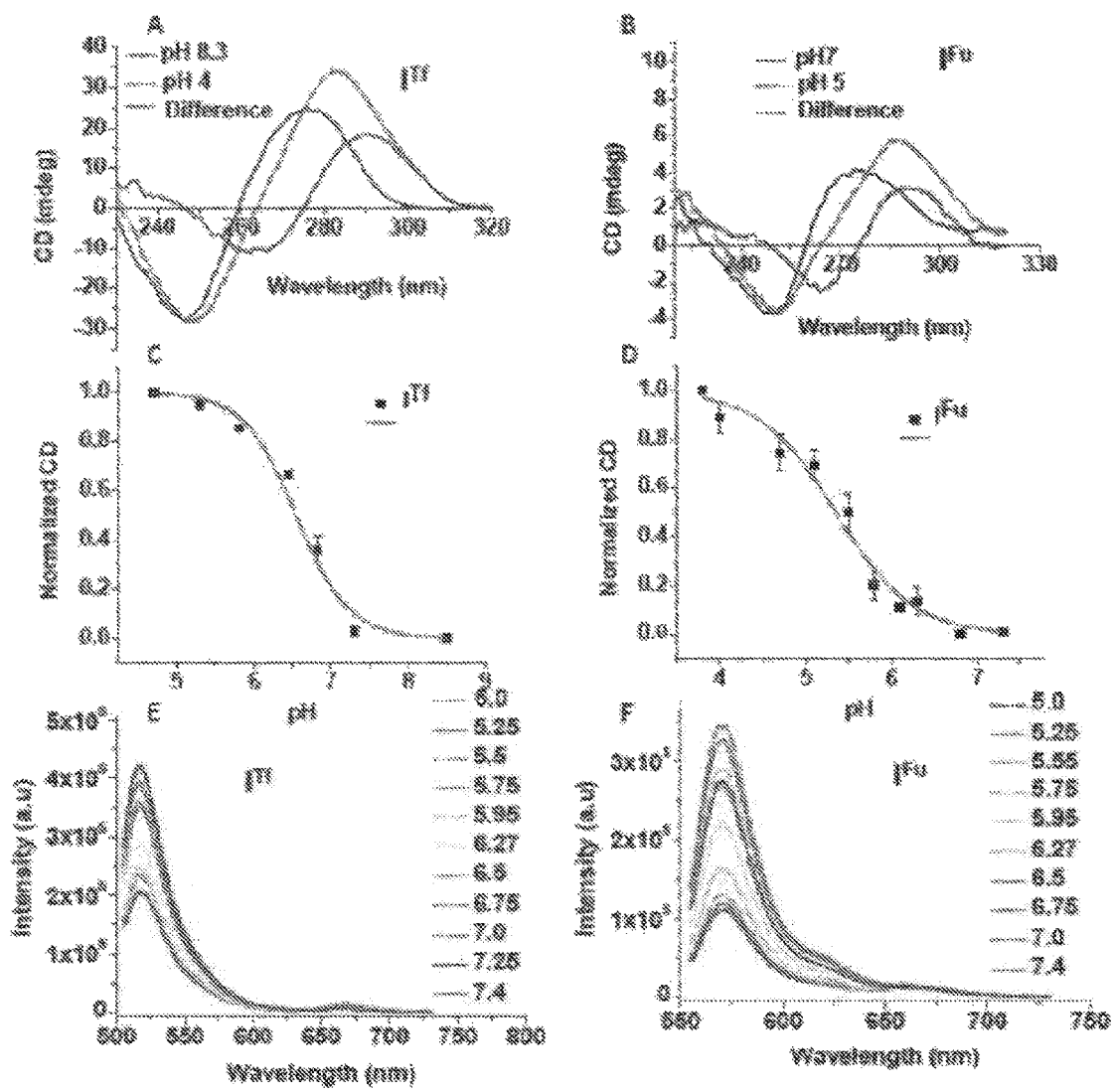

FIG. 26 provides the schematic representation and graphs showing representative fluorescence spectra of $I^{Tf}$ using (A) ALEXA FLUOR®-546 as donor at 5' end of oligo $I^{Tf}$-con 1 and ALEXA FLUOR®-647 as acceptor at nucleotide position 28 of oligo $I^{Tf}$-con 2' (B) ALEXA FLUOR®-555 as donor at 5' end of oligo $I^{Tf}$-con 1 and ALEXA FLUOR®-647 as acceptor at nucleotide position 28 of oligo 2:

FIG. 27 depicts the biophysical characterization of the pH induced structural transition shown by DNA sensors $I^{Fu}$ and $I^{Tf}$.

Figure 28:
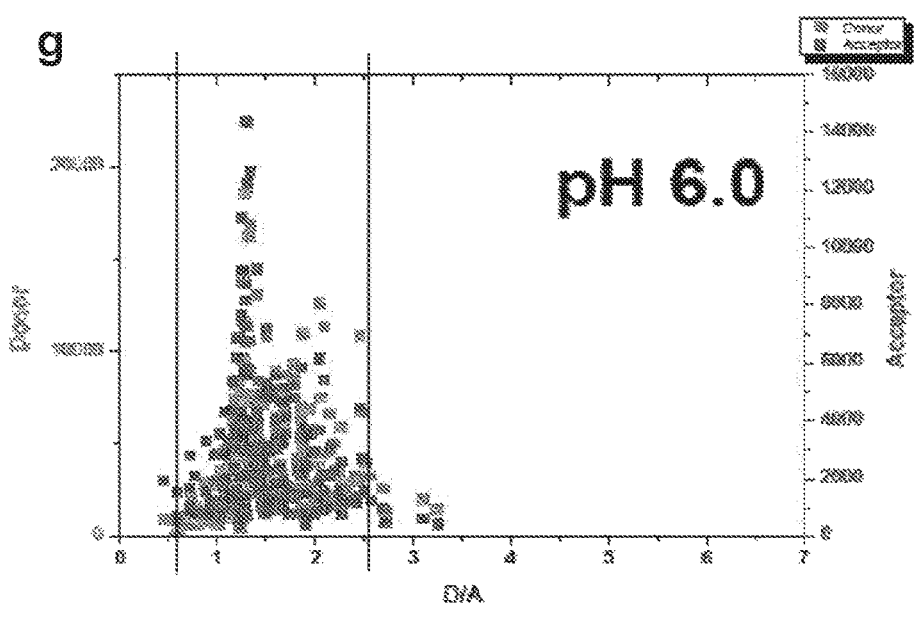

FIG. 28 depicts effect of signal/noise ratio on D/A at different pH values.

Figure 29:
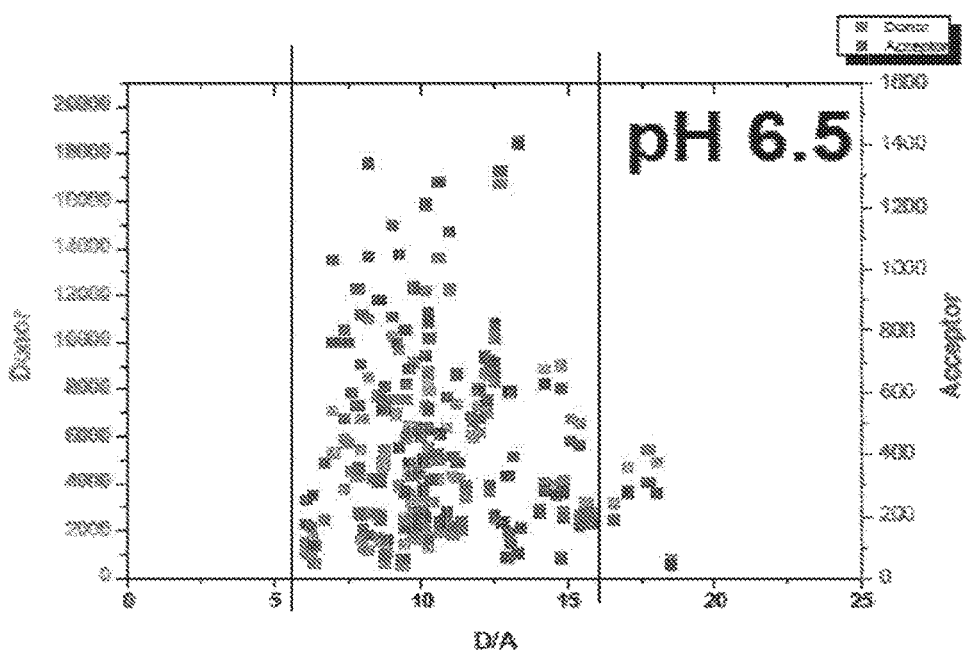

FIG. 29 depicts effect of donor and acceptor intensities on D/A ratio.

DETAILED DESCRIPTION OF THE DISCLOSURE

The present disclosure relates to a method of multiplexing DNA sensors and optionally measuring pH in cell, wherein said DNA sensor comprises Nucleic Acid Assembly and fluorophore, optionally along with protein, said method comprising acts of:
  a) adding the DNA sensors to the cell in labelling media for cellular uptake, to obtain a cell with the DNA sensors;
  b) incubating the cell obtained in step a) in the labelling media for multiplexing the DNA sensors, wherein the DNA sensors are engineered to follow specific cellular pathways within the cell; and
  c) mapping the multiplexed DNA sensors within the cell at time intervals, optionally determining D/A ratio and obtaining calibration curve for measuring pH in the cell.

In an embodiment of the present disclosure, the cellular pathways followed by the DNA sensors are independent; and each of the DNA sensors does not interact with or compromise functionality of another DNA sensor.

In another embodiment of the present disclosure, the cellular pathways are selected from group comprising endocytic pathway and non-endocytic pathway, preferably secretory pathway, transcytosis, nuclear translocation, cell-cell fusion, intracellular fission and fusion phenomena.

In yet another embodiment of the present disclosure, the adding of the DNA sensors to the cell is sequentially or simultaneously; and the cell is selected from group comprising eukaryotic cell, prokaryotic cell and recombinant cell.

In still another embodiment of the present disclosure, the recombinant cell is scFv-Furin expressing cell.

In still another embodiment of the present disclosure, the DNA sensor is engineered to follow specific cellular pathway by conjugating the DNA sensor with specific protein following the cellular pathway; or by expressing chimeric protein on cell with extracellular component recognising the DNA sensor and intracellular component carrying the DNA sensor through the cellular pathway; or by internalization in cell expressing scavenger receptor.

In still another embodiment of the present disclosure, the mapping is by determining position of the DNA sensor at time intervals ranging from about 10 minutes to about 3 hours, using technique selected from group comprising immunofluorescence staining and microscopy technique.

In still another embodiment of the present disclosure, the mapping of the multiplexed DNA sensors optionally comprises adding molecular marker for determining cellular compartment/organelle.

In still another embodiment of the present disclosure, the D/A ratio is obtained by measuring intensity of Donor and Acceptor fluorophore by technique selected from group comprising Fluorescence Resonance Energy Transfer (FRET), Fluorescence Recovery after Photobleaching (FRAP), Fluorescence Loss in Photobleaching (FLIP), Ratiometric Estimation, Fluorescence Lifetime Microscopy, Anisotropy Imaging, Super-Resolution Microscopy method, and Sheet Light Illumination Microscopy.

The present disclosure also relates to a method of localizing DNA sensor comprising Nucleic Acid Assembly and fluorophore, optionally along with protein, in Golgi Network of scFv-Furin expressing cell, said method comprising acts of:

a) adding the DNA sensor to the scFv-Furin expressing cell in labelling media for cellular uptake, to obtain the scFv-Furin expressing cell with the DNA sensor within it;
b) incubating the cell obtained in step a) in the labelling media and adding molecular marker; and
c) determining position of the marker and the DNA sensor within the cell to observe localization of the DNA sensor in the Golgi Network of the scFv-Furin expressing cell.

In an embodiment of the present disclosure, the molecular marker is selected from group comprising NBD-C6-ceramide, anti-TGN46 antibody, antiTGN38 antibody, anti Rabb antibody, Alpha-Mannosidase 2, anti syntaxin 6, VSVG-GFP, TGN RFP and sialyltransferase, preferably NBD-C6-ceramide and anti-TGN46 antibody.

In another embodiment of the present disclosure, the localization of the DNA sensor is observed by microscopy.

In yet another embodiment of the present disclosure, the labelling media comprises components selected from group comprising Dulbecco's Modified Eagle's medium/F-12 (1:1); Ham's F-12 Complete media; M1 Buffer; Fetal Bovine Serum (FBS) at concentration ranging from about 5% to about 15%, preferably about 10%; Streptomycin at concentration ranging from about 50 µg/ml to about 200 µg/ml, preferably about 100 µg/ml; Penicillin at concentration ranging from about 50 I.U./mL to about 200 I.U./mL, preferably about 100 I.U./mL; G418 at concentration ranging from about 50 µg/ml to about 400 µg/ml, preferably about 200 µg/ml; and hygromycin at concentration ranging from about 50 µg/ml to about 200 µg/ml, preferably about 100 µg/ml; or any combinations thereof.

In still another embodiment of the present disclosure, the incubation is carried out for time duration ranging from about 1 minute to about 2 hours; and at temperature ranging from about 0° C. to about 50° C., preferably about 37° C.

The present disclosure also relates to a method of identifying optimal location of fluorophore pair on DNA sensor for multiplexing DNA sensors, wherein the DNA sensor comprises Nucleic Acid Assembly and fluorophore, optionally along with protein, said method comprising acts of:
a) determining spectral overlap between fluorophores and identifying fluorophore pair that displays maximum FRET, wherein the fluorophore pair is for multiplexing of DNA sensors;
b) determining optimal location of the fluorophore pair on Nucleic Acid Assembly of the DNA sensor; and
c) positioning the fluorophore pair on the Nucleic Acid Assembly of the DNA sensor for multiplexing of DNA sensors.

In an embodiment of the present disclosure, the spectral overlap between fluorophores is determined by Fluorescence determining software; and the maximum FRET displayed is identified from the fluorophore pair with maximum fluorescence and minimum cross-talk between the fluorophores.

In another embodiment of the present disclosure, the optimal location of the fluorophore pair on the Nucleic Acid Assembly is determined by technique selected from group comprising molecular modelling, crystal structure and fluorescence spectroscopy.

In yet another embodiment of the present disclosure, the optimal location of the fluorophore pair on Nucleic Acid Assembly of the DNA sensor is determined based on distance between DNA strands of the Nucleic Acid Assembly or distance between the fluorophore pair on the Nucleic Acid Assembly or structure of the Nucleic Acid Assembly or structure of the fluorophore or any combinations thereof.

In still another embodiment of the present disclosure, the distance between the fluorophore pair on the Nucleic Acid Assembly is in the range of about 10 Angstrom to about 100 Angstrom, preferably in the range of about 40 Angstrom to about 60 Angstrom and the fluorophore is positioned on the Nucleic Acid Assembly by covalent chemical conjugation or non-covalent attachment.

In still another embodiment of the present disclosure, the Nucleic Acid Assembly is selected from group comprising natural nucleobase, natural modified base, unnatural modified base, base analog, synthetic derivative of nucleobase and nucleic acid analog or any combinations thereof; the fluorophore is selected from group comprising organic fluorescent dye and inorganic nanomaterial or any combination thereof; and the protein is selected from group comprising Furin, Transferrin, endocytoseable plasma membrane protein, protein that possesses natural receptor, trafficking protein, toxin, virus, viral coat protein, cell penetrating peptide, signal sequence, intracellular targeting sequence, small organic molecule and endocytic ligand or any combinations thereof.

In still another embodiment of the present disclosure, the Nucleic Acid Assembly is selected from sequences comprising SEQ ID Nos. 1 to 14.

In an embodiment, the present disclosure relates to DNA sensors and a method of multiplexing of DNA sensors. The DNA sensors of the present disclosure follow independent cellular pathways, track the same and also measure pH in cell. Various fluorophore pairs are tested to arrive at fluorophore pair with maximum fluorescence and minimum cross-talk. These fluorophore pairs are optimally positioned on DNA sensors of the present disclosure such that the pair is compatible for multiplexing of DNA sensors and separate organelles are mapped in a cell at the same time. Further, the present disclosure relates to a method of localizing DNA sensor in Golgi Network of scFv-Furin expressing cell.

Examples 1.1 to 1.9 of the present disclosure describe various aspects of the preparation of the DNA sensor of the present disclosure, along with their characterization. Further, Examples 2 to 11 of the present disclosure describe the functioning of the DNA sensors of the present disclosure, wherein the localization of DNA sensors in organelles is observed, pH inside organelles is measured and the simultaneous tracking of pathways and measurement of pH by the DNA sensors of the present disclosure inside the same cell is depicted.

Dyes that are used as fluorophore in the methods of the present disclosure include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; ALEXA FLUOR® 350 (Thermo Fisher Scientific, Waltham, Mass.); ALEXA FLUOR® 430; ALEXA FLUOR® 488; ALEXA FLUOR® 532; ALEXA FLUOR® 546; ALEXA FLUOR® 568; ALEXA FLUOR® 594; ALEXA FLUOR® 633; ALEXA FLUOR® 647; ALEXA FLUOR® 660; ALEXA FLUOR® 680; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-CY®7 (GE Healthcare, Chicago, Ill.); APTS; ASTRAZON® Brilliant Red 4G (DyStar, Singapore); ASTRAZON® Orange R; ASTRAZON® Red 6B; ASTRAZON® Yellow 7 GLL; Atabrine; ATTO-TAG™ CBQCA (Thermo Fisher Scientific); ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1 (Thermo Fisher Scientific); BOBO™-3; BODIPY® 492/515 (Thermo Fisher Scientific); BOPDIPY® 493/503; BODIPY® 500/510; BODIPY® 505/515; BODIPY® 530/550; BODIPY® 542/563; BODIPY® 558/568; BODIPY® 564/570; BODIPY® 576/589; BODIPY® 581/591; BODIPY® 630/650-X; BODIPY® 650/665-X; BODIPY® 665/676; BODIPY® FL; BODIPY® FL ATP; BODIPY® Fl-Ceramide; BODIPY® R6G SE; BODIPY® TMR; BODIPY® TMR-X conjugate; BODIPY® TMR-X, SE; BODIPY® TR; BODIPY® TR ATP; BODIPY® TR-X SE; BO-PRO™-1 (Thermo Fisher Scientific); BO-PRO™-3; Brilliant Sulphoflavin FF; Calcein; Calcein Blue; CALCIUM CRIMSON™ (Thermo Fisher Scientific); CALCIUM GREEN™; CALCIUM ORANGE™; Calcofluor White; CASCADE BLUE® (Thermo Fisher Scientific); CASCADE YELLOW®; Catecholamine; CCF2 (GENEBLAZER® (Thermo Fisher Scientific)); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; CY®2; CY®3. 1 8; CY®3.5; CY®3; Cy®5.1 8; CY®5.5; CY®5; CY®7; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM™ 1-43 (Thermo Fisher Scientific); FM™ 4-46; FURA RED™; FURA RED™/Fluo-3 (Thermo Fisher Scientific); Fura-2; Fura-2/BCECF; Genacryl Brilliant Red B; Genacryl Brilliant Yellow 10GF; Genacryl Pink 3G; Genacryl Yellow SGF; GENEBLAZER® (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; LYSOTRACKER® Blue (Thermo Fisher Scientific); LYSOTRACKER® Blue-White; LYSOTRACKER® Green; LYSOTRACKER® Red; LYSOTRACKER® Yellow; LYSOSENSOR™ Blue (Thermo Fisher Scintific); LYSOSENSOR™ Green; LYSOSENSOR™ Yellow/Blue; Mag Green; Magdala Red (Phloxin B); Mag-FURA RED™; Mag-Fura-2; Mag-Fura-5; Mag-Indo-1; MAGNESIUM GREEN™ (Thermo Fisher Scientific); MAGNESIUM ORANGE™ (Thermo Fisher Scientific); Malachite Green; MARINA BLUE® (Thermo Fisher Scientific); MAXILON® Brilliant Flavin 10 GFF (Huntsman, The Woodlands, Tex.); MAXILON® Brilliant Flavin 8 GFF; Merocyanin; Methoxycoumarin; MITOTRACKER® Green FM (Thermo Fisher Scientific); MITOTRACKER® Orange; MITOTRACKER® Red; Mitramycin; Monobromobimane; Monobromobimane (mBBr-GSH); Monochlorobimane; MPS (Methyl Green Pyronine Stilbene); NBD; NBD Amine; Nile Red; NED™ (Thermo Fisher Scientific); Nitrobenzoxadidole; Noradrenaline; Nuclear Fast Red; Nuclear Yellow; NYLOSAN® Brilliant Flavin E8G (Archroma, Reinach, Switzerland); OREGON GREEN® (Thermo Fisher Scientific); OREGON GREEN® 488-X; OREGON GREEN®; OREGON GREEN® 488; OREGON GREEN® 500; OREGON GREEN® 514; PACIFIC BLUE® (Thermo Fisher Scientific); Pararosaniline (Feulgen); PBFI; PE-CY®5; PE-CY®7; PerCP; PerCP-CY®5.5; PE-TEXAS RED® [Red 613] (Thermo Fisher Scientific); Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO™-1 (Thermo Fisher Scientific); POPO™-3; PO-PRO™-1 (Thermo Fisher Scientific); PO-PRO™-3; Primuline; PROCION® Yellow (DyStar); Propidium Iodide (PI); PyMPO; Pyrene; Pyronine; Pyronine B; Pyrozal Brilliant Flavin 7GF; QSY 7; Quinacrine Mustard; Red 613 [PE-TEXAS RED®]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; SEVRON® Brilliant Red 2B (DuPont, Wilmington, Del.); SEVRON® Brilliant Red 4G; SEVRON® Brilliant Red B; SEVRON® Orange; SEVRON® Yellow L; SGBFP™ (super glow BFP, MP Biomedicals, Burlingame, Calif.)); SGGFP™ (super glow GFP); SITS; SITS (Primuline); SITS (Stilbene Isothiosulphonic Acid); SNAFL calcein; SNAFL-1; SNAFL-2; SNARF® calcein (Thermo Fisher Scientific); SNARF®-1; SODIUM GREEN™ (Thermo Fisher Scientific); SPECTRUMAQUA™ (Abbott Laboratories, Chicago, Ill.); SPECTRUMGREEN™ (Abbott Laboratories); SPECTRUMORANGE™ (Abbott Laboratories); SPECTRUMRED™ (Abbott Laboratories); SPQ (6-methoxy-N-(3-sulfopropyl) quinolinium); Stilbene; Sulphorhodamine B can C; Sulphorhodamine G Extra; SYTO® 11 (Thermo Fisher Scientific); SYTO® 12; SYTO® 13; SYTO® 14; SYTO® 15; SYTO® 16; SYTO® 17; SYTO® 18; SYTO® 20; SYTO® 21; SYTO® 22; SYTO® 23; SYTO® 24; SYTO® 25; SYTO® 40; SYTO® 41; SYTO® 42; SYTO® 43; SYTO® 44; SYTO® 45; SYTO® 59; SYTO® 60; SYTO® 61; SYTO®

62; SYTO® 63; SYTO® 64; SYTO® 80; SYTO® 81; SYTO® 82; SYTO® 83; SYTO® 84; SYTO® 85; SYTOX® Blue (Thermo Fisher Scientific); SYTOX® Green; SYTOX® Orange; TET™ (Thermo Fisher Scientific); Tetracycline; Tetramethylrhodamine (TRITC); TEXAS RED®; TEXAS RED®-X conjugate; Thiadicarbocyanine (DiSC3); Thiazine Red R; Thiazole Orange; Thioflavin 5; Thioflavin S; Thioflavin TCN; THIOLYTE® (Sigma Aldrich, St. Louis, Mo.); TINOPAL® CBS (Calcofluor White, BASF, Florham Park, N.J.)); TMR; TO-PRO®-1 (Thermo Fisher Scientific); TO-PRO®-3; TO-PRO®-5; TOTO®-1 (Thermo Fisher Scientific); TOTO®-3; TRI-COLOR® (PE-Cy5, Thermo Fisher Scientific); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO®-1 (Thermo Fisher Scientific); YO-PRO®-3; YOYO®-1 (Thermo Fisher Scientific); YOYO®-3; and salts thereof.

In an embodiment of the present disclosure, Microscopic methods include Super-Resolution Microscopy Methods used for determining D/A ratio for DNA sensors, such as SIM, STED, STORM, PALM and HILO.

In another embodiment of the present disclosure, the spectral overlap between fluorophores is determined by Fluorescence determining software such as SpectraViewer, Fluorescence Spectrum Viewer, FluorPlan Spectra Viewer and BioLegend Spectra Analyzer.

In an embodiment of the present disclosure, the incubation of the cell for multiplexing DNA sensors and for localizing DNA sensor is carried out preferably for 2 hours for $I^{Fu}$ DNA Sensor and preferably for 10 minutes for $I^{Tf}$ DNA Sensor.

In an embodiment of the present disclosure, mapping of the DNA sensors is by determining position of the DNA sensor using microscopy techniques such as Optical Microscopy, Immuno-Electron Microscopy techniques such as Immuno-gold labelling, Singlet Oxygen Generator technology as applied to Electron Microscopy and correlative microscopy techniques.

In an embodiment of the present disclosure, DNA sensor of the present disclosure follows non-endocytic pathways as observed in pH measurement of TGN and Brefeldin A mediated tabulation.

In an embodiment of the present disclosure, a cellular compartment and an organelle are used interchangeably for each other and have the same meaning and scope with respect to the present disclosure.

In a preferred embodiment of the present disclosure, the Nucleic Acid Assembly of the DNA Sensor is a natural nucleobase.

In another embodiment of the present disclosure, the Nucleic Acid Assembly is a natural modified base selected from group comprising 6-keto purine, xanthine, 5-methylcytosine and 2-aminopurine.

In embodiments of the present disclosure, the Nucleic Acid Assembly is an unnatural modified base selected from group comprising thioguanine, 8-oxoguanine, deazapurine and azapurine; a base analog selected from group comprising nebularin, nitroindole and nitropyrrole derivative; a synthetic derivative of nucleobase selected from group comprising bromo substituted derivative and fluoro substituted derivative and a nucleic acid analog selected from group comprising Peptide Nucleic acid (PNA), Locked Nucleic Acid (LNA), morpholino, methyl phosphonate, phosphorothioate and 2'-O-modified oligonucleotide.

In an embodiment of the present disclosure, the fluorophore of the DNA Sensor optionally comprises fluorescent acceptor dye that quenches a fluorescent signal from a fluorescent donor dye.

In an embodiment of the present disclosure, the fluorophore includes fluorescent dye or its derivative. The fluorophore also includes amine-reactive derivatives like isothiocyanate derivatives and/or succinimidyl ester derivatives of all commercially available fluorophores e.g. ALEXA FLUOR® dyes, ATTO™ dyes, CY®-5 dyes and DYLIGHT® (Thermo Fisher Scientific) series dyes along with fluorescein derivatives and amino purines.

In an embodiment of the present disclosure, the fluorophore pair positioned on DNA sensor is composed of donor fluorophore and acceptor fluorophore.

In an embodiment of the present disclosure, the fluorophore pair is composed of organic fluorescent dye and quantum dot, organic fluorescent dye and organic fluorescent dye; or quantum dot and quantum dot.

Quantum dots are similar to fluorescent dyes. These are inorganic nanoparticles that emit light upon excitation by light. Quantum dots are directly coupled to DNA strands used in this application.

In an embodiment of the present disclosure, the spectral pattern of the fluorophore is determined using Fluorescence SpectraViewer software available from Life technologies. After this, dyes are selected based on 3 major criteria:
1) Maximum overlap between donor emission and acceptor excitation spectra.
2) Minimum direct excitation of acceptor upon donor excitation.
3) Minimum bleed-through of Donor emission in the acceptor emission channel.

In an embodiment, cell employed in the method of the present disclosure is plant cell, mammalian cell, fly cell or yeast cell.

In a preferable embodiment of the present disclosure, the cell used in the methods is HeLa cell or CHO cell or NIH3T3 cell or HepG2 or cell lines derived from any of them.

In an embodiment of the present disclosure, the cell is a HeLa cell. In another embodiment, the cell is an IA2.2 cell.

In an embodiment of the present disclosure, SimpHony (Simultaneous pH mapping technique) is applied to two separate cases where perturbation of organelle morphology reveals its altered lumenal acidity. This coupling between physical organization of compartments with their internal chemical environment connects onwards to protein trafficking.

The non-interfering nature, robust performance and functionality in tandem of autonomous programmable DNA sensors positions them as powerful tools to tease apart complex intracellular trafficking events, where proton dynamics impact biological phenomena such as organelle fission/fusion across sorting pathways or in cell-cell communication.

In different organisms, proton gradient across cells determines different cell fates. In an embodiment, this type of cell to cell communication in terms of proton gradient is captured by the method of labelling two different cell types by two different DNA sensors.

In an embodiment of the present disclosure, the functionality of two differently programmed DNA sensors is described, each transported along a different cellular endocytic pathway, where they map pH changes along both pathways simultaneously, within the same living cell.

Functionalization of protein/peptide ligands with pH-sensitive fluorophores also alters the physicochemical properties of the fluorophore per se. However, in the DNA sensing technology of the present disclosure, the fluorophore environment in the sensor remains unchanged, allowing for high reproducibility and low errors in measurements, allowing one to capture even subtle variations in pH with greater clarity.

In an embodiment of the present disclosure, the maximum FRET of the fluorophore pair, determined by fold change between open and close state, is 4.5 for $Tf\text{-}I^{Tf}_{A488/A647}$ and 3.1 for $I^{Fu}_{A546/647}$.

The present disclosure is further elaborated with the help of following examples and associated figures. However, these examples should not be construed to limit the scope of the present disclosure.

EXAMPLES

Example 1.1: Preparation of DNA Sensors

This experiment is used to provide the Nucleic Acid Assemblies of the DNA sensors of the present disclosure.

TABLE 1

| Sequence Id No. | Sequence Name | Sequence |
|---|---|---|
| 1 | $I^{Fu}_{A488}$ | 5'-Alexa488-CCCCTAACCCCTAACCCCTAACCCCATATATATCCTAGAACGACAGACAAACAGTGAGTC-3' |
| 2 | $I^{Fu'}_{A647}$ | 5'-GACTCACTGTTTGTCTGTCGTTCTAGGA<u>T</u>ATATAT<u>TTT</u>GTTATGTGTTATGTGTTAT-3'  (Alexa647) |
| 3 | Tf-con 1 | 5'- Alexa 488--CCC CTA ACC CCT AAC CCC TAA CCC CTT TAA ATA GGC ACC GGC ATG CGC AGT CTG ACG T |
| 4 | Tf-con 2' | 5'-Thiol--ACG TCA GAC TGC GCA TGC CGG TGC CTA <u>TTT AAA TTT GTT</u> ATG TGT TAT GTG TTA T---3'  (Alexa 647) |
| 5 | O2-647 loop-27 | 5'-CCGACCGCAGGATCCTATAAAACCCC<u>A</u>ACCCC-3'  (Alexa 647) |
| 6 | O1-546 Cell | 5'-Alexa-546-5'--CCCCAACCCCAATACATTTATATATATCCTAG-3' |
| 7 | O3-cell | 5'---TTATAGGATCCTGCGGTCGGACTAGGATATATATAAATGTA---3' |
| 8 | SsDNA | 5'-Biotin-AAAAGACTCACTGTTTGTCTGTCGTTCTAGGATATATAT-3' |
| 9 | ssDNA' | 5'-ATATATATCCTAGAACGACAGACAAACAGTGAGTC-3' |
| 10 | Region 1 | 5'-ATATATATCCTAG-3' |
| 11 | Region 2 | 5'-CGACAGACAAACA-3' |
| 12 | Region M | 5'-CCTAGAACGACAG-3' |
| 13 | $I^{comp}$ | 5'-ATATATATCCTAGAACGACAGACAAACAGTGAGTCCGCATTGTTACAT-3' |
| 14 | $I^{comp'}$ | 5'-ATGTAACAATGCGGACTCACTGTTTGTCTGTCGTTCTAGGATATATAT-3' |

Table 1: This table describes the sequences used and associated nomenclature of samples in the present disclosure. Nucleic acid assemblies incorporating a pH responsive segment Cn—Cn—Cn—Cn are referred to as I″ when they carry no fluorescent labels. Fluorescently labelled Nucleic Acid Assemblies indicate the respective fluorophore in the subscript. The 35 bp dsDNA epitope is formed from ssDNA and ssDNA', $R_1$: ssDNA and Region 1, $R_2$: ssDNA and Region 2, $R_M$: ssDNA and Region M.

$I^{comp}$:$I^{comp}$ and $I^{comp'}$ and $I^{non\ comp}$:$I^{non\ comp}$ and $I^{non\ comp'}$; $I^{Tf}$: Tfcon1 and Tf con2', and $I^{Fu}$: O2-647-loop-27, O1-546 Cell and O3 cell. $I^{Fu}$ 488 and $I^{Fu'}$647 are used to prepare $I^{Fu}$ sensor that tracks Furin pathway in an embodiment of the present disclosure.

In an embodiment of the present disclosure, Tf-con 1 and Tf con 2' are used to prepare $I^{Tf}$. About 50 µM of 1:1 mixture of Tf-con 1 and Tf con 2' is annealed in 1×PBS, at a pH of about 7.4, in presence of about 50-100 mM of Dithiothreitol (DTT), incubated overnight and then used for conjugation with Tf conjugated SPDP (N-succinimidyl-3-(2-pyridyldithio) propionate).

In an embodiment of the present disclosure, (Tf-$I^{Tf}_{(A488/A647)}$) is made up of oligos Tf-con 1 and Tf con 2' conjugated to Transferrin. These oligos are used for pH measurements of Early/Sorting Endosome (EE/SE) and Recycling Endosomes as well as for co-localization analysis.

In an embodiment of the present disclosure, O1-546 Cell, O2-647-loop-27, O3-cell are used to prepare $I^{Fu}$. About 5 mM of each O1-546 Cell, O2-647-loop-27, O3-cell are mixed in about 20 mM potassium phosphate buffer, at a pH of about 5.5 and annealed. About 24 hours post incubation, this mixture is directly added to cells expressing scFv-furin. In an embodiment of the present disclosure, ($I^{Fu}_{(A546/A647)}$) is made up of oligos O1-546 Cell, O2-647-loop-27 and O3-cell. These oligos are used for pH measurements of EE/SE, Late Endosomes and Trans-Golgi network.

In another embodiment of the present disclosure, $I^{Fu}_{A488}$ and $I^{Fu}_{A647}$ are variants of $I^{Fu}$ ($I^{Fu}_{(A488/A647)}$) and after annealing as described above, it forms $I^{Fu}$ (labelled with ALEXA FLUOR® 488 and 647). This combination is used for multiplexing of DNA sensors and for co-localization analysis where secondary antibody/molecular marker is labelled with ALEXA FLUOR®546.

In an embodiment of the present disclosure, the sequences that are used as Nucleic acid assemblies comprise sequences having SEQ ID Nos. 1-14.

Example 1.2: Programming Strategy to Achieve Simultaneous pH Mapping

Simultaneous mapping of an analyte such as pH using Fluorescence Resonance Energy Transfer (FRET) based DNA sensors requires—
(i) a combination of FRET pairs with minimal crosstalk,
(ii) molecular programming strategies that position the DNA sensors along two different pathways and
(iii) "SimpHony" or simultaneous pH mapping technology, which requires two pH responsive DNA sensors comprising Nucleic Acid Assemblies with pH sensitive regimes suited to the lumenal pH of the relevant intracellular organelles being investigated.

In an embodiment of the present disclosure, in order to enable SimpHony, two well-characterised pathways are chosen, namely:
(i) the transferrin endocytic/recycling pathway and
(ii) the furin retrograde endocytic pathway.

Transferrin binds the transferrin receptor at the plasma membrane, reaches the sorting endosome. Cargos are then sorted from here and transferrin accumulates near the perinuclear recycling endosome from where it recycles back to the plasma membrane. Furin is a type-I membrane protein which resides predominantly in the trans-Golgi network (TGN) with a small steady state population at the plasma membrane. It is transported retrogradely via the sorting and late endosomes enroute to the TGN.

The transferrin and furin pathways merge in the early endosome and then segregate thereafter into the recycling and late endosomes, respectively.

Transferrin→Sorting Endosome Recycling Endosome→Plasma Membrane.

Furin→Sorting Endosome→Late Endosomes→Trans Golgi Network

Transferrin Pathway

To track the transferrin pathway, a two-stranded pH-sensitive DNA sensor, $I^{Tf}$ (FIG. 1a) is engineered. $I^{Tf}$ uses intra-strand I-motif formation to undergo a pH dependent conformational change and therefore functions as a FRET based pH sensor. One of the strands in $I^{Tf}$ possesses a pH responsive C-rich segment, shown in purple (FIG. 1a). This domain partially base pairs with a G-rich overhang in the complementary strand to form a mismatched duplex engineered to have low stability. At low pH, this mismatched duplex frays, allowing the C-rich strand to fold into an intramolecular I-motif.

By chemically conjugating transferrin (Tf) to one of the strands in $I^{Tf}$ to give Tf-$I^{Tf}$ (transferrin conjugated to $I^{Tf}$), $I^{Tf}$ is molecularly programmed to be confined along the transferrin receptor pathway.

Furin Pathway

In order to track the furin pathway, a second molecularly programmed DNA sensor called $I^{Fu}$ is used (FIG. 1A). It adopts an isosceles triangle like formation upon lowering of the pH. In the process:
(i) the position of the acceptor—27th base from 5' end of O2-Cell-647 is optimized to maximize the observed FRET;
(ii) the FRET pair uses ALEXA FLUOR® 546 as a donor fluorophore, which allows compatibility of $I^{Fu}$ pH measurements in the presence of $I^{Tf}$ fluorophores; and
(iii) the DNA assembly incorporates an 8 base-pair dsDNA sequence (shown in gray in FIG. 1A) that functions as a binding site for an engineered protein (gray cylinders shown in FIG. 1A) that enables the localization of the sensor to a specific endocytic pathway, namely furin.

Since furin is a retrogradely transported membrane protein and lacks a natural ligand, a method to specifically attach and transport a DNA sensor comprising Nucleic Acid Assembly to a given trafficking protein is developed. This method uses a sequence specific dsDNA binding protein (single chain variable fragment recombinant antibody or scFv) that is expressed as a chimera with furin, where the scFv domain acts as an artificial receptor for a DNA sensor comprising Nucleic Acid Assembly that possesses the requisite dsDNA sequence. This sequence specific, dsDNA—binding protein is obtained from a phage display screen of recombinant antibodies against a dsDNA epitope.

When the chimeric scFv-furin is expressed in the cell, the 8 bp domain of the Nucleic Acid Assembly of the DNA sensor binds to the extracellular scFv domain of the chimeric scFv-Furin protein population present on the plasma membrane and is trafficked along the retrograde furin endocytic pathway into the TGN (FIG. 1B).

Example 1.3: Selection of scFvs Binding Sequence-Specifically to a DNA Tag

This experiment is performed to find DNA binding recombinant antibodies. A specific scFv is screened against the DNA sensor's handle domain. The Tomlinson I+J scFv library (from Geneservice, now available from Source BioScience) is screened by phage display against a biotinylated 35 bp dsDNA tag according to conditions described for the selection of anti-GTPase scFvs. Out of 96 randomly picked clones after 3 rounds of selection, about 60 clones binding specifically to the DNA tag are identified by ELISA. DNA sequencing of positive clones allows redundancy to be eliminated, yielding 29 distinct positive clones. scFvs are screened for region specific binding, selectively binding against three different epitopes.

The 35 bp dsDNA is divided into three regions:
 (i) One region is composed of 13 bp of the antigen from the 3' end (known as Region 1 ($R_1$), FIG. 6a, red),
 (ii) the second region corresponds to base pairs 16 to 28 from 3' end (Region 2 ($R_2$), FIG. 6a, green) and
 (iii) the third region is an overlap of regions 1 and 2 (Region M ($R_M$), FIG. 6a, blue).

These three duplexes are annealed and then immobilized on three different 96-well plates. scFv supernatant of the same clones is added to the wells and incubated as described earlier. It is observed that most of the clones are specific for $R_1$ (FIG. 6B(i)), in that they do not bind $R_2$ (FIG. 6B(ii)) or $R_M$ (FIG. 6B(iii)). For example, clones C1, D1, E1, G1 and H1 are distinct from each other, binding to $R_1$ and no other region. Thus, the scFvs corresponding to these clones recognize only the first 8 base pairs of the 35 bp dsDNA i.e., the sequence $d(AT)_4$.

Figure 6:
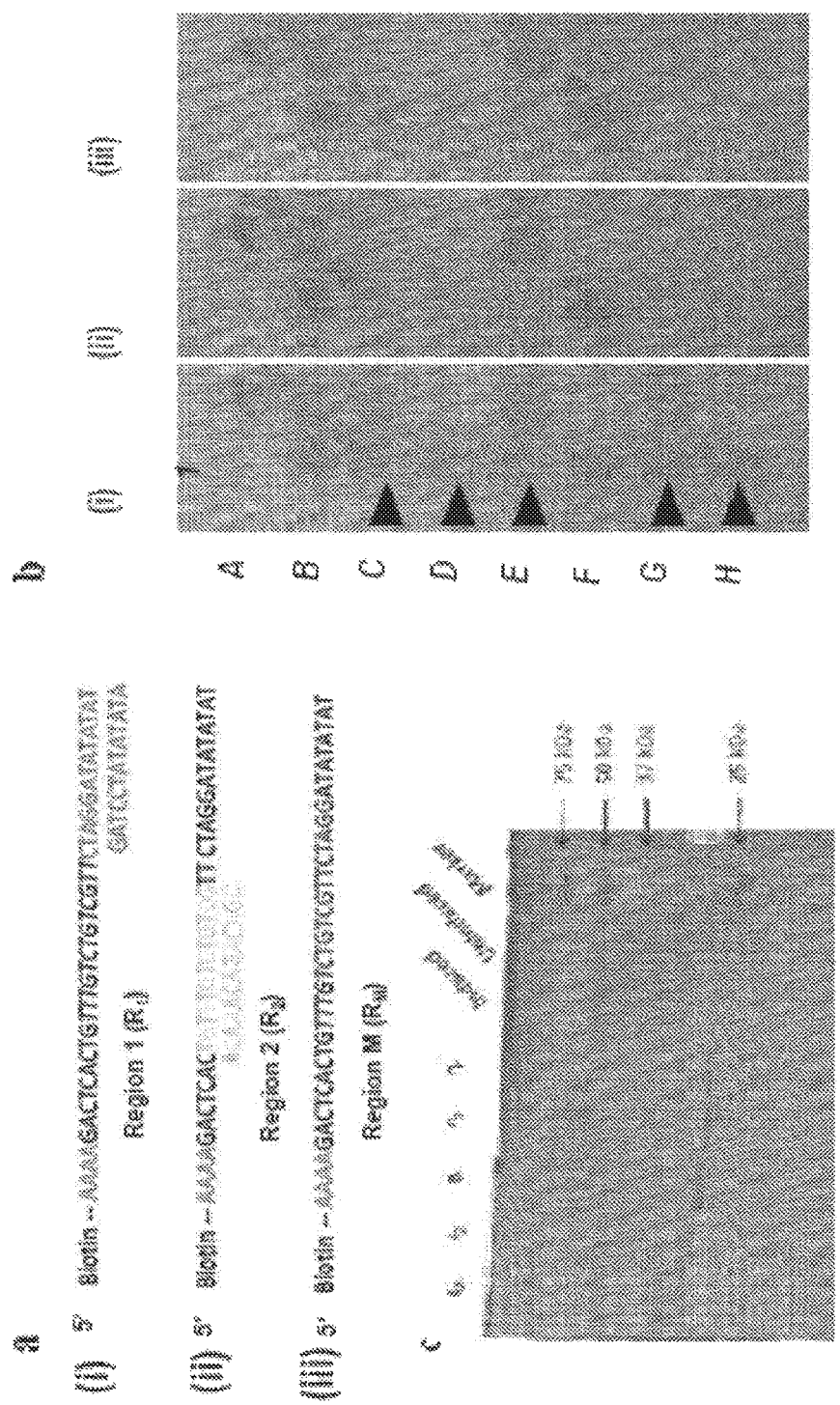
FIG. 6 depicts screening of DNA sequence-specific scFv binders.

FIG. 6 depicts screening of DNA sequence-specific scFv binders. (a) Schematic representation of DNA strands used in sequence specific ELISA screens-$R_1$ (red font), $R_2$ (green font) and $R_M$ (blue font).

(b) (i-iii) ELISA results obtained after incubating protein supernatant of indicated clones with epitopes shown in (a): (i) Region $R_1$, (ii) $R_2$, (iii) $R_M$. Arrowheads are indicative of positive clones specific for $R_1$.

(c) scFv production and purification—Clone C1 is expressed in M9 media supplemented with about 0.2% glycerol. The M9 media comprises 1×M9 salts, 2 mM $MgSO_4$ and 0.1 mM $CaCl_2$).
5×M9(Salts) Composition
 64 g $Na2HPO_4.7H_2O$
 15 g $KH_2PO_4$
 2.5 g NaCl
 5 g $NH_4Cl$
 0.2% Casamino acids and 1 mM Thiamine Hydrochloride.
In FIG. 6, Marker: Precision plus protein marker (Bio-Rad); Uninduced: supernatant of uninduced culture;
Induced: supernatant of culture induced by about 1 mM IPTG;
2-6: fractions 2-6 collected post elution with 500 mM imidazole.

For the experimental protocol, scFv C1 is cultured in about 250 mL 2×TY with about 0.2% Glucose till OD reaches 0.5. *E. coli* TG1 Bacteria is precipitated at 3000 g then resuspended in about 250 mL M9 media described earlier, followed by addition of 1 mM IPTG. Culture is grown for 18 hours and precipitated at 5000 g. Supernatant is filtered with 0.22 µm filter and incubated with NiNTA beads for about 2-3 hours at about 4° C. Beads are loaded in a column, washed with about 50 mL PBS, and eluted with about 500 mM imidazole.

It is to be noted that this purified scFv antibody preparation is used only to measure its binding affinity to the 35 bp dsDNA tag, and that otherwise C1 scFv is always expressed directly in cells as a fusion to furin.

In order to screen for sequence specificity of binding to duplex DNA, each of the selected clones are similarly assayed by ELISA to a set of surface-immobilized DNA scaffolds. These correspond to a single stranded DNA sequence comprising only the biotinylated strand of the 35 bp dsDNA the 35 bp dsDNA duplex (dsDNA), and three shorter duplex regions $R_1$, $R_2$ and $R_M$ corresponding to various sections on the 35 bp dsDNA duplex. $R_1$ corresponds to a 12 bp region at the 3' terminus of the biotinylated ssDNA oligonucleotide, $R_2$ correspond to a 13 bp region abutting $R_1$, while $R_M$ corresponded to a 13 bp region overlapping the 5' end of R1 and the 3' of R2.

The DNA binding scFvs that shows binding to the 35 bp dsDNA epitope but not the ssDNA epitope are chosen for a further screen against the three epitopes $R_1$, $R_2$ and $R_M$. The clones that bind dsDNA are then screened against $R_1$, $R_2$ and $R_M$ that give information on the specificity and narrowed down the size of the epitope.

It is observed that 21% of the clones are specific for $R_1$, whereas 3% of clones bind $R_2$ no are found that only bind $R_M$. Interestingly 3 clones (wells B5, C5, F10) that recognize R2 and binds to the sequence ds(ACAAACA) are found. It is also observed that two clones (wells G3 and F7) which show specific binding to R1 and R2 but show negligible affinity towards $R_M$. Closer scrutiny of both sequences, revealed that the presence of alternate adenines in their sequences. Thus clones G3 and F7 possibly recognize an epitope of A̲XA̲XA̲XA̲X that is present in region 1 (A̲TA̲T A̲TA̲T) as well as region 2 (A̲CA̲A̲A̲CA̲).

Example 1.4: ELISA for Screening Positive Clones

This experiment is performed to find a specific clone among all DNA binding scFvs. Approximately 96 colonies from the final round of selection are screened by ELISA against double stranded DNA (dsDNA). Individual colonies of scFv from last round of selection are grown in 96 well plates till the $OD_{600\ nm}$ reaches approximately 0.9 and then induced with about 1 mM IPTG (Isopropyl β-D-1-thiogalactopyranoside). Cultures are grown at about 30° C. overnight (about 16 hours) for the expression of soluble scFvs which are secreted into the culture media.

The scFvs are transferred onto Streptavidin-conjugated 96-well plate containing immobilized dsDNA to carry out standard ELISA assays. About 150 µL of scFv soup containing about 1 in 1500 dilutions of anti-cMyc antibody (clone 9E10, Millipore)/anti His-tag antibody (clone His-1, Sigma) is added to each well and incubated for about 1.5 hours with gentle shaking.

Goat anti-mouse secondary antibody conjugated to HRP (1 in 1000 dilution, Invitrogen) is used to detect anti-cMyc antibody bound to plate through scFv which can bind to dsDNA immobilized on the plate. In order to check the sequence specificity of the positive clones, scFvs are subjected to another round of ELISA assay against various DNA epitopes. The epitopes used are single stranded DNA (ss 5'-biotinylated oligo only), dsDNA (duplex DNA used as antigen) and various parts of this dsDNA (e.g. region 1 as $R_1$, region 2 as $R_2$ and region middle as $R_M$). After immobilization of these targets, ELISA assay is carried out. This experiment reveals DNA sequence specific scFvs from all positive clones. After screening, a clone C1 that binds a DNA sequence ATATATAT is obtained.

The DNA and Protein sequence of scFv, as per an embodiment of the present disclosure, is provided below.

```
scFv: DNA sequence: SEQ ID No. 15:
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAACGATTACGAAGAGGGGTGAGAGGACAAAGTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

AGTACTCGTGCGTTTGACTACTGGGGCCAGGGAACCCTGGTCACCGTCTC

GAGCGGTGGAGGCGGTTCAGGCGGAGGTGGCAGCGGCGGTGGCGGGTCG

ACGGACATCCAGATGACCCAGTCTCCATCCTCCCTGTCTGCATCTGTAGG

AGACAGAGTCACCATCACTTGCCGGGCAAGTCAGAGCATTAGCAGCTATT

TAAATTGGTATCAGCAGAAACCAGGGAAAGCCCCTAAGCTCCTGATCTAT

GGGGCATCCTATTTGCAAAGTGGGGTCCCATCAAGGTTCAGTGGCAGTGG

ATCTGGGACAGATTTCACTCTCACCATCAGCAGTCTGCAACCTGAAGATT

TTGCAACTTACTACTGTCAACAGACGCGTTTTTCGCCTAATACGTTCGGC

CAAGGGACCAAGGTGGAAATCAAACGGGCGGCCGCACATCATCATCACCA

TCACGGGGCCGCAGAACAAAAACCCATCTCAGAAGAGGATCTGAATGGGG

CCGCAGGTGGGGATCT scFv - Protein sequence: SEQ ID No. 16:
MAEVQLLESGGGLVQPGGSLRLSCAASGFTFSSYAMSWVRQAPGKGLEWV

STITKRGERTKYADSVKGRFTISRDNSKNTLYLQMNSLRAEDTAVYYCAK

STRAFDYWGQGTLVTVSSGGGGSGGGGSGGGGSTDIQMTQSPSSLSASVG

DRVTITCRASQSISSYLNWYQQKPGKAPKLLIYGASYLQSGVPSRFSGSG

SGTDFTLTISSLQPEDFATYYCQQTRFSPNTFGQGTKVEIKRAAAHHHHH

HGAAEQKPISEEDLNGAAGGD
```

Example 1.5: Protein Targeting Strategy of DNA Sensors

In order to obtain a non-natural, sequence-specific, dsDNA-binding protein, a phage display screen of scFv recombinant antibodies against a 35 base pair duplex DNA (dsDNA) epitope is performed. From 60 specific hits, one (clone C1-Row 6, column 1 well in 96 well plate) that binds specifically to a dsDNA sequence d(AT)4 is chosen (FIG. 1c and FIGS. 6a, c).

The binding affinity of this scFv with the 35 bp DNA duplex is assayed using competitive ELISA that is performed using a fixed amount of immobilized dsDNA (25 pmoles) followed by the addition of a fixed concentration of scFv (200 nM) in the presence of an increasing concentration of unlabeled dsDNA ($I^{comp}$, about 10 nM to about 1 μM) in solution. This provides a relative binding constant of about $1.25 \times 10^7$ $M^{-1}$ (i.e., $K_D$=80 nM (FIG. 1D). FIG. 1D describes the binding constant of DNA sensor $I^{Tf}$, made up of Tf con1 and Tf con2'. This figure confirms that clone C1 binds to DNA sensor with a binding constant of 80 nM.

When scFv-Furin expressing HeLa and TRVb-1 cells are incubated with about 500 nM $I^{Fu}_{A488/A647}$ in the external medium and imaged, it is observed that $I^{Fu}_{A488/A647}$ is efficiently endocytosed into perinuclear compartments which is absent in untransfected or mock transfected cells. A competitive endocytic uptake assay reveals that the N-terminal scFv domain of that scFv-Furin acts as a highly specific, artificial receptor for a DNA scaffold containing the 8 bp d(AT)$_4$ tag, efficiently internalizing any DNA device incorporating this sequence.

Example 1.6: Determination of Binding Constants

This experiment is carried out to find strength of binding of clone C1 with DNA. The affinity and specificity of scFv is analyzed by ELISA after purifying the scFv. Streptavidin-coated 96-well plate is incubated with dsDNA epitope used for screening in 5×SSCT (about 75 mM Sodium citrate, about 750 mM NaCl, about 0.05% Tween-20) for about 1.5 hours for immobilization of dsDNA onto the Streptavidin-coated 96-well plate.

For competition experiments, dsDNA immobilized onto Streptavidin-coated 96-well plate is incubated with the mixture of increasing amount of (from 0 to 10 micromoles) of competing nucleic acid, purified scFv (about 200-300 nM) and 1 in 1000 dilution of anti myc-tag antibody for about 1.5 hours at room temperature. The wells are then washed in about 1 liter PBST (1×PBS, 0.1% Tween-20) bath before the addition of the 1 in 1000 dilution of secondary antibody conjugated to HRP. Bound scFvs are detected by addition of 100 microliters of 2×TMB/H202 and OD at 450 nm is recorded and normalized with respect to the well where no competitor is added. This experiment indicates strength of clone C1 binding towards d(AT)4 which is 80 nM.

Example 1.7: Analysis of Fret Pairs

A variety of FRET pairs are tested to identify the most suitable FRET pairs for the method of the present disclosure. Acceptor positions on the DNA assembly are also tested in order to maximize FRET signals. These experiments rely on using either ALEXA FLUOR®-546/ALEXA FLUOR®-555/Bodipy-TMR as the donor, while acceptor used is ALEXA FLUOR®-647. The Nucleic Acid Assembly of DNA sensor is ordered at every position that is not a part of I-motif and tested.

FIG. 23 provides the schematic representations and graphs showing representative fluorescence spectra of $I^{Fu}$ using ALEXA FLUOR®-546 as donor at end of oligo O1-cell (nucleotide 1) and ALEXA FLUOR®-647 as acceptor at nucleotide positions (A) 26, (B) 27, (C) 28, (D) 29 and (E) 32 of the oligo 2. For this protocol, DNA sensor $I^{Fu}$ is diluted to about 50 nM in 1× clamping buffer (clamping buffer composition: 120 mM KCl, 5 mM NaCl, 1 mM $CaCl_2$), 1 mM $MgCl_2$) of about pH 5.0 and 7.0, incubated for about 30 minutes before acquiring spectra. Samples are excited at 545 nm and fluorescence spectra is recorded from 555 nm to 750 nm.

FIG. 24 provides the schematic representation and graphs showing representative fluorescence spectra of $I^{Fu}$ using ALEXA FLUOR®-555 as donor at end of oligo O1-cell (nucleotide 1) and ALEXA FLUOR®-647 as acceptor at nucleotide positions (A) 28 and (B) 32 of the oligo O2. For this protocol, DNA sensor $I^{Fu}$ is diluted to about 50 nM in 1× clamping buffer of pH of about 5.0 and 7.0, incubated for about 30 min before acquiring spectra. Samples are excited at 545 nm and fluorescence spectra is recorded from 555 nm to 750 nm.

FIG. 25 provides the schematic representation and graphs showing representative fluorescence spectra of $I^{Fu}$ using Bodipy-TMR as donor at end of oligo O1-cell (nucleotide 1) and ALEXA FLUOR®-647 as acceptor at nucleotide positions (A) 26, (B) 27, (C) 28, (D) 29 and (E) 32 of the oligo 2. For this protocol, DNA sensor $I^{Fu}$ is diluted to about 50 nM in 1× clamping buffer of pH 5.0 and 7.0, incubated for about 30 min before acquiring spectra. Samples are excited at 545 nm and fluorescence spectra is recorded from 555 nm to 750 nm.

FIG. 26 provides the schematic representation and graphs showing representative fluorescence spectra of $I^{Tf}$ using (A) ALEXA FLUOR®-546 as donor at 5' end of oligo $I^{Tf}$-con 1 and ALEXA FLUOR®-647 as acceptor at nucleotide position 28 of oligo $I^{Tf}$-con 2'. (B) ALEXA FLUOR®-555 as donor at 5' end of oligo $I^{Tf}$-con 1 and ALEXA FLUOR®-647 as acceptor at nucleotide position 28 of oligo $I^{Tf}$-con 2': For this protocol, DNA sensor $I^{Tf}$ is diluted to about 50 nM in 1× clamping buffer of pH of about 5.0 and 7.0, incubated for about 30 min before acquiring spectra. Samples are excited at 545 nm and fluorescence spectra is recorded from 555 nm to 750 nm.

It is observed as a result of the experiments stated above that the FRET pairs that exhibit maximal FRET and minimal crosstalk—are ALEXA FLUOR®-488/ALEXA FLUOR®-647 (A488/A647) and ALEXA FLUOR®-546/ALEXA FLUOR®-647 (A546/A647). They show maximal FRET and minimal crosstalk when employed simultaneously. Thus, in an embodiment of the present disclosure, $I^{Tf}$ carries ALEXA FLUOR®-488/ALEXA FLUOR®-647 as its FRET pair ($I^{Tf}_{A488/A647}$) while $I^{Fu}$ carries ALEXA FLUOR®-546/ALEXA FLUOR®-647 as its FRET pair ($I^{Fu}_{546/A647}$) (FIG. 7).

Figure 7:
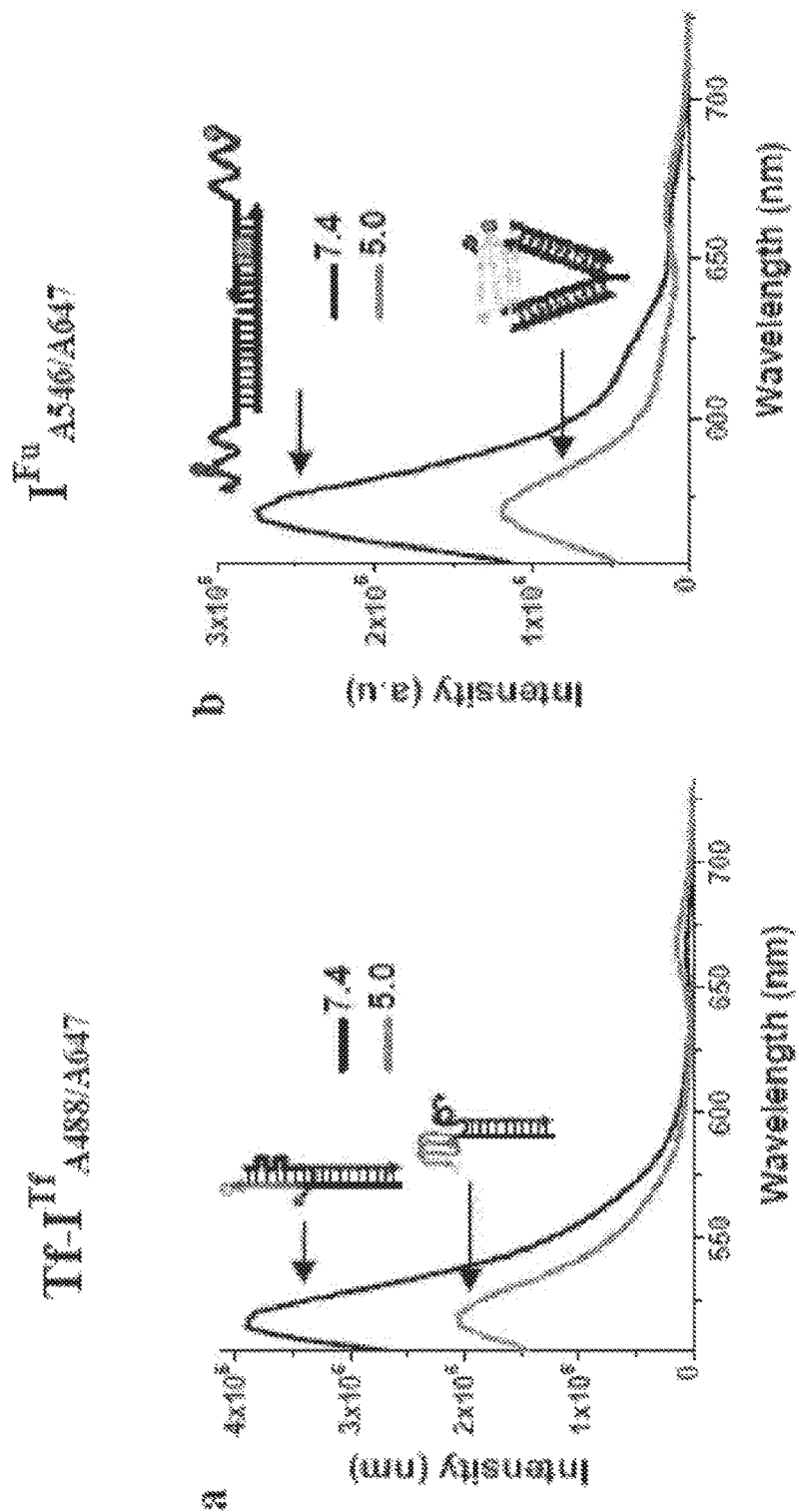
FIG. 7 depicts the representative steady state fluorescence spectra of programmed DNA sensors.

FIG. 7 depicts the representative steady state fluorescence spectra of programmed DNA sensors of the present disclosure. Fluorescence spectra of DNA sensor specific for (a) Transferrin pathway—Tf-$I^{Tf}$ and (b) for Furin pathway—$I^{Fu}$ for simultaneous pH measurements are represented. For this protocol, DNA sensor is diluted to about 50 nM in 1× clamping buffer of pH about 5.0 and 7.4, incubated for about 30 min before acquiring spectra. Samples are excited at 495 nm and 545 nm respectively and fluorescence spectra is recorded from 505 nm (for 495 nm excitation)/555 nm (for 545 nm excitation) to 730 nm.

$I^{Fu}_{A546/A647}$ shows a pH sensitivity from pH of about 5 to about 6.5, suitable for studying pH variations in the sorting endosome, late endosome and TGN, with typical intraorganelle pH values indicated by the green arrowheads (FIG. 1e). $I^{Tf}_{A488/A647}$ shows a much broader transition starting from pH of about 5.5 to pH of about 7.0, spanning the sorting and recycling endosomal pH with typical intraorganelle pH values indicated by the purple arrowheads (FIG. 1f).

Example 1.8: Characterization of DNA Sensors

Both DNA sensors, $I^{Fu}$ and $I^{Tf}$ are characterized biophysically and biochemically prior to their application in cells. These DNA Sensors are characterised using three different biophysical methodologies:
(i) pH-dependent Circular Dichroism (CD) studies and
(ii) pH-Dependent FRET.
1. The difference in CD spectrum of a solution of the DNA sensor (for both $I^{Fu}$ and $I^{Tf}$) at pH of about 5.0 and pH 7.0 shows a characteristic CD profile that shows a positive band centred at about 288 nm and a negative band centered at about 262 nm. The prior art provides the expected fingerprint CD spectra for an I motif. In the present disclosure, the difference in CD spectrum corresponds exactly to that of an I-motif, indicating that the DNA assembly at pH of about 5.0 is consistent with a structure, where, in addition to the duplexed regions at pH of about 7.0 being intact, the formation of an I-motif structure by the C-rich region is evident (FIG. 27A-B).
2. Importantly, as one proceeds from solution pH of about 7.0 to pH of about 5.0, the CD signal at about 292 nm of the sensors shows an increase (due to I-motif formation) and serves as a diagnostic peak to follow the pH-dependent structural transition of the DNA sensor. FIGS. 27 C and D depict the pH dependent structural transition as followed by circular dichroism for both sensors ($I^{Fu}$ and $I^{Tf}$). The transition is also recapitulated by fluorescence spectroscopy when using DNA sensors carrying appropriately positioned FRET pairs.
3. In an additional experiment, when FRET pairs such as ALEXA FLUOR®-488 (Donor) and ALEXA FLUOR®-647 are positioned as indicated in the Table 1, they undergo FRET at pH of about 5.0 due to I-motif formation. Importantly, fluorescence spectra upon exciting the Donor at about 488 nm and recording spectra between about 550 nm-730 nm as a function of pH intermediate between pH of about 5.0 and 7.0 are shown in FIGS. 27 E and F. These indicate a gradual decrease in FRET going from pH of about 5.0 to 7.0, showing an increasing D/A value that is also plotted in FIG. 2D for both DNA sensors. Decreasing FRET means at pH 5.0, low emission at 520 nm and high emission 670 nm is transformed to high emission at 520 nm and low emission at 670 nm, at pH 7.0.

This is also in compliance with documented fluorescence quenching study involving I-motif formation as a function of pH, performed with ALEXA FLUOR®-488/Dabcyl labeled cytosine rich oligo.

Example 1.9: Cell Culture and Transfection

This experiment is performed for expression of furin chimera in cells. In embodiments of the present disclosure, HeLa cells and IA2.2 cells are used with the DNA sensors of the present disclosure.

HeLa cells are cultured in Dulbecco's Modified Eagle's medium/F-12 (1:1) (Invitrogen Corporation, USA) containing about 10% heat inactivated Fetal Bovine Serum (FBS) (Invitrogen Corporation, USA), about 100 µg/mL Streptomycin and about 100 U/mL Penicillin (All components from Invitrogen Corporation, USA).

IA2.2 cells are a Chinese Hamster Ovary (CHO) cell line which lacks endogenous transferrin receptors but stably expresses the human transferrin and folate receptors. For experiments of the present disclosure, IA2.2 cells are obtained from Professor Satyajit Mayor (NCBS). These cells are cultured in Ham's-F12 Complete media (HF-12, Himedia, India) containing about 10% heat inactivated FBS, about 100 µg/mL Streptomycin and about 100 U/mL Penicillin with about 200 µg/mL G418 and about 100 µg/mL hygromycin to ensure maintenance of transferrin and folate receptors.

For imaging and transfection, IA2.2 cells are maintained in Ham's-F12 complete media without G418 and hygromycin. For transient transfections, IA2.2 cells are plated at greater than 50% density onto coverslip bottomed 35 mm dish and about 150 ng of scFv-Furin is introduced using the Lipofectamine 2000 reagent system (Invitrogen Corporation, USA), following the manufacturer's instructions to Obtain scFv expressing cell. Cells are imaged 24 hours after transfection.

Figure 2:
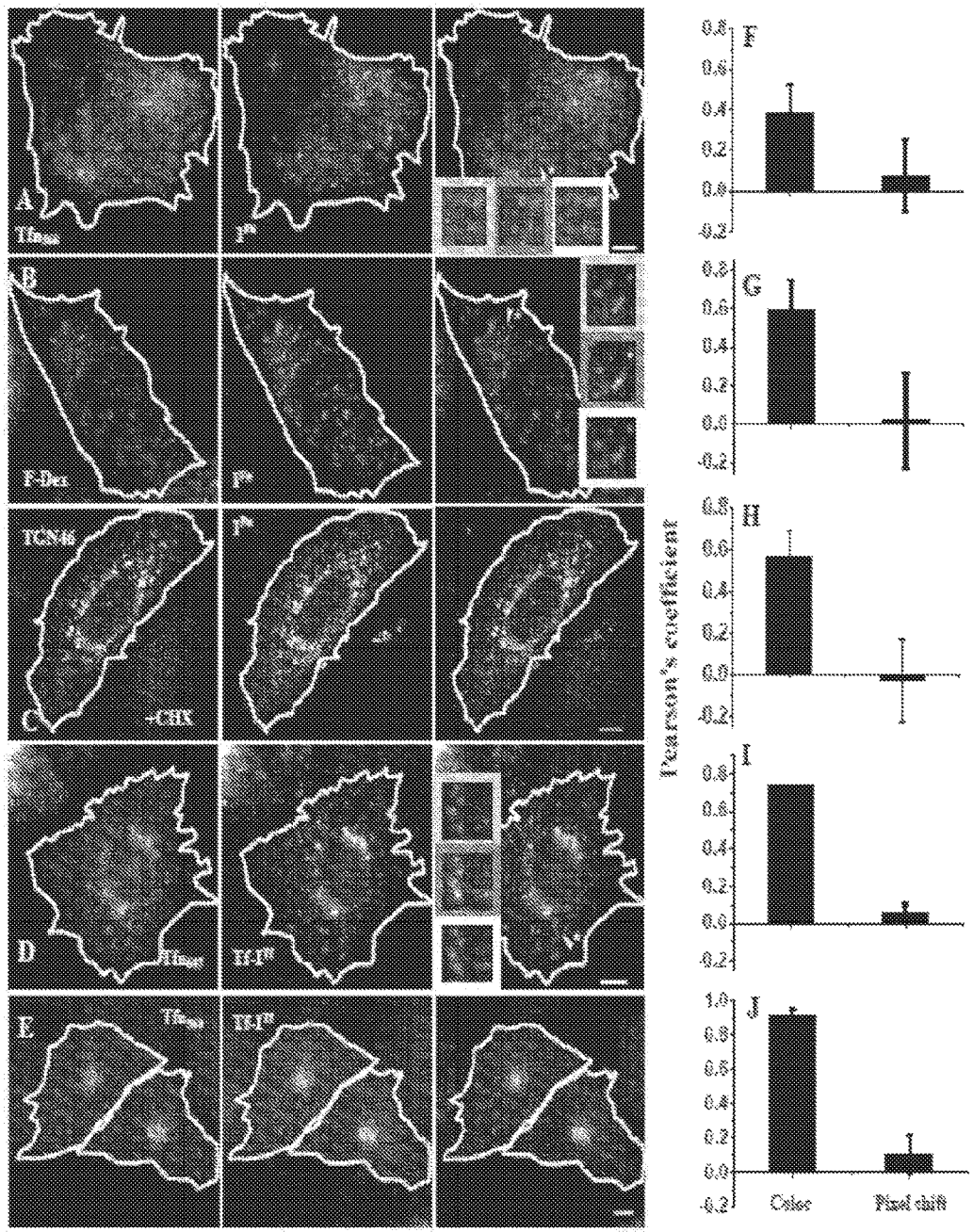
FIG. 2 depicts the programmed trafficking of DNA sensors along two distinct endocytic pathways.

Wide-field and confocal images are collected using a Nikon eclipse Ti-U inverted microscope and an Olympus Fluoview 1000 confocal microscope respectively. Donor and acceptor images are overlayed and endosomes showing co-localization are further quantified using ImageJ as seen in FIG. 2 of the present disclosure. This experiment is performed to pinpoint DNA sensor trafficking in cells and it confirms DNA sensor co-localization with endosomal markers.

Example 2: Working pH Regime of DNA Sensors

Different cellular organelles maintain their lumenal pH set point at values ranging from pH of about 4.8 (lysosome) to pH of about 7.1 (endoplasmic reticulum) and in order to accurately measure pH correlates associated with organelle functionality, it is important to have DNA sensors that span the appropriate pH regime and as well as FRET pairs for simultaneous measurements. The performance and working pH regime of the DNA sensors carrying the relevant FRET pairs, engineered specifically for the transferrin and furin pathways respectively, is shown in FIG. 1e-f.

In FIG. 1, (a) Schematic representation of the working principle of two DNA sensors for simultaneous spatiotemporal pH mapping is provided.

DNA sensor used for transferrin endocytic pathway, $I^{Tf}$: At neutral/basic pH, it exists as a mismatched duplex and at acidic pH, the functional C-rich domain (purple) forms an intramolecular I-motif resulting in a high FRET state.

DNA sensor used for furin retrograde transport pathway, $I^{Fu}$: At neutral pH, it adopts an extended conformation with two C-rich overhangs which fold into an I-motif conformation at low pH. A dsDNA domain on $I^{Fu}$ (shown in gray) acts as a recognition element for a recombinant antibody (scFv, gray cylinders inset). Two different FRET pairs (ALEXA FLUOR®-488 and ALEXA FLUOR®-647) for $I^{Tf}_{A488/A647}$ and (ALEXA FLUOR®-546 and ALEXA FLUOR®-647) for $I^{Fu}_{A546/A647}$ act as fluorescent reporters.

(b) Schematic representation of the DNA sensors tracking both protein trafficking pathways. Transferrin conjugated $I^{Tf}$ (Tf-$I^{Tf}$) marks the sorting endosome (SE) en route to recycling endosome (RE). An scFv-furin fusion protein (gray) binds and retrogradely transports $I^{Fu}$ into the trans-Golgi network (TGN) via the sorting endosome (SE) and late endosome (LE).

(c) dsDNA sequence specific binding of the scFv (clone C1) obtained from a phage display screen. Epitopes used: Single stranded DNA (ssDNA), dsDNA, Region 1($R_1$), Region 2 ($R_2$) and Middle Region ($R_M$). This figure provides that Clone C1 binding is specific to a DNA sequence of ATATATAT.

(d) Binding of scFv to immobilized dsDNA in the presence of increasing amounts of competitor dsDNA. In all cases, absorbance at 450 nm is normalized with respect to binding in the absence of competitor DNA.

(e and f) Donor (D) to acceptor (A) ratio measurements on dually labelled DNA sensors $I^{Tf}$ and $I^{Fu}$ in vitro and in cellulo as a function of pH. Ratio of fluorescence intensities at 570 nm (D) and 669 nm (A) for $I^{Fu}_{A546/A647}$ (e) and 520 nm (D) and 669 nm (A) for $I^{Tf}_{A488/A647}$ (f) when excited at 546 nm and 488 nm respectively in pH clamping buffer of indicated pH. All experiments are performed in triplicate and expressed as mean±SD. FIGS. 1e and f, provide the intracellular calibration curves of $I^{Fu}$ and $I^{Tf}$ from which, pH of the organelles is measured.

Example 3: Steady State and Ratiometric pH Measurements

This experiment is provides the steady state and ratiometric measurements by the DNA sensors of the present disclosure. It is performed to find out in vitro pH response curve of DNA sensor. All the unlabelled oligonucleotides used in the present disclosure are obtained from Eurofins Genomics India Pvt. Ltd. and labelled oligonucleotides (HPLC purified and lyophilized) are obtained from IBA GmbH (Germany). For preparing the oligonucleotide mixtures used in the present disclosure, about 5 μM each of I" and I"' are mixed in equimolar ratios in about 20 mM Potassium Phosphate buffer of desired pH containing about 100 mM KCl. The resultant solution is heated to about 90° C. for about 5 minutes, cooled to the room temperature at about 5° C./15 min and equilibrated at about 4° C. overnight.

Solutions of DNA sensors at different pH are made by diluting about 1 μL of about 5 μM stock samples of DNA pH sensors, either $I^{Fu}$ or $I^{Tf}$ into about 99 μL of 1× clamping buffer of desired pH. All samples are vortexed and equilibrated for about 30 min at room temperature. The experiments are performed in a widefield microscope (Nikon Eclipse Ti-U, Nikon Japan). The cover-slips containing about 50 μL samples of DNA sensors at different pH are excited at 488 nm (for A488/A647 pair) and 550 nm (for A546/A647 pair) in a widefield microscope and emission images are acquired using 520 nm (donor, D channel) and 669 nm (acceptor, A channel).

An in vitro pH calibration curve is obtained by plotting the ratio of donor intensity (D) at 520 nm by acceptor intensity (A) at 669 nm (for A488/A647) and (570 nm by 670 nm for A546/A647 pair) as a function of pH. Mean of D/A values from two independent experiments are taken and their SD values are plotted for each pH value. D/A values from different experiments are added and Mean±SD is plotted over pH. In case of endosomes, mean D/A values over a collection of endosomes is calculated. Mean D/A values of two to three different days are compared with the calibration curve and pH is noted.

Data analysis reveals that these sensors measure pH dynamics of endosome and TGN without any effect of S/N (Signal-to-noise ratio) on D/A ratios (and hence pH).

Effects of Noise and Signal/Noise Ratio on pH Estimates

In order to discount the contribution of noise and signal/noise ratio (S/N) to pH estimates, especially in areas of low fluorescence intensity, endosomes of diverse intensity are chosen, without any bias to endosomes of specific intensities. FIG. 28a shows a typical scatter plot of mean donor intensity (D) with observed mean acceptor intensity (A) at both extreme pH values (pH 5.0 and 7.2) (FIG. 28a, c). The symmetrical distribution of intensities about the slope without particular scatter either towards high D or low A is noteworthy. The slope obtained from the plot are in good agreement with the mean D/A obtained from the total endosomes.

S/N at the transition pH of a given DNA sensor is equally important and to rule out any contribution of pH estimates, two typical scatter plots at $pH_{1/2}$ (FIG. 28b, d) are plotted. Here mean donor intensity (D) is taken and plotted as a function of D/A, to demonstrate that even if the data is analyzed using a method different from that shown in FIGS. 28a and c, S/N is a non-issue for these systems. A symmetrical distribution over mean D/A at lower donor intensity confirmed that even at transition pH, DNA sensors show minimal effect of low donor intensity. The Y-axis regimes are chosen to span the complete range of D/A that is exhibited by the respective DNA sensor.

To check the number of endosomes that show altered D/A due to their low donor or acceptor intensities, these donor and acceptor intensities are correlated with individual endosomal D/A in a 2D scatter plot. The pH of endosomes labelled with FITC-Dextran and TMR Dextran is clamped to pH 6.0 and about 180 endosomes are analyzed by the above method (this is done by taking the ratio of FITC and TMR and plotting FITC & TMR intensities versus the FITC/TMR ratio). The FITC/TMR ratio shows a Gaussian spread as expected, with ~3% of endosomes falling outside the range of the mean±2 SD (SD=standard deviation).

This parameter of mean±2 SD is used as a threshold for the analysis of pH clamped endosomes labelled with $Tf-I^{Tf}$ and $I^{Fu}$ to estimate the proportion of outliers, and if this is significant, to what extent it contributes to the errors/spread in the pH measurement.

| | $I^{Fu}$ | | $Tf-I^{Tf}$ |
|---|---|---|---|
| pH 5 | ~1.7% (4 out of 225) | pH 5.0 | ~1.6% (2 out of 124) |
| pH 5.5 | ~4.6% (9 out of 193) | pH 6.25 | ~4.7% (7 out of 143) |
| pH 6 | ~3.6% (7 out of 194) | pH 6.5 | ~4% (5 out of 124) |

FIG. 28 depicts effect of signal/noise ratio on D/A at different pH values. (a) Scatter plot of donor (D) versus acceptor (A) intensities for $Tf-I^{Tf}_{A488/A647}$. (b) Scatter plot of D/A with D at the transition pH of $Tf-I^{Tf}_{A488/A647}$. (c) Scatter plot of D versus A for $I^{Fu}_{A546/A647}$. (d) Analogous scatter plot of D/A with D at the transition pH of $I^{Fu}_{A546/A647}$.

FIG. 29 depicts effect of donor and acceptor intensities on D/A ratio. A 2D D/A scatter with respect to mean donor and acceptor intensities was plotted. Mean donor is represented in red and mean acceptor is represented in blue. Mean±2SD with respect to mean is represented as solid lines. Any endosomes that fall outside this threshold are considered as outliers All experimental pH measurements are on organelles that show pH<6.5 under any condition. It is apparent that less than 10% of endosomes fall outside the significance range. Hence due to their small numbers, their contribution to the spread of the mean pH population is negligible.

Example 4: Fluorescence Staining Methods

This experiment is done to label endosomes and other cellular organelles inside cells with DNA sensors. scFv-Furin expressing IA2.2 cells obtained in the example above, are washed thrice with about 1 mL of Medium1 (M1) buffer, comprising 150 mM NaCl, 5 mM KCl, 1 mM $CaCl_2$), 1 mM $MgCl2$ and 20 mM HEPES, at pH of about 7.4 prior to labelling. Cells are incubated with endocytic tracers for indicated times in labelling medium (complete medium), as seen in FIG. 2 of the present disclosure.

For labelling cells with $I^{Fu}$, Labelling media—1 comprising Ham's-F12 Complete media (HF-12, Himedia, India) containing about 10% heat inactivated FBS, about 100 µg/mL Streptomycin and about 100 U/mL Penicillin, without G418 and hygromycin is used. When $I^{Tf}$ or any form of transferrin is involved, labelling of cells is done in Labelling media—2, i.e. M1 buffer, comprising 150 mM NaCl, 5 mM KCl, 1 mM $CaCl_2$), 1 mM $MgCl2$ and 20 mM HEPES, at pH of about 7.4.

For DNA sensor labelling, $I^{Fu}_{A488/A647}$ is diluted in Labelling media—1 to final concentration of about 500 nM, while Tf conjugated DNA sensor ($Tf-I^{Tf}_{A488/A647}$) is diluted in Labelling media—2—M1 buffer to final concentration of about 500 nM and incubated for different times at about 37° C.

For labelling late endosomes, cells are incubated with $I^{Fu}_{A488/A647}$ and about 2 mg/mL FITC dextran (labels late endosomes) in labelling media at about 37° C. for about 1 hour followed by a chase for about 1 hour. Sorting endosomes are labelled by about 100 µg/mL ALEXA FLUOR®-568 labelled human holo-transferrin (marks early/sorting and recycling endosomes) after incubating IA2.2 cells at about 37° C. for about 10 minutes in M1 buffer while a brief chase of about 12 minutes marks recycling endosomes.

After incubation, excess endocytic tracers are washed off using M1 buffer and chased for indicated times at about 37° C. in complete media. Trans Golgi Network (TGN) is labelled by incubating the cells with $I^{Fu}_{A546/A647}$ for about 1.5-2.0 hours in complete/labelling medium containing about 125 µg/mL cycloheximide (CHX) followed by a chase of about 1.5 hours in same CHX containing media. In presence of CHX, DNA sensor marks the Trans Golgi Network.

Example 5: Immunofluorescence Staining

After labelling of cells described above, Immunofluorescence staining is carried out on scFv-Furin expressing IA2.2 cells, after fixing with about 4% paraformaldehyde for about 20 minutes at room temperature. To detect intracellular antigens, they are permeabilized with about 0.1% Saponin (Sigma) in M1 buffer for about 15 min and stained with mouse anti-TGN46 antibody (Abcam) for about 1 hour in blocking buffer (1 in 500, 5% BSA in M1 buffer), rabbit anti-Giantin (1 in 250) and rabbit anti Lamp-1 antibodies (1 in 250 Abcam) followed by goat anti rabbit-Cy3 conjugated (1 in 1000, Abcam) and goat anti mouse-ALEXA FLUOR®-488 conjugated (1 in 500) secondary antibodies (Invitrogen) for about 1 hour respectively. This experiment confirms localization of DNA sensors to different cellular organelles.

Example 6: Measurement of pH in Sorting and Late Endosomes

This experiment is done to measure pH of different endocytic organelles and TGN with DNA Sensor. scFv-Furin expressing IA2.2 cells are labelled with about 500 nM $I^{Fu}_{A546/A647}$ in complete media or about 500 nM $Tf-I^{Tf}_{A488/A647}$ in M1 buffer for indicated times at about 37° C. Intracellular pH gradient is abolished by addition of about 50 µM nigericin and about 50 µM monensin in different pH clamping buffers ranging from pH of about 5.0 to about 7.5 for about 45 minutes. The cells are kept in this medium until imaging, and the fluorescence ratio of donor (D, 520 nm or 570 nm as applicable) image to acceptor (A, 669 nm) image at different equilibrated pH is calculated in individual endosomes after exciting at 488 nm.

The mean from the distribution of D to A ratio of individual endosome are obtained at different pH and plotted to obtain a calibration curve. The pH of sorting endosomes, late endosomes and TGN is estimated after labelling the respective compartments with Tf-I$^{Tf}_{A488/A647}$ and I$^{Fu}_{A546/A647}$, calculating D/A ratios and then estimating the pH value from the calibration curve (FIGS. 1E and F).

D/A ratio is the ratio of donor and acceptor, after exciting at donor wavelength restricted but not limited to direct excitation of acceptors at the excitation wavelength. The ratio is not restricted to two different fluorescent dyes and can be the ratio of a single dye emitting at two different wavelengths.

Image Acquisition and Analysis

Widefield images are collected using Nikon eclipse Ti-U microscope (Nikon Japan) inverted microscope equipped with 60×, 1.4 NA objective, a metal halide illuminator (Lumen Dynamics, Ontario, Canada), and a cooled charge-coupled device (CCD) camera (Cascade II-512, Photometrics, Tucson, Ariz., USA) controlled by METAMORPH® software (Molecular Devices, Downingtown, Pa.). Optimal dichroics, excitation, and emission filters are used.

For pH measurements, cells are imaged in three channels to yield four images:
  (i) Donor channel by exciting at 488 nm and collecting at 520 nm.
  (ii) Acceptor channel by exciting at 488 nm and collecting at 669 nm.
  (iii) Donor channel by exciting at 550 nm and collecting at 570 nm.
  (iv) Acceptor channel by exciting at 550 nm and collecting at 669 nm.
  (v) Acceptor channel by exciting at 633 nm and collecting at 669 nm.

Cross talk and bleed-through are measured with donor only and acceptor only samples and found to be negligible for ALEXA FLUOR®-488/647 pair while it is observed that around 25-30% of ALEXA FLUOR®-647 is directly excited at 550 nm excitation and subtracted from corresponding donor (A488 excitation, 520 emission image) for representative images. Donor only sample is excited at 520 nm or 570 nm and intensity at 670 nm is followed. Bleed-through of 520 or 570 on 670 nm is calculated as:

Fraction of intensity=Intensity at 670/Intensity 520 or 570*100

Autofluorescence is measured on unlabelled cells. All the images are then background subtracted taking mean intensity of the cytoplasm and donor and acceptor images are co-localized and endosomes showing co-localization are analysed using ImageJ software (NIH). Total intensity as well as mean intensity in each endosome is measured in donor and acceptor channels and a ratio of donor to acceptor intensities (D/A) of each endosome is obtained. For time lapse imaging, cells are labelled as described earlier and after incubation for about 10 minutes with endocytic ligands, cells are imaged at 1 frame (1 s exposure) per 2 seconds for a 3 to 5 minute period and compressed to about 7 frames per second (fps).

Example 7: Distinct DNA Sensors are Trafficked Along Distinct Endocytic Pathways This experiment is done to characterize DNA sensor trafficking in endocytic organelles and TGN. To see how I$^{Fu}$ marks the furin retrograde pathway, co-localization experiments with molecular markers of sorting endosome, late endosome and TGN are performed in IA2.2 cells expressing scFv-furin. When scFv-furin expressing IA2.2 cells are labelled with a 10 min pulse of a cocktail of ALEXA FLUOR®-568 labelled transferrin (Tfn$_{A568}$) and I$^{Fu}_{A488/A647}$ and imaged, they show significant co-localization. This indicates that post-endocytosis, I$^{Fu}$ is majorly resident in sorting endosomes (FIG. 2A, F). When chased for about 2 hours, this co-localization is markedly reduced, indicating that I$^{Fu}_{A488/A647}$ has trafficked forward from the sorting endosome (FIG. 8a, d).

When scFv-furin expressing IA2.2 cells are labelled for about 1 hour with a cocktail of I$^{Fu}_{A546/A647}$ and FITC-dextran, and chased for about 1 hour, they show significant co-localization (FIG. 2B, G) indicating that I$^{Fu}$ has trafficked onwards from sorting endosome into the late endosome.

When these cells are labelled with I$^{Fu}_{A546/A647}$ for about 2 hours in the presence of about 125 μg/mL cycloheximide (CHX) and chased for about 90 min in presence of CHX, it is observed that I$^{Fu}$ has trafficked onwards from the late endosome (FIGS. 8 B, C, E), accumulating in a perinuclear compartment distinct from the lysosome and Golgi bodies as revealed by Lamp-1 and Giantin immuno-staining/immuno-fluorescence (FIG. 9a, b). This IFu containing compartment is confirmed to be TGN by co-localization experiments with NBD-C6-ceramide and anti-TGN46 antibodies.

In an embodiment of the present disclosure, DNA sensor traffics onwards from sorting and late endosomes. After endocytosis, furin traffics from early/sorting endosome to late endosome and finally accumulates in Trans-Golgi Network (TGN). To check whether I$^{Fu}$ is still resident in these organelles, first scFv-Furin expressing HeLa cells are labelled with a mixture of Tfn$_{568}$ and I$^{Fu}_{A488/A647}$ for about 10 min and chased for about 2 hours. Co-localization between the two markers is lost, also confirmed by Pearson's correlation method, showing that at this time point fu has trafficked forward from early/sorting endosomes (FIGS. 8A and D).

Figure 8:
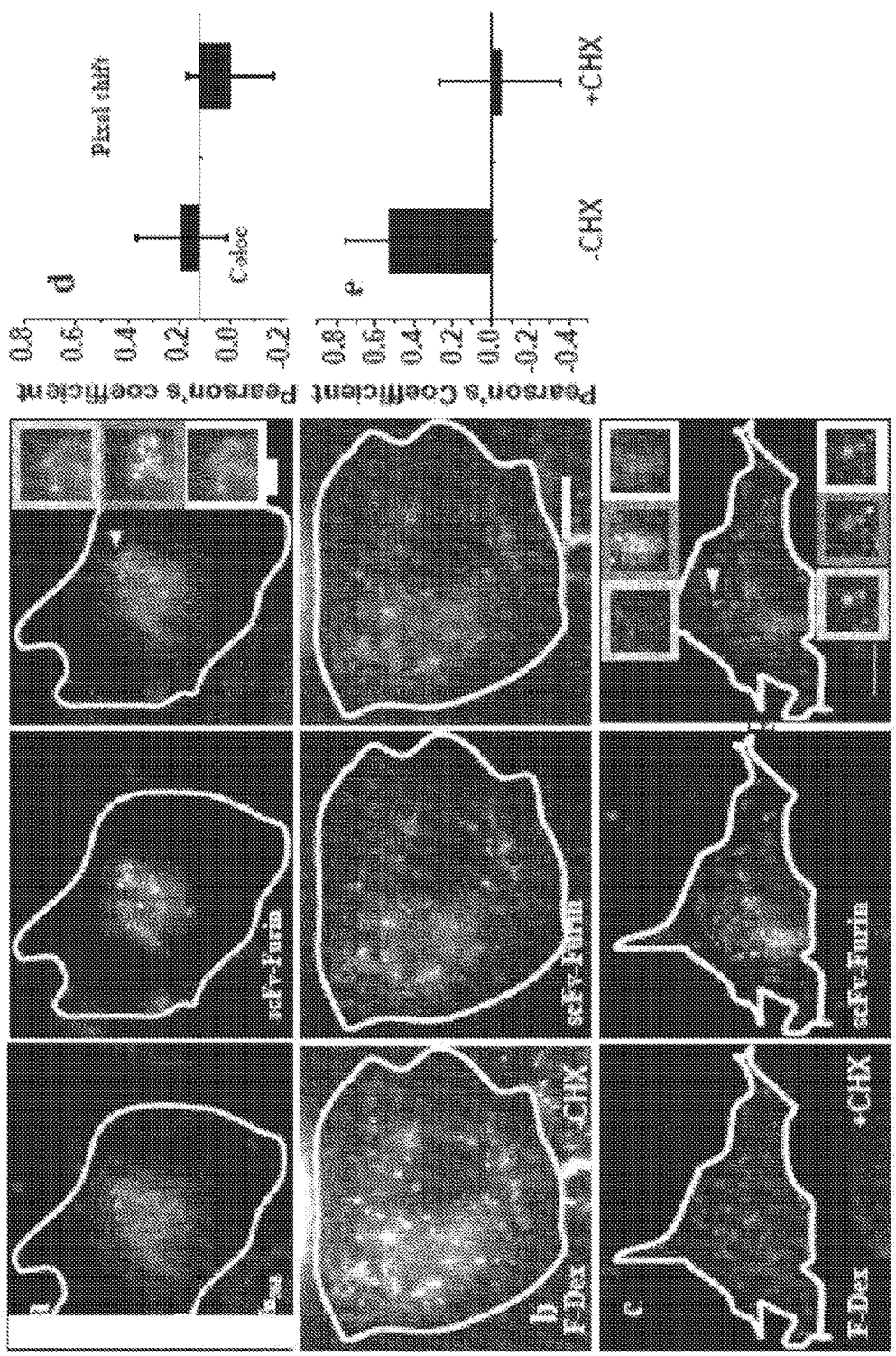
FIG. 8 depicts the trafficking of DNA Sensor onwards from sorting and late endosomes.

Trafficking of I$^{Fu}$ onwards from late endosomes is analyzed by co-pulsing cells with FITC-Dextran and I$^{Fu}_{A546/A647}$ for about 2 hours in presence of CHX followed by a chase for about 1 hour in CHX containing complete-media. I$^n$ control cells, similar labelling protocol is used in absence of CHX to confirm late endosomal accumulation. Pearson's coefficient reveals that in absence of CHX, I$^{Fu}$ is localized in late endosomes whereas in presence of CHX, I$^{Fu}$ is transported out from late endosomes (FIGS. 8 B, C and E).

For determination of Pearson's correlation, images are converted to 8 bit in imageJ and then two images are subjected to analysis in co-localization finder plugin in image J. Pearson's coefficient is measured from this plugin. As per the Pearson's coefficient calculations:

Score=(−1)—anti correlation;

Score=0—no colocalization;

Score=1—perfect colocalization; and

Score=Any value between 0.3 to 1 is known to be co-localization; below 0.5 it is partial co-localization and above 0.5 it is good co-localization.

To confirm the identity of these compartments, these I$^{Fu}_{A546/A647}$ labelled compartments are further stained with TGN markers such as NBD-C6-ceramide and anti-TGN46 antibodies. Confocal microscopy reveals significant co-localization of I$^{Fu}_{A546/A647}$ with anti-TGN46 antibody as well as NBD-C6-ceramide, confirming TGN accumulation (FIG. 2C, H, FIG. 9c).

Taken together, these aspects reveal that the scFv domain on scFv-furin functions as an artificial receptor for DNA sensors bearing a d(AT)$_4$ dsDNA tag and is stable inside cells for up to 3 hours. Further, a DNA sensor molecularly programmed with the d(AT)$_4$ tag is ferried specifically along the trafficking pathway of the membrane protein to which the scFv is fused.

FIG. 2 depicts the programmed trafficking of DNA sensors along two distinct endocytic pathways. Co-localization experiments are performed with molecular markers for SEs, LEs and TGN.

(A-C) $I^{Fu}$ trafficking along the retrograde endocytic pathway of furin. scFv-furin expressing IA2.2 cells pulsed with (A) $I^{Fu}{}_{A488/A647}$ and transferrin-A568 (Tfn$_{568}$) for 10 min at about 37° C., washed, fixed and imaged in a Confocal microscope. (B) $I^{Fu}{}_{A546/A647}$ and FITC-dextran (F-Dex, 10 kDa) at about 37° C. for about 1 hour, chased for about 1 hour and then imaged. (C) $I^{Fu}{}_{A546/A647}$ is used to label cells for about 2 hours at about 37° C. in presence of about 125 μg/ml cycloheximide (CHX), chased in CHX containing medium for about 1.5 hours at about 37° C., immunostained with mouse anti TGN46 antibody.

(D to E) Tf-$I^{Tf}$ trafficking along the transferrin receptor pathway. IA2.2 cells are co-pulsed with (D) Tf-$I^{Tf}{}_{A488/A647}$ and Tfn$_{568}$ for about 10 min in M1 buffer at about 37° C., washed, fixed and imaged. (E) Tf-$I^{Tf}{}_{A488/A647}$ and Tfn$_{568}$ at about 37° C. for about 10 min, followed by a brief chase of about 12 min for recycling endosomal labelling, washed and imaged.

(F to J)—Quantification of co-localization between DNA sensors and endosomal markers used in (A-E). Values indicate mean of >10 cells (F to G and J) and 20 cells (H to I)±SD. Experiments are performed in duplicate. Scale bar: 10 μm for (A and B), and 5 μm (C and E).

FIG. 8 depicts the trafficking of DNA Sensor onwards from sorting and late endosomes. scFv-Furin expressing HeLa cells pulsed with $I^{Fu}{}_{A488/A647}$ and Transferrin-A568 (Tfn$_{568}$) for about 10 min at about 37° C., washed, chased for about 2 hours and imaged.

(b, c)—scFv-Furin expressing IA2.2 cells co-pulsed with $I^{Fu}{}_{A546/A647}$ and FITC-Dextran in absence of CHX (b), and in presence of about 100 μg/mL CHX (c), and chased for about 1 hour in absence (−CHX) or in presence of CHX (+CHX), washed and imaged in a widefield microscope.

(d, e)—Quantification of co-localization between $I^{Fu}$ and endosomal markers used in a and b, by Pearson's correlation method. Arrowheads indicate representative regions shown in insets. Experiments are performed in duplicate. Error bar: Mean±SD. Scale Bar: 5 μm.

scFv-Furin does not Localize in Lysosomes or the Cis-Golgi

I$^n$ order to confirm identity of those compartments containing $I^{Fu}$ that have trafficked onwards from late endosomes, co-localization is carried out with:

(a) lysosomal and
(b) cis-Golgi markers.

To confirm scFv-Furin localization, scFv-Furin expressing IA2.2 cells are labelled with $I^{Fu}{}_{A546/A647}$ as described earlier and fixed using about 4% PFA and stained against a lysosomal marker Lamp-1 and cis-Golgi marker Giantin with respective antibodies. It is observed that $I^{Fu}$ neither colocalizes with Lamp-1 (FIG. 9a) nor with Giantin (FIG. 9b), indicating that $I^{Fu}$ at this stage is not in the cis-Golgi nor the lysosome. To confirm its localization in TGN, cells are labelled with 1 in 1000 dilution of NBD-C6-Ceramide for about 30 minutes in 100 μL of M1 buffer in presence of about 125 μg/mL CHX and chased for about 30 min in 100 μL of M1 buffer containing 125 μg/mL of CHX. NBD-C6-Ceramide shows co-localization with $I^{Fu}$. Thus, it is confirmed that in presence of CHX, scFv-Furin traffics out of late endosomes into TGN (FIG. 9c).

FIG. 9 describes retrograde transport of DNA Sensor into the trans-Golgi network. scFv-Furin expressing IA2.2 cells pulsed with $I^{Fu}{}_{A488/A647}$ for about 2 hours in presence of about 125 μg/mL CHX and chased for about 1.5 hours in presence of 125 μg/mL CHX, washed and fixed using about 4% PFA in 100 μL M1 buffer. Cells are then probed with (a) Rabbit anti Lamp-1 antibody,
(b) Rabbit anti Giantin antibody followed by Cy3 conjugated secondary antibodies and imaged in a confocal microscope.
(c) TGN localization of $I^{Fu}$ at indicated time. Cells are pulsed and chased with $I^{Fu}{}_{A546/A647}$ as described earlier and stained with 1 in 1000 dilution of NBD-C6-ceramide for about 30 min, chased for about 30 min in M1 buffer at about 37° C. containing about 125 μg/mL CHX and imaged in a confocal microscope. Scale bar 5 μm (A), 2 μm (B) and 10 μm (C).

Transferrin Receptor Pathway $I^{Tf}$ is conjugated with human holo-transferrin using a hetero bi-functional crosslinker (Sulfosuccinimidyl-6-(3'-[2-pyridyldithio]-propionamido) hexanoate) or sulfo-LC-SPDP or N-succinimidyl-3-(2-pyridyldithio) propionate (SPDP). Briefly, transferrin is conjugated to sulfo-LC-SPDP in PBS-EDTA (about 20 mM Na-Phosphate buffer pH 7.4, about 1 mM EDTA) at room temperature for about 6 hours. Conjugated transferrin-SPDP (Tf-SPDP) is purified using a 30 kDa Amicon. Amicon is a molecular cut-off filter that allows anything less than 30 kDa to pass and over 30 kDa to be retained.

The amount of SPDP conjugation is quantified and about 2-5 moles of SPDP/Tf is obtained which is further conjugated to thiol modified $I^{Tf}$ by mixing them in a 1:2.5 to 1:5 ratio in about 20 mM PBS-EDTA followed by 24 hour incubation at about 4° C. Formation of Tf-$I^{Tf}$ conjugate is assayed using about 3% Agarose-TAE gel.

Next, the transferrin receptor pathway is marked using the DNA sensor/comprising Nucleic Acid Assembly—$I^{Tf}$ conjugated to human holo-transferrin (Tf) through a hetero bi-functional cross linker, N-succinimidyl-3-(2-pyridyldithio) propionate (SPDP), to give Tf-$I^{Tf}{}_{A488/A647}$ which is further tested in IA2.2 cells to label endocytic compartments (FIG. 10,12).

FIG. 10 describes conjugation of $I^{Tf}{}_{A488/A647}$ with transferrin. Thiolated DNA sensor $I^{Tf}$ is conjugated with SPDP-modified transferrin at about 4° C. overnight. Different species are then resolved in a 3% Agarose-TAE gel and run for about 1 hour at room temperature. FIG. 10 shows that $I^{Tf}$-Transferrin conjugate sample migrates differently than I-Tf only samples.

Lanes—1-$I^{Tf}{}_{A488/A647}$,
2—1:4 $I^{Tf}{}_{A488/A647}$:Tf-SPDP,
3—1:2.5 $I^{Tf}{}_{A488/A647}$:Tf-SPDP.

FIG. 11 describes Size Exclusion Chromatography (SEC) purification of Tf-$I^{Tf}$ DNA conjugates. DNA sensor conjugates are injected in a SEC-HPLC and separated using an isocratic flow of PBS, at pH of about 7.4, over about 16 minutes. Samples are monitored by their absorbance at 260 nm. $V_o$ (void volume) and exclusion limit Vex are measured by injecting Blue-Dextran and ATP respectively. 1 and 2: Fractions are collected and analyzed further using gel electrophoresis.

FIG. 12 depicts identification and characterization of Tf-$I^{Tf}$ conjugate separated by SEC-HPLC. This experiment is carried out to purify conjugates from a mixture of $I^{Tf}$, transferrin and SPDP. Biosep 54000 column is used in combination with Shimadzu HPLC system. 1 mL/min Isocratic plow of PBS 7.3-7.4 is used as solvent. 100 μL of samples is injected using an automated sample injector and monitored over 20-25 min. Absorbance at 260, 488 and 555 nm is followed to identify each eluting sample.

SEC fractions collected at indicated times are resolved in 3% Agarose-TAE run for about 1 hour at room temperature.
1. Thiolated I-switch,
2. SEC fraction eluted at retention time $R_t$–8 min.

When a cocktail of $Tfn_{A568}$ and $Tf-I^{Tf}_{A488/A647}$ is used to pulse the cells for about 10 min, they are co-localized in the sorting endosome (FIGS. 2 D, I). When $Tf_{A568}$ and $Tf-I^{Tf}_{A488/A647}$ are pulsed for about 10 min followed by a 12 minute chase, they are co-localised in perinuclear recycling endosomes (FIG. 2E, J). This indicates that DNA sensors programmed to display endocytic ligands are trafficked down the specific endocytic pathway of the corresponding receptor without perturbing its natural trafficking characteristics.

Example 8: Performance of Programmed DNA Sensors in Cellulo

This experiment is performed to determine the in cellulo pH response curve of DNA sensors and analyse performance of the sensors inside organelles. I$^n$ order to assess the in cellulo performance of each of the programmed DNA sensors, either $Tf-I^{Tf}_{A488/A647}$ or $I^{Fu}_{A546/A647}$ is endocytosed by scFv-furin expressing IA2.2 cells. Post-endocytosis, the in cellulo pH is clamped at values ranging between pH of about 5.0 and about 7.5 and the donor to acceptor (D/A) ratios are plotted as a function of pH. These results show that the in vitro pH response characteristics of the programmed DNA sensors are preserved in cellulo (FIG. 1e, f). As the in vitro and in cellulo pH response curves are similar, it is derived that the performance of the DNA sensors in vitro and in cellulo is indistinguishable.

Next, spatiotemporal pH mapping is carried out with each sensor separately. Sorting endosomes are labelled by pulsing scFv-furin expressing IA2.2 cells with $I^{Fu}_{A546/A647}$ for about 10 min, washed and imaged. A histogram of pH values of all labelled sorting endosomes reveals a uniform pH distribution with a mean pH of about 5.98±0.02, characteristic of sorting endosomes (FIG. 3A, C). From the histogram, mean D/A value is measured and this D/A is compared with the in cellulo calibration curve and pH is measured.

When the late endosomes of scFv-Furin expressing cells are labelled by pulsing these cells with $I^{Fu}_{A546/A647}$ for about 30 min and chasing for about 45 min, the pH distribution of endosomes reveals a distinct shift to lower D/A values corresponding to a pH of about 5.72±0.08, characteristic of late endosomes (FIG. 3D, F).

Next, the TGN of scFv-furin expressing IA2.2 cells is labelled with $I^{Fu}_{A546/A647}$ as described. FIG. 3G shows the pH map of the TGN that reveals the degree of spatial pH heterogeneity therein to be about 6.18±0.01 (FIG. 3G-I). Similarly, the ability of $Tf-I^{Tf}_{A488/A647}$ to capture spatiotemporal maps of transferrin trafficking are carried out in scFv-furin expressing IA2.2 cells. The sorting endosomes are marked by pulsing these cells with $Tf-I^{Tf}_{A488/A647}$ for about 10 min at about 37° C.

FIG. 3J shows sorting endosomes distributed throughout the cytoplasm and a frequency distribution of their pH gives an average pH of about 6.09±0.01 (FIG. 3J-L). Upon further chasing for about 12 min, $Tf-I^{Tf}_{A488/A647}$ concentrates at a pericentriolar location characteristic of recycling endosomes (FIG. 3M).

A few endosomes present at the periphery of the cell show D/A values very similar to the sorting endosome whilst the pericentriolar endosomes show substantially higher D/A indicating an associated pH of about 6.35±0.04 (FIG. 3N, O).

Figure 3:
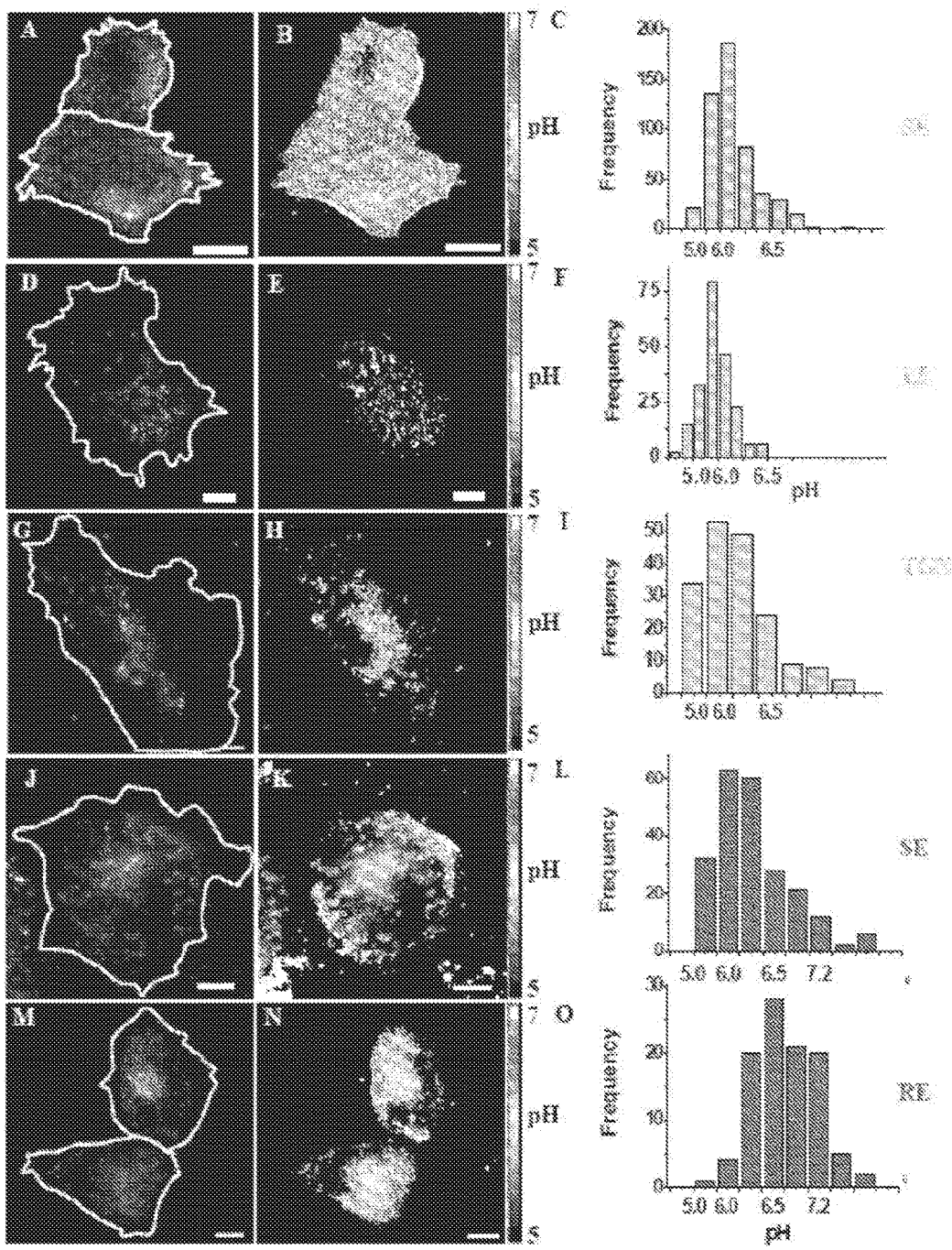
FIG. 3 depicts in cellulo performance of programmed DNA sensors.

FIG. 3 depicts in cellulo performance of programmed DNA sensors. Temporal pH maps of endosomal organelles using $Tf-I^{Tf}_{A488/A647}$ and $I^{Fu}_{A546/A647}$ are provided. scFv-furin expressing IA2.2 cells are labelled with $I^{Fu}_{A546/A647}$ for: (A and B)—10 min at about 37° C., washed and immediately imaged.

(D and E)—Pulsed for about 30 min, chased for about 45 min at 37° C., washed and imaged.

(G and H)—for 2 hours, washed, chased for 90 min in CHX and imaged. pH distributions of (C) early endosomes, (F) late endosomes and (I) trans-Golgi network are revealed by $I^{Fu}_{A546/A647}$.

IA2.2 cells are labelled with $Tf-I^{Tf}_{A488/A647}$ for:
(J and K) 10 min, washed and imaged,
(M-N)—for 10 min followed by a chase of 12 min, washed and imaged.

(L to O)—pH distribution of (L) sorting endosomes and (O) perinuclear recycling endosomes are revealed by $Tf-I^{Tf}_{A488/A647}$.

(B, E, H, K and N)—Corresponding pseudocolour D/A map of cells typically marked with $Tf-I^{Tf}$ and $I^{Fu}$.

Experiments are performed in duplicate. Scale bar: 10 µm.

Cumulatively, this indicates that, individually, each programmed DNA sensor:
(i) follows the endocytic pathway of the respective membrane trafficking protein it is programmed to target,
(ii) quantitatively recapitulates its pH sensing characteristics inside cells, and
(iii) provides high resolution spatiotemporal pH maps of those sub-cellular organelles whose pH it is designed to report.

Example 9: Simultaneous pH Mapping Technology in Cellulo

Having characterized the individual trafficking properties and performance of both programmed DNA sensors, spatiotemporal pH changes along both endocytic pathways within the same live cell are simultaneously mapped in an embodiment of the present disclosure.

There are two different methods to achieve simultaneous pH mapping, which are:
(i) sequential timed pulse/chase of cells with solutions of individual programmed DNA sensors that localise $Tf-I^{Tf}_{A488/A647}$ and $I^{Fu}_{A546/A647}$ in different endocytic compartments of each pathway and
(ii) a simultaneous pulse/chase of a cocktail of $Tf-I^{Tf}_{A488/A647}$ and $I^{Fu}_{A546/A647}$ that delivers both DNA sensors into the same endocytic compartment from where, with time, they segregate into different organelles along each pathway.

As an initial example, the process by which programmed DNA sensors are used sequentially to mark early endosomes and late endosomes of the transferrin receptor and furin endocytic pathways respectively are described (FIG. 13). FIG. 13 depicts schematic representation of pulse and chase involved for "SimpHony".

Sequential pulse—Late endosomes are labelled first with about 500 nM $I^{Fu}_{A546/A647}$ for 30 min in about 100 µL complete media at about 37° C. and chased for about 45 min. To mark early/sorting and recycling endosomes of same cells, a second pulse of about 500 nM $Tf-I^{Tf}_{A488/A647}$ in about 50 µL M1 buffer is introduced for about 10 min at about 37° C.

In a Simultaneous pulse, scFv-Furin expressing IA2.2 cells are labelled for about 10 min with a mixture of Tf-I$^{Tf}_{A488/A647}$ and I$^{Fu}_{A546/A647}$ (about 500 nM each) in 50 µL M1 buffer at about 37° C.

Sequential pH Mapping scFv-furin expressing IA2.2 cells are first pulsed with about 500 nM I$^{Fu}_{A546/A647}$ for about 10 min, washed and chased for about 45 min to mark all the late endosomes on the furin retrograde endocytic pathway. After a chase of about 45 min, the same cells are pulsed with about 500 nM Tf-I$^{Tf}_{A488/A647}$ for about 10 min that mark all the early/sorting endosomes. FIGS. 4A to G show the images of a typical single cell marked as described above.

FIGS. 4A and B show the images in the donor channel (520 nm) and FRET channel (669 nm) when ALEXA FLUOR®-488 fluorophore is excited. FIG. 4C shows an overlay of the intensities in the donor (magenta) and FRET channels (blue), giving a qualitative indication of pH heterogeneity in the early endosomes marked with Tf-I$^{Tf}_{A488/A647}$; that is quantified in FIG. 4H. Each endosomal D/A is noted and a collection of more than 200 endosomes is plotted in a histogram, as seen in FIGS. 4H and I.

Similarly, FIG. 4D to F show the images of the same cell as marked by I$^{Fu}_{A546/A647}$. FIGS. 4D and E show the intensities in the donor channel (570 nm) and FRET channel (669 nm) when ALEXA FLUOR®-546 fluorophore on I$^{Fu}_{A546/A647}$ is excited. FIG. 4F shows an overlay of the intensities in the donor (red) and FRET channels (green) respectively, giving a qualitative indication of pH heterogeneity in the late endosomes marked with I$^{Fu}_{A546/A647}$; that is quantified in FIG. 4I.

FIG. 4G shows an overlay of the images of FIGS. 4C and F that reveals the ability of programmed DNA sensors to capture spatial pH heterogeneity of two types of endocytic compartments, namely early and late endosomes, simultaneously within the same cell. I" a similar manner, spatial pH maps of the recycling endosomes and the late endosomes using Tf-I$^{Tf}_{A488/A647}$ and I$^{Fu}_{A546/A647}$ are obtained (FIG. 14).

FIG. 14 depicts Simultaneous pH mapping of recycling endosomes and late endosomes. scFv-Furin expressing IA2.2 cells are pulsed with about 500 nM of I$^{Fu}_{A546/A647}$ for about 30 min, chased for about 45 min, followed by a second pulse of about 500 nM of Tf-I$^{Tf}_{A488/A647}$ for about 10 min and a 12 min chase, washed with M1 buffer and imaged in a widefield microscope. Tf-I$^{Tf}$ positive endosomes are shown in magenta and blue while I$^{Fu}$ positive endosomes are represented in red and green respectively. Scale bar: 5 µm.

FIG. 4J shows a representative cell image for the SimpHony spatial pH map on recycling and late endosomes that is analogous to FIG. 4G (SimpHony on early and late endosomes).

Simultaneous marking of recycling endosomes and late endosomes is achieved by first labelling scFv-Furin expressing IA2.2 cells with about 500 nM I$^{Fu}_{A546/A647}$ in complete media for about 30 minutes and chased for about 45 minutes. Recycling endosomes in the same set of cells are marked by pulsing about 500 nM Tf-I$^{Tf}_{A488/A647}$ for about 10 minutes followed by a 12 minute chase in about 1 mL M1 buffer.

FIGS. 4K and L quantify the observed pH distributions for the recycling and late endosomes respectively, which are consistent with the expected values for these organelles (Table 3). FIG. 4M shows a representative simultaneous spatial pH map of the sorting endosome and TGN revealed by Tf-I$^{Tf}_{A488/A647}$ and I$^{Fu}_{A546/A647}$ and the reported pH heterogeneity is quantified in FIGS. 4N and O). Each endosomal D/A is noted and a collection of more than 200 endosomes is plotted in a histogram, as seen in FIGS. 4N and O.

FIG. 15 depicts simultaneous pH mapping of early/sorting endosomes and TGN. Tf-I$^{Tf}$ positive endosomes are shown in magenta and blue while I$^{Fu}$ positive TGN is represented in red and green respectively. Scale bar: 5 µm.

Simultaneous marking of early/sorting endosomes and TGN is achieved by two step labelling. scFv-Furin expressing IA2.2 cells are pulsed with about 500 nM I$^{Fu}_{A546/A647}$ in complete media containing about 125 µg/mL CHX for 2 hours, chased in same CHX containing media for about 90 minutes to achieve TGN accumulation. Sorting endosomes in the same set of cells are marked by pulsing about 500 nM Tf-I$^{Tf}_{A488/A647}$ for about 10 minutes in 50 µL M1 buffer containing about 125 µg/mL CHX. The cells are washed and imaged in a wide-field microscope.

FIG. 4P shows a representative simultaneous spatial pH map of the recycling endosome and TGN revealed by Tf-I$^{Tf}_{A488/A647}$ and I$^{Fu}_{A546/A647}$ and the reported pH heterogeneity of these organelles is quantified in FIGS. 4Q and R respectively (FIG. 16). Importantly, the pH values of the early, late and recycling endosomes as well as TGN, revealed by SimpHony show excellent correlation with the literature as well as the non-SimpHony values that are measured using only one DNA sensor (Table 2).

FIG. 4 depicts simultaneous pH mapping of transferrin receptor and furin mediated endocytic pathways using DNA sensors with Sequential pulse (A to R) and Simultaneous pulse (S to W).

(A to C)—Simultaneous pH mapping of early endosomes and (D to F)—late endosomes.

(G)—Simultaneous spatial pH maps of early endosomes and late endosomes in a single cell labelled with Tf-I$^{Tf}_{A488/A647}$ and I$^{Fu}_{A546/A647}$ respectively. Early/sorting endosomes are shown in magenta and blue (A488 and FRET647 channel respectively) while late endosomes are shown in red and green (A546 and FRET647 channel respectively).

(H)—Quantification of pH heterogeneity of early/sorting endosomes by Tf-I$^{Tf}_{A488/A647}$ and (I) late endosomes by I$^{Fu}_{A546/A647}$.

(J to L)—Simultaneous pH mapping of recycling endosomes and late endosomes marked with Tf-I$^{Tf}_{A488/A647}$ and I$^{Fu}_{A546/A647}$ respectively and their corresponding pH distributions. (M to O)—Simultaneous pH mapping of early/sorting endosomes and TGN marked with Tf-I$^{Tf}_{A488/A647}$ and I$^{Fu}_{A546/A647}$ respectively and their corresponding pH distributions.

(P to R)—Simultaneous pH mapping of recycling endosomes and TGN marked with Tf-I$^{Tf}_{A488/A647}$ and I$^{Fu}_{A546/A647}$ respectively and their corresponding pH distributions.

(S to U)—Simultaneous pulse of Tf-I$^{Tf}_{A488/A647}$ and I$^{Fu}_{A546/A647}$. (T) for 10 min showing their colocalization in early/sorting endosomes.

(V and W)—pH distribution of early endosomes revealed simultaneously by Tf-I$^{Tf}_{A488/A647}$ (V) and I$^{Fu}_{A546/A647}$ (W).

(X and Y)—pH heterogeneity of sorting endosomes revealed by single pulse with Tf-I$^{Tf}_{A488/A647}$ (X) or with I$^{Fu}_{A546/A647}$ (Y).

All experiments are performed in duplicate. Scale bar: 5 µm.

FIG. 16 depicts Simultaneous pH mapping of recycling endosomes and TGN. scFv-Furin expressing IA2.2 cells are pulsed with I$^{Fu}_{A546/A647}$ for about 120 min in presence of about 125 µg/mL CHX, chased for about 90 min in presence of CHX, followed by a second pulse of Tf-I$^{Tf}_{A488/A647}$ for about 10 min and a 12 min chase, washed and imaged in a widefield microscope. Tf-I$^{Tf}$ positive endosomes are shown in magenta and blue while I$^{Fu}$ positive TGN are represented in red and green respectively. Scale bar: 5 μm.

Table 2 provides a comparative analysis of organellar acidity measured by DNA sensors either alone or simultaneously. It is derived from the Table 2 provided below that the organellar acidity as measured by DNA sensors of the present disclosure is in compliance with the findings of the prior art.

| Compartments | I$^{Fu}_{A546/A647}$ | | Tf-I$^{Tf}_{A488/A647}$ | |
|---|---|---|---|---|
| | Single | SimpHony | Single | SimpHony |
| SE | 5.98 ± 02 | 6.0 ± 0.05* | 6.09 ± 0.01 | 6.09 ± 0.09 |
| LE | 5.72 ± 08 | 5.43 ± 0.19 | — | |
| RE | — | | 6.35 ± 0.04 | 6.56 ± 0.11 |
| TGN | 6.18 ± 0.01 | 6.16 ± 0.09 | — | |

*measured by simultaneous pulsing;

Simultaneous marking of recycling endosomes and TGN is achieved by a two step labelling. scFv-Furin expressing IA2.2 cells are pulsed with about 500 nM I$^{Fu}_{A546/A647}$ in about 100 μL complete media containing about 125 μg/mL CHX for about 2 hours, chased in same CHX containing media for about 90 min to achieve TGN accumulation. Recycling endosomes in the same set of cells are marked by pulsing about 500 nM Tf-I$^{Tf}_{A488/A647}$ for about 10 min in about 50 μL M1 buffer containing about 125 μg/mL CHX and chased for about 12 min in same buffer.

Simultaneous pH Mapping in Same Organelle

Having demonstrated SimpHony in a single cell where each of the two DNA sensors is positioned in two different organelles that occupy spatially distinct regions, the aspect of both DNA sensors working in tandem within the same organelle is analysed and pH dynamics are reported in an embodiment of the present disclosure.

In order to achieve this, scFv-furin expressing IA2.2 cells are incubated with a mixture of about 500 nM I$^{Fu}_{A546/A647}$ and about 500 nM Tf-I$^{Tf}_{A488/A647}$ for about 10 min, washed with M1 buffer and imaged. This results in abundant co-localization of I$^{Fu}_{A546/A647}$ and Tf-I$^{Tf}_{A488/A647}$ in the sorting endosomes (FIG. 4S-U), and the pH heterogeneity captured by each DNA sensor is quantified. For quantification, each endosomal D/A is noted and a collection of more than 200 endosomes is plotted in a histogram.

Upon pH quantification of those endosomes that show co-localization of I$^{Fu}_{A546/A647}$ and Tf-I$^{Tf}_{A488/A647}$, it is found that Tf-I$^{Tf}_{A488/A647}$ reveals a pH spread of about 5.93±0.16 (FIG. 4V) while I$^{Fu}_{A546/A647}$ reports a spread of about 6.0±0.05 (FIG. 4W), consistent with Tf-I$^{Tf}_{A488/A647}$. These results are also in agreement with sorting endosome pH distributions as mapped with either DNA sensor alone (FIG. 4X, Y and Table 2), indicating that any crosstalk between both devices is insignificant.

This demonstrates that both DNA sensors function autonomously within the cell and independently of each other even when present in the same compartment, reaffirming the non-interfering nature of DNA sensors/DNA-based pH sensitive nanodevices.

Example 10: SIMpHONY Reveals Organellar Morphology is Coupled to their Lumenal pH Given the high precision simultaneous pH maps that are captured using SimpHony, its applicability is demonstrated by capturing functional pH correlates associated with perturbations of organelle morphology, if any.

Recent studies have shown that chemical inhibition of dynamin by dynasore arrests endosomal fission and fusion; causes tubulation of the early endosome and prevents endosomal maturation. Dynamin is additionally known to interact with actin nucleation promoting factor WASH, which when blocked, also inhibits fission of the early endosome, causing early endosomal tubulation and arrests endosomal dynamics. The inhibition of fission, induced by Dynasore is predicted to result in hypo-acidification of the early endosome, which affects its maturation.

The DNA sensor of the present disclosure is applied to this system, by marking early endosomes with about 500 nM Tf-I$^{Tf}_{A488/A647}$ and late endosomes with about 500 nM I$^{Fu}_{A546/A647}$ in the presence and absence of Dynasore. I" the absence of Dynasore, early endosomes undergo active fusion and fission; showing an average pH of about 6.05±0.07 (FIG. 17) while the late endosomes show an average pH of about 5.43±0.3.

In the presence of about 160 μM dynasore, the characteristic morphological change of extensive tubulation of the early endosomes as well as their arrested dynamics is observed (FIG. 17). SimpHony reveals that this tubulation is also accompanied by a clear elevation of lumenal pH spanning about 6.1 to about 6.7 (mean pH 6.58±0.19) (FIG. 5E). I" contrast, lumenal pH of late endosomes shows a negligible pH change (5.44±0.38).

Importantly, when Dynasore is washed out, early endosome tubulation is abolished, with endosomes regaining dynamics and showing spontaneous fusion/fission (FIG. 17).

Further, the average pH of the early endosomes is completely restored. Additionally, at all steps with and without Dynasore, the lumenal pH of another related organelle such as the late endosome remains unaffected.

SimpHony reveals that in these voluminous and tubular early endosomes, there is hypo-acidification of the lumen. SimpHony provides the direct pH read-out of both early and late endosomes simultaneously, and conclusively establishes Dynasore-induced hypo-acidification within Early Endosomes, providing clarity on a pH-dependent phenomenon in early endosomal maturation.

FIG. 5 depicts simultaneous pH mapping of organelles with altered morphology. The simultaneous pH mapping by DNA sensors of the present disclosure reveals Dynamin-mediated pH change that triggers early endosomal fission.

(a,b) Time-lapse images of EEs labelled with Tf-I$^{Tf}_{A488/A647}$ and I$^{Fu}_{A546/A647}$ showing active and arrested dynamics in the absence (a) and presence (b) of 160 μM dynasore, respectively. I$^{Fu}_{A546/A647}$ and Tf-I$^{Tf}_{A488/A647}$ co-localize in EEs (yellow pixels). Green and red arrowheads indicate endosomes containing Tf-I$^{Tf}$ and I', respectively, segregating their individual pathways due to EE fission. I" the presence of dynasore, EE fission is blocked, retaining both I$^{Fu}_{A546/A647}$ and Tf-I$^{Tf}_{A488/A647}$ in EEs (yellow pixels, shown by a white arrowhead).

(c-h) SimpHony of EEs and LEs revealed by Tf-I$^{Tf}$ and I$^{Fu}$, respectively, in the absence (c,d), presence (e,f) and after washing out (g,h) of dynasore.

(i-j) SimpHony of TGN in the presence of brefeldin A (BFA). TGN is labelled with I$^{Fu}_{A546/A647}$ and stained with NBD-C6-ceramide in the absence (i) or presence (j) of brefeldin A for 10 min.

Inset in j: zoomed images (green, NBD; red, I$^{Fu}$; white, merged image) of regions corresponding to the right arrowhead and asterisk; the left arrowhead indicates the TGN.

(k,l) pH maps of TGN. Cells are marked with $I^{Fu}{}_{A546/A647}$, and imaged in the absence (k) or presence (l) of BFA. The top panel represents the greyscale image, and the bottom panel represents its corresponding pseudocolour D/A image. Pixels are colour coded on the basis of their D/A ratios, with blue pixels denoting low D/A ratios and red pixels indicating high D/A ratios.

In (i-l), all images are single-plane confocal images, with individual cells demarcated by a white outline.

(m-p) SimpHony of EE and TGN revealed by Tf-I$^{Tf}$ and I$^{Fu}$, respectively: pH distribution of EEs (m,o); pH distribution of the TGN (n,p).

Experiments were performed in triplicate. Scale bars, 3 μm (a,b) and 10 μm (i-l).

FIG. 17 depicts Dynasore mediated arrest of endosomal fission. Early/sorting and late endosomes in IA2.2 cells expressing scFv-furin are marked with about 500 nM Tf-I$^{Tf}{}_{A488/A647}$ at 37° C. for 10 min. Time lapse images of control cells (−Dy) where no dynasore is added, (+Dy) in presence of about 160 μM dynasore and (W) after dynasore is washed out and incubated for about 10 min at about 37° C. for recovery. Images are acquired with a time interval of about 2 s over 2 min period and compressed to a movie playing at 7 fps.

From this example, it is inferred that, in the absence of Dynasore, endosomal fission and fusion are normal; while in presence of Dynasore, fission and fusion is affected. Their movement, fission and fusion are restored upon washing of dynasore.

Example 11: SIMpHONY on BFA Treated Cells

Having captured the predicted defective acidification associated with a morphological change of an organelle such as the early endosome, SimpHony is applied to a very important alteration of organelle morphology where functional pH correlates are as yet unknown, in an embodiment of the present disclosure.

The fungal metabolite Brefeldin A (BFA) causes extensive tubulation of the TGN, which then collapses around the MTOC (microtubule-organizing center), that is also accompanied by the rapid redistribution of Golgi resident proteins into the Endoplasmic Reticulum (ER). For example, upon treatment with BFA, the TGN resident mannose-6-phospate receptor is distributed in tubules and fuses with Transferrin containing early endosomes while Furin positive tubules originating from the TGN are devoid of Transferrin (FIG. 18a, b).

FIG. 18 depicts effect of Brefeldin A on Early Endosome and TGN. Furin containing tubules do not co-localize with transferrin.

(a) scFv-Furin expressing cells are pulsed with about 500 nM I$^{Fu}{}_{A488/647}$ for 2 hours and chased for 30 min in presence of about 125 ug/mL CHX to label TGN followed by about 20 μg/mL BFA treatment for 10 min at 37° C.

(b) EGFP-Furin expressing cells are treated with about 20 μg/mL BFA for 10 min. Cells are pulsed with 1 in 1000 dilution of Tfn$_{568}$ in presence of about 20 μg/mL BFA and about 125 μg/mL CHX to label early endosomes. Scale bar: 10 μm.

SimpHony is applied on BFA-induced tubules positive for furin marked by I$^{Fu}{}_{A546/A647}$ while simultaneously marking transferrin containing endosomes with Tf-I$^{Tf}{}_{A488/A647}$. BFA treated cells show tubular extensions emerging from compartments localize near the MTOC (FIG. 18a). Tf-I$^{Tf}{}_{A488/A647}$ in these cells occupies the excluded space of I$^{Fu}{}_{A546/A647}$ in the region around the MTOC in addition to a few cytoplasmic endosomes (FIG. 19b).

Thus, furin containing compartments tubulate extensively upon BFA treatment and do not co-localize with transferrin (FIG. 19b). Co-localization studies with I$^{Fu}{}_{A488/A647}$ with both anti-TGN46 and NBD ceramide confirm that these BFA-induced tubules are indeed TGN related (FIG. 20). Although BFA-induced tubulation and protein redistribution in the Golgi has been extensively studied; spatial pH maps that indicate the functional environment in these tubular regions have remained elusive.

FIG. 19 depicts localization of Tf-I$^{Tf}$ and I$^{Fu}$ DNA sensors in compartments after BFA treatment. scFv-Furin expressing IA2.2 cells are pulsed with about 500 nM I$^{Fu}{}_{A546/647}$ for 2 hours and chased for 30 min in presence of CHX followed by absence (a) or presence (b) of BFA (about 20 μg/mL) treatment of about 10 min at about 37° C. Cells are pulsed with about 500 nM Tf-I$^{Tf}{}_{A488/A647}$ in presence of BFA and CHX to label early endosomes. Arrowheads show MTOC. Scale Bar: 10 μm.

FIG. 20 depicts that DNA sensors redistribute in tubules positive for TGN 46 (marker of TGN) after BFA treatment. scFv-Furin expressing IA2.2 cells are pulsed with about 500 nM I$^{Fu}{}_{A488/647}$ for 2 hours and chased for 30 min in presence of about 125 ug/mL CHX followed by absence (a) or presence (b) of BFA (about 20 μg/mL) treatment of about 10 min at 37° C. Cells are fixed and stained with 1 in 500 dilution of mouse TGN46 primary antibody followed by 1 in 500 dilution of Texas-Red conjugated secondary antibodies. Scale Bar: 10 μm.

pH heat maps of BFA treated and untreated cells show striking pH differences of I$^{Fu}{}_{A546/A647}$ containing compartments where, BFA-induced tubules show markedly high D/A values revealing a significantly elevated pH of about 6.35±0.17. Importantly, D/A values of early endosomes marked by Tf-I$^{Tf}{}_{A488/A647}$ show negligible change of pH of about 6.14±0.01 (FIG. 21, 22, Table 3).

Untreated cells reveal a mean early endosomal pH of about 6.07±0.07 and a lumenal TGN pH of about 5.94±0.15 (FIG. 22, Table 2). FIG. 21 depicts D/A heat map of cells labelled by Tf-I$^{Tf}{}_{A488A/647}$, post labelling with I$^{Fu}{}_{A546/A647}$ followed by BFA treatment for about 10 min at about 37° C. Thus, SimpHony reveals that the transformation of the TGN into tubular morphologies lowers their lumenal acidities compared to the intact TGN.

Using DNA sensor localization, along with SimpHony of a spatially close yet distinct, as well as BFA-inert, control organelle, i.e. the sorting endosome, it is proved that BFA-tubulated TGN is hypo-acidic, with its lumenal pH closer to a cis-Golgi like environment. This connects BFA-induced TGN tubulation with a pH-dependent process such as protein maturation, sorting and localization within the secretory pathway.

Taken together, SimpHony reveals that significant perturbation of physical characteristics such as morphology of intracellular compartments result in their defective acidification that is linked to the observed impairment of protein trafficking in these compartments.

The Table 3 provided below provides a comparative study of organellar acidity, pre and post treatment with BFA.

| Com-partments | I$^{Fu}{}_{A546/A647}$ | Tf-I$^{Tf}{}_{A488/A647}$ | I$^{Fu}{}_{A546/A647}$ | Tf-I$^{Tf}{}_{A488/A647}$ |
| --- | --- | --- | --- | --- |
| | −BFA | | +BFA | |
| SE/EE | — | 6.07 ± 0.07 | — | 6.14 ± 0.01 |
| Vesicles | 5.89 ± 0.16 | — | 6.02 ± 0.09 | — |

| Com-partments | $I^{Fu}_{A546/A647}$ | $Tf\text{-}I^{Tf}_{A488/A647}$ −BFA | $I^{Fu}_{A546/A647}$ | $Tf\text{-}I^{Tf}_{A488/A647}$ +BFA |
|---|---|---|---|---|
| Tubules | —* | — | 6.35 ± 0.17 | — |
| TGN | 5.94 ± 0.15# | — | — | — |

*no tubules without BFA treatment
after BFA treatment, TGN dissembles in to long tubules and thus pH of TGN cannot be measured.

Simultaneous pH Mapping of Organelles Captures Differential pH Heterogeneity

Apart from Tf-ITfA488/A647 which labels early endosomes in BFA treated cells, a second internal control is used in the same cells where BFA-induced tubule formations are predominant.

FIG. 22 describes the pH heterogeneity of early endosomes and TGN, pre and post treatment with BFA. IA2.2 cells are pulsed with about 500 nM IFuA546/A647 for about 2 hours and chased for 30 min in presence of about 125 ug/ml CHX followed by absence or presence of BFA (about 20 µg/mL) treatment of about 10 min at about 37° C. Cells are further treated with about 500 nM Tf-ITfA488/A647 in presence of about 20 µg/mL BFA and about 125 ug/ml CHX to label early endosomes.

Labelling of the TGN with IFuA546/647 shows that about 85-90% IFuA546/647 is resident in TGN while about 10-15% IFuA546/647 is present as small punctuate vesicles that are endosomes that have not yet trafficked forward to the TGN.

These endosomes show a pH of about 5.89±0.16 in the absence of BFA. I" the presence of BFA, the pH of this vesicular population is pH of about 6.02±0.09 and does not change significantly (FIGS. 22e and f). However, pH of the tubular regions containing $I^{Fu}$ and TGN markers changes significantly to 6.35±0.17 from 5.94±0.15 (FIGS. 22c and d).

In an embodiment of the present disclosure, the programmable nature of DNA sensors allows to position them in distinct intracellular compartments with exquisite precision by tagging them to specific trafficking proteins. The modular nature of DNA allows the integration of analyte-sensing domains with protein recognition domains without perturbing the recognition properties of either domain. The synthetic nature of these DNA sensors allows the incorporation of organic fluorophores that enable one to track protein localizations and simultaneously report on their ionic environments using two-colour readout.

The molecularly programmable nature of DNA sensors has the advantage to access functionality that is hitherto unmatched by any other biological or non-biological scaffold—the ability to sense the same analyte, simultaneously, in distinct intracellular locations—by using different DNA sensors, each programmed to tack onto a different protein that each marks distinct intracellular environments. It is to be noted that the pH sensitive DNA nanodevices described in the present disclosure have narrower ranges than the corresponding small molecule sensors. Therefore they provide pH maps with much greater resolution than the latter. Given the engineerability of the DNA scaffold and that I-motif stability is tunable, a range of pH sensors suited to different pH regimes are envisaged. The anticipated pH regime is required before deployment of various DNA sensors in cellulo.

SimpHony or Simultaneous pH mapping technology is immediately applicable to a variety of compartment mixing problems, and cellular fusion/fission problems in biology.

Importantly, measures of in-vivo/intracellular chemistry need not be restricted to pH. The scFv-based DNA sensor targeting technology described herein is generalizable to the chemical diversity that is sensed by DNA in order to access functionally richer chemical maps of cells. Organelle targeting together with simultaneous chemical mapping technology using DNA nanodevices opens up immense potential to integrate chemical triggers originating from within subcellular environments with biological networks.

The advantage of SimpHony, which positions DNA sensors in distinct organelles, is showcased when the chemical perturbant affects the pH in one organelle, but not the other. This demonstrates not just the response of the DNA sensors but also the precision of simultaneous sensor localization through the lack of "compartmental cross-reactivity" in such pH perturbations.

In the case of Dynasore perturbation, $I^{Tf}$ is the responsive I-switch (Early Endosome—EE) and $I^{Fu}$ is the control I-switch (Late Endosome—LE). I" case of Brefeldin A perturbation, $I^{Tf}$ is the control I-switch (Recycling Endosome—RE) and $I^{Fu}$ is the responsive I-switch (Trans Golgi Network—TGN). Further in IA2.2 cells, these pairs of organelles, (EE and LE as well as RE and TGN) are also spatially close, and the pH readouts from the DNA sensors reveal that they are indeed positioned in a compartmentally distinct manner.

Advantages of the DNA Sensors of the Present Disclosure:
1) I" the present disclosure, multiplexing DNA sensor devices inside the same living cell is seen and it is also seen that DNA device functionality is uncompromised when they are multiplexed in cellular environments.
2) The DNA sensors are non-interfering to the cell and to each other, and function autonomously within the cellular environment. This opens up avenues for multi-pronged approaches in sensing and therapy in living systems. The present disclosure shows that it is possible to achieve multiple actions, by using smaller molecular weight DNA sensors, even adjust their relative proportions to suit the extent of action required by each in a given context and thus access customized therapies—if the DNA scaffold is conducive to multiplexing.
3) The present disclosure provides a strategy to position multiple DNA sensors at will in multiple, distinct, subcellular locations within the same cell.
4) A small molecule correlate coupled to protein co-localization provides potent clues pertaining to molecular mechanisms in cell signalling by coupling their spatial proximity with a biochemical readout related to their function. I" embodiments of the present disclosure, SimpHony allows one to both mark two proteins of interest and simultaneously measure the pH in their environment.
5) SimpHony is a powerful technology to study problems in intracellular traffic. It is applied to problems related to intersecting endocytic pathways, because in this context, coupling pH to the spatial localization of a protein is a direct measure of protein function that impinges on organelle identity.
6) SimpHony is applied to capturing functional pH correlates in endosomes containing viruses (or other pathogens) versus those that do not contain pathogens, within the same cell. This aids the understanding of molecular mechanisms employed by viruses (pathogens) for their replication and infection of the host. Thus the fields of infection and immunity also gain a powerful tool.
7) SimpHony is generalizable to all sensing capabilities of nucleic acids. Nucleic acids bind small molecules such as secondary messengers and metabolites, and thus it is also possible to obtain functionally richer chemical maps (beyond pH) of protein co-localization (or not) within a cell.

8) The advantage of the nucleic acid scaffold is that one may change the sequence to have different I-motif forming affinities and thereby tune the pH response of the DNA sensor. A palette of DNA pH sensors have been engineered, that span from pH about 5.0 to about 7.4, with a specific sensor response tuned specifically to a given organelle pH.

9) A pH sensitive dye spans a larger pH range but yields lower pH resolution at any given pH within its sensitive regime. On the other hand, DNA pH sensor of the present disclosure covers a narrower pH regime, but offers a much higher dynamic range over the same. This enables one to capture much subtler changes in pH with far greater accuracy and clarity. For example, BCECF, the dual-excitation ratiometric pH indicator, whose pH range spans pH 6-8 offers less than 2 fold change in between pH 6.25 to 7 whereas in this regime, the DNA sensor $I^7_{A488/A647}$ provides about 3.0 fold change in signal. This is particularly relevant in the case of trafficking defects where changes in lumenal pH of the relevant organelle are very often subtle (0.2-0.3 pH units) and within the error of measurement using pH-sensitive fluorophores, but are captured clearly with DNA pH sensors tuned to the relevant organelle.

10) A comparison of a DNA pH sensor variant with a broader response range with Fluorescein, the most widely used pH sensitive dye is provided below. I" a given pH regime from pH 5.0 to 7.0, the DNA pH sensor and fluorescein perform with comparable efficiencies.

11) A comparison of DNA pH sensors with traditional pH-sensitive organic dyes and pH sensitive fluorescent proteins are also shown in Table 4, incorporating newly engineered DNA sensor variants.

TABLE 4

Comparison of DNA pH sensors with pH sensitive organic dyes and GFP based probes

| Name | pKa | Working regime | Sensitivity at working regime | Advantages | Disadvantages |
|---|---|---|---|---|---|
| FITC | 6.5 | 5-8 | ~5 fold | Highest sensitivity at pH above 7 | Photobleaching, Decrease in fluorescence with acidification |
| BCECF | 6.98 | 6-8 | ~2 fold | Ideal to study pH 7-8. Ratiometric | Intracellular hydrolysis of the ester bond limiting the dynamic range of fluorescence ratio determination |
| Carboxy-SNARF-1 | 7.3-7.5 | 6.4-8 | ~2.5 | pH dependent dual emission, High S/N ratio for ratiometric imaging | Low fluorescence quantum yield. High pKa limits biological application below pH 7. |
| Ecliptic phluorin | 7.1 | 5-8 | ~2 fold | Genetically encoded. Can be made ratiometric | Fluorescence is quenched at acidic pH- therefore not visible below pH 6.0. Single wavelength probe (i.e. GFP) |
| Oregon green 488 | 4.7 | 4.0-5.0 | 3 fold (from pH 4-5) | Best suited to study lysosomal pH | Only highly acidic organelles can be studied. |
| $I^{Fu}$ | ~6 | 5.5-6.5 | >3.6 fold | Bright, photostable, easy to use. FRET-based pH sensor: Not limited by fluorophore wavelengths- several FRET pairs are used. Highest dynamic range from pH 5.5 to 7 | Not possible to study pH regimes pH < 5-6.8 < pH. Reduced sensitivity between pH 5-5.5 (only ~1.5-1.8 fold increase) |
| Tf-$I^{Tf}$ | 6.15 | 5.25-6.9 | >3.5 fold | Bright, photostable, easy to use. FRET-based pH sensor: Not limited by fluorophore wavelengths- several FRET pairs are used. Easily conjugable | |
| $I^7$ | ~6.9 | 6.5-7.3 | ~3 fold | As above. | |

We claim:

1. A method of multiplexing two or more DNA sensors and optionally measuring pH in a cell, wherein each of said two or more DNA sensors independently comprises a Nucleic Acid Assembly and a fluorophore, optionally along with a protein, said method comprising steps of:
   a) adding the DNA sensors to the cell in media for cellular uptake, to obtain a cell with the DNA sensors;
   b) incubating the cell obtained in step a) in the media for multiplexing the DNA sensors, wherein the DNA sensors are engineered to follow specific cellular pathways within the cell; and
   c) mapping the multiplexed DNA sensors within the cell at time intervals, optionally determining a Donor to Acceptor ratio and optionally obtaining a calibration curve for measuring pH in the cell;

wherein the two or more DNA sensors comprise at least two spectrally distinct DNA sensors programmed to simultaneously target the same analyte in different cellular pathways within the cell.

2. The method as claimed in claim 1, wherein each of the two or more DNA sensors does not interact with or compromise functionality of another of the DNA sensors.

3. The method as claimed in claim 1, wherein the cellular pathways are selected from the group consisting of secretory pathway, transcytosis, nuclear translocation, cell-cell fusion, intracellular fission and fusion phenomena.

4. The method as claimed in claim 1, wherein the adding of the DNA sensors to the cell is sequential or simultaneous; and wherein the cell is selected from the group consisting of eukaryotic cell, prokaryotic cell and recombinant cell.

5. The method as claimed in claim 4, wherein the recombinant cell is an scFV-Furin expressing cell.

6. The method as claimed in claim 1, wherein each one of the two or more DNA sensors is engineered to follow a specific cellular pathway by conjugating the one DNA sensor with a specific protein following the specific cellular pathway; or by expressing a chimeric protein on the cell, wherein the chimeric protein comprises (1) an extracellular component recognising the one DNA sensor, and (2) an intracellular component carrying the one DNA sensor through the cellular pathway; or by internalizing the one DNA sensor in the cell, wherein the cell expresses a scavenger receptor.

7. The method as claimed in claim 1, wherein the mapping is by determining the positions of the DNA sensors at time intervals ranging from about 10 minutes to about 3 hours, using a technique selected from the group consisting of immunofluorescence staining and microscopy.

8. The method as claimed in claim 1, wherein the mapping of the multiplexed DNA sensors optionally comprises adding a molecular marker for determining the cellular compartment.

9. The method as claimed in claim 1, wherein the Donor to Acceptor ratio is obtained by measuring the intensity of a Donor and of an Acceptor fluorophore by a technique selected from the group consisting of Fluorescence Resonance Energy Transfer, Fluorescence Recovery after Photobleaching, Fluorescence Loss in Photobleaching, Ratiometric Estimation, Fluorescence Lifetime Microscopy, Anisotropy Imaging, Super-Resolution Microscopy, and Sheet Light Illumination Microscopy.

10. The method as claimed in claim 1, wherein the media comprises components selected from the group consisting of Dulbecco's Modified Eagle's medium/F-12 (1:1); Ham's F-12 Complete media; M1 Buffer; Fetal Bovine Serum at a concentration ranging from about 5% to about 15%; Streptomycin at concentration ranging from about 50 µg/ml to about 200 µg/ml; Penicillin at a concentration ranging from about 50 I.U./ml to about 200 I.U./ml; G418 at a concentration ranging from about 50 µg/ml to about 400 µg/ml; hygromycin at a concentration ranging from about 50 µg/ml to about 200 µg/ml; and combinations thereof.

11. The method as claimed in claim 1, wherein the incubation is carried out for a time duration ranging from about 1 minute to about 2 hours; and at a temperature ranging from about 0° C. to about 50° C.

12. The method as claimed in claim 1, wherein the Nucleic Acid Assembly comprises nucleobases each independently selected from the group consisting of natural nucleobases, natural modified bases, unnatural modified bases, base analogs, synthetic derivatives of nucleobases, and nucleic acid analogs; the fluorophore is selected from the group consisting of organic fluorescent dye, inorganic nanomaterial, and any combination thereof; and the protein is selected from the group consisting of Furin, Transferrin, endocytosable plasma membrane protein, protein that possesses natural receptor, trafficking protein, toxin, viral coat protein, cell penetrating peptide, signal sequence, intracellular targeting sequence, endocytic ligand, and any combinations thereof.

13. The method as claimed in claim 1, wherein the Nucleic Acid Assembly comprises a sequence selected from the group consisting of SEQ ID Nos. 1 to 14.

14. A method of multiplexing two or more DNA sensors and optionally measuring pH in a recombinant cell, wherein each of said two or more DNA sensors independently comprises a Nucleic Acid Assembly and a fluorophore, optionally along with a protein, said method comprising steps of:
   a) adding the DNA sensors to the recombinant cell in media for cellular uptake, to obtain a cell with the DNA sensors;
   b) incubating the cell obtained in step a) in the media for multiplexing the DNA sensors, wherein the DNA sensors are engineered to follow specific cellular pathways within the cell; and
   c) mapping the multiplexed DNA sensors within the cell at time intervals, optionally determining a Donor to Acceptor ratio and optionally obtaining a calibration curve for measuring pH in the cell;

wherein the two or more DNA sensors comprise at least two spectrally distinct DNA sensors programmed to simultaneously target different cellular pathways within the recombinant cell, wherein the adding of the DNA sensors to the recombinant cell is sequential or simultaneous, and
wherein the recombinant cell is an scFv-Furin expressing recombinant cell.

* * * * *